(12) United States Patent
Lewkonya et al.

(10) Patent No.: US 10,874,589 B2
(45) Date of Patent: Dec. 29, 2020

(54) SYSTEMS FOR INTERFACING BETWEEN A SYRINGE, A DRUG VIAL AND A NEEDLE

(71) Applicant: Dali Medical Devices Ltd., Yavne (IL)

(72) Inventors: Gad Lewkonya, Neve Mivtach (IL); David Daily, Herzliya (IL); Hagay Drori, Tel-Aviv (IL)

(73) Assignee: DALI MEDICAL DEVICES LTD., Yavne (IL)

( * ) Notice: Subject to any disclaimer, the term of this patent is extended or adjusted under 35 U.S.C. 154(b) by 300 days.

(21) Appl. No.: 15/577,344

(22) PCT Filed: Jun. 13, 2016

(86) PCT No.: PCT/IL2016/050616
§ 371 (c)(1),
(2) Date: Nov. 28, 2017

(87) PCT Pub. No.: WO2016/203464
PCT Pub. Date: Dec. 22, 2016

(65) Prior Publication Data
US 2018/0153771 A1 Jun. 7, 2018

Related U.S. Application Data

(60) Provisional application No. 62/175,318, filed on Jun. 14, 2015, provisional application No. 62/175,314, filed on Jun. 14, 2015.

(51) Int. Cl.
*A61J 1/20* (2006.01)
*A61M 5/34* (2006.01)
(Continued)

(52) U.S. Cl.
CPC .......... *A61J 1/2062* (2015.05); *A61J 1/2089* (2013.01); *A61J 1/2096* (2013.01); *A61M 5/345* (2013.01);
(Continued)

(58) Field of Classification Search
None
See application file for complete search history.

(56) References Cited

U.S. PATENT DOCUMENTS 4,534,758 A * 8/1985 Akers ................. A61M 5/1409
604/247
6,457,488 B2 * 10/2002 Loo ..................... A61M 39/223
137/625.47
(Continued)

FOREIGN PATENT DOCUMENTS

WO  WO-2009126720 A1 * 10/2009  ........... A61J 1/2089
WO       2013128444 A1    9/2013
(Continued)

*Primary Examiner* — Adam Marcetich
(74) *Attorney, Agent, or Firm* — Naomi S. Rosenman-Helfand

(57) ABSTRACT

Systems and devices for interfacing between a medicinal vial, a hypodermic needle, and an injection device such as a syringe, comprising a valve, functionally associated with said vial adaptor, said injection device port, and said needle, said valve having a first orientation wherein said injection device port is in fluid flow communication with said vial adaptor and a second orientation wherein said injection device port is in fluid flow communication with said hypodermic needle, wherein rotation of said injection device port between a first position and a second position thereof, drives transition of said valve from said first orientation to said second orientation.

17 Claims, 46 Drawing Sheets

(51) Int. Cl.
  *A61M 39/22* (2006.01)
  *A61M 39/10* (2006.01)
(52) U.S. Cl.
  CPC ............ *A61M 39/10* (2013.01); *A61M 39/22* (2013.01); *A61M 39/223* (2013.01); *A61M 39/1011* (2013.01); *A61M 2039/1077* (2013.01)

(56) References Cited

U.S. PATENT DOCUMENTS

| | | | | |
|---|---|---|---|---|
| 7,985,216 B2* | 7/2011 | Daily | ............... | A61J 1/2096 604/131 |
| 2004/0039346 A1* | 2/2004 | Baldwin | ............. | A61M 39/223 604/236 |
| 2006/0049209 A1* | 3/2006 | Baker | ............... | A61M 5/14216 222/252 |
| 2006/0089603 A1* | 4/2006 | Truitt | ............... | A61M 39/02 604/246 |
| 2008/0306469 A1* | 12/2008 | Masuda | ............... | A61M 39/22 604/535 |
| 2009/0018506 A1* | 1/2009 | Daily | ............... | A61J 1/2096 604/136 |
| 2010/0087786 A1* | 4/2010 | Zinger | ............... | A61J 1/2096 604/224 |
| 2010/0286661 A1* | 11/2010 | Raday | ............... | A61J 1/2096 604/520 |
| 2010/0305548 A1* | 12/2010 | Kraushaar | ............. | A61J 1/2096 604/518 |
| 2013/0079744 A1* | 3/2013 | Okiyama | ............. | A61J 1/2089 604/408 |
| 2014/0196792 A1* | 7/2014 | Torres-Leon | ........... | F16K 27/12 137/1 |
| 2014/0276215 A1* | 9/2014 | Nelson | ............... | A61M 39/225 600/573 |
| 2014/0346386 A1* | 11/2014 | Tornblom | ........... | F16K 11/0856 251/311 |
| 2015/0083950 A1* | 3/2015 | Okiyama | ............. | A61J 1/2089 251/148 |
| 2015/0126974 A1* | 5/2015 | Sanders | ............... | A61J 1/2096 604/533 |
| 2015/0182699 A1* | 7/2015 | Daily | ............... | A61J 1/1406 604/187 |

FOREIGN PATENT DOCUMENTS

| | | | | |
|---|---|---|---|---|
| WO | 2013128455 A1 | 9/2013 | | |
| WO | WO-2013128444 A1 * | 9/2013 | ......... | A61M 39/223 |
| WO | WO-2014006552 A2 * | 1/2014 | ......... | A61M 5/1782 |

* cited by examiner

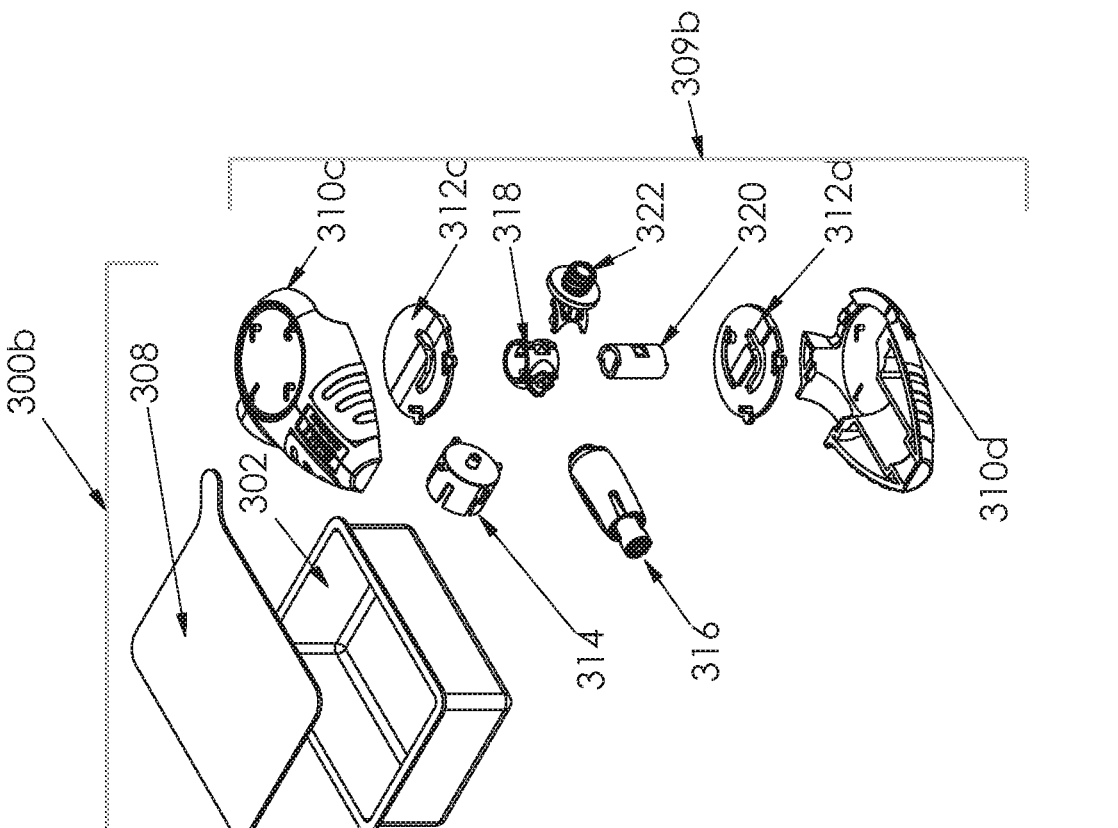
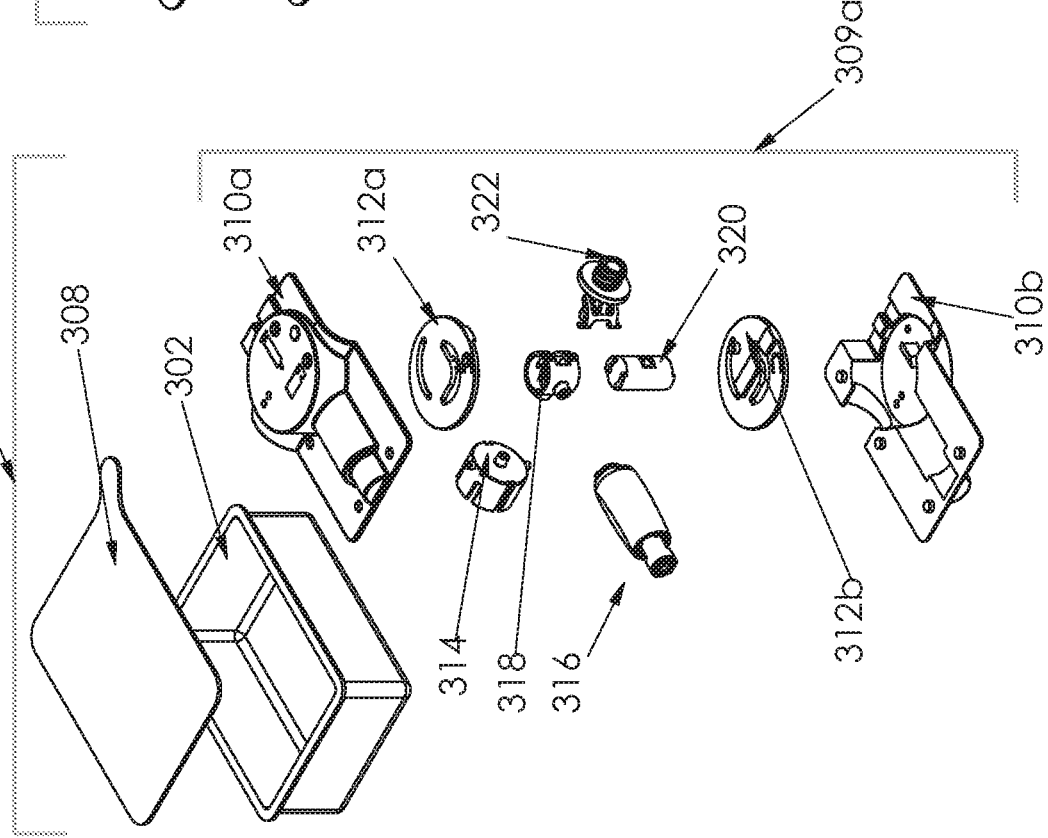

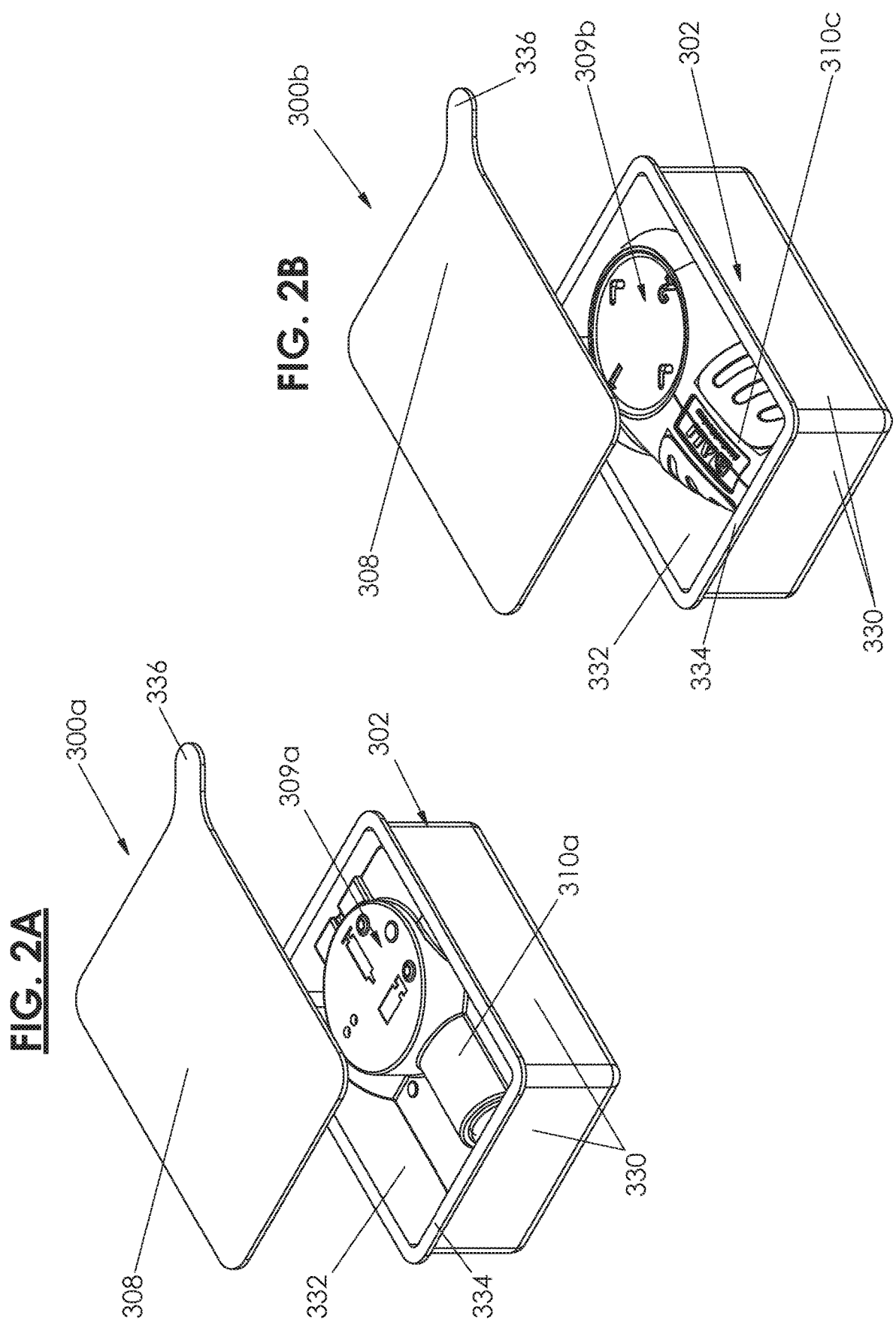

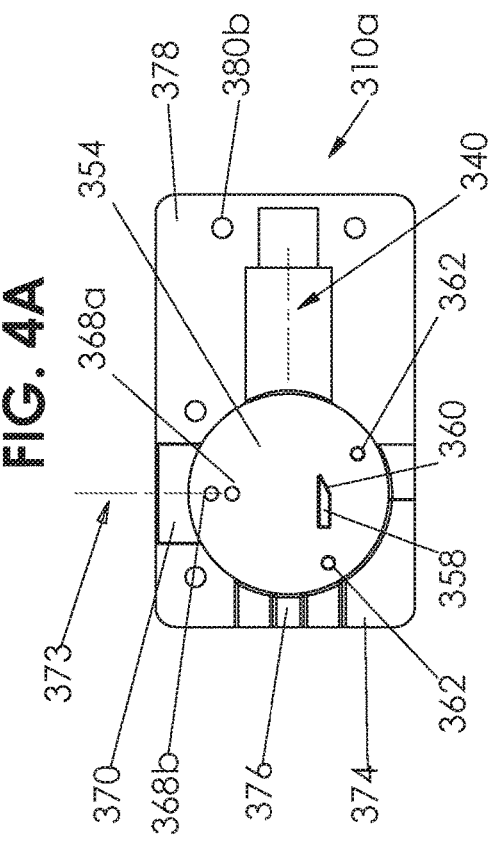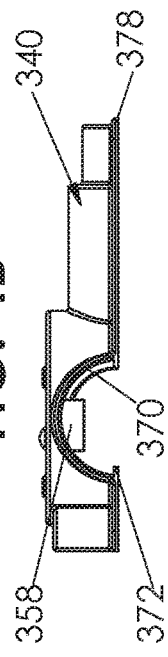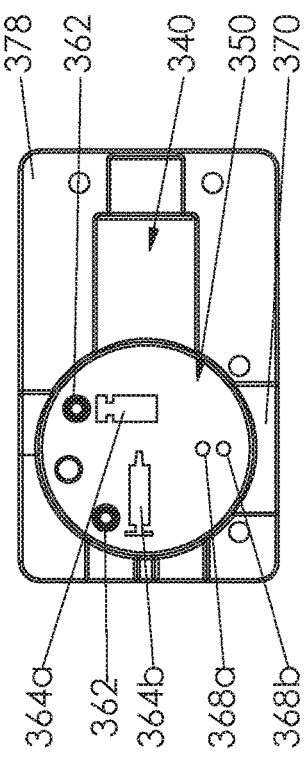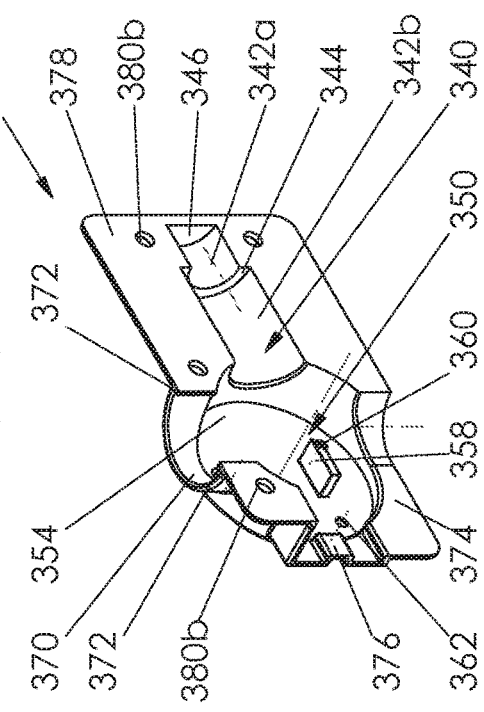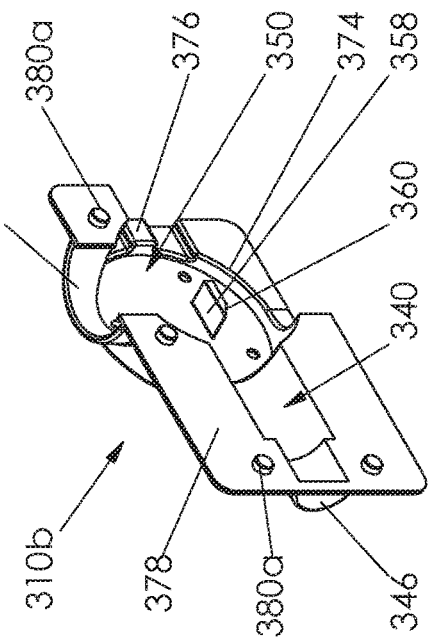

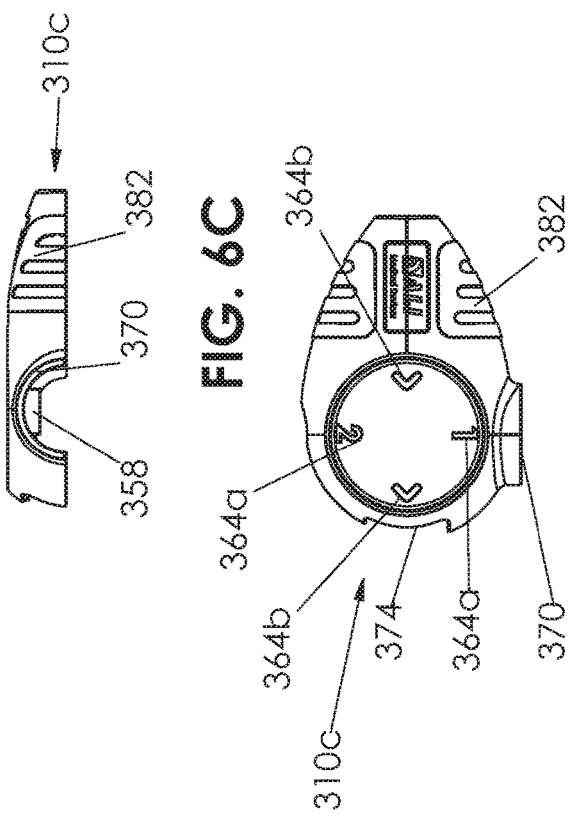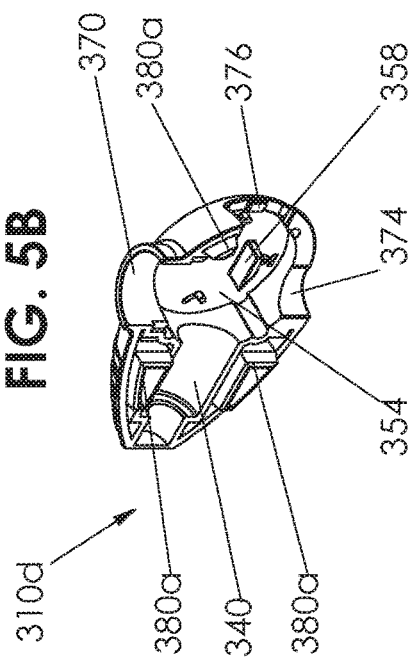

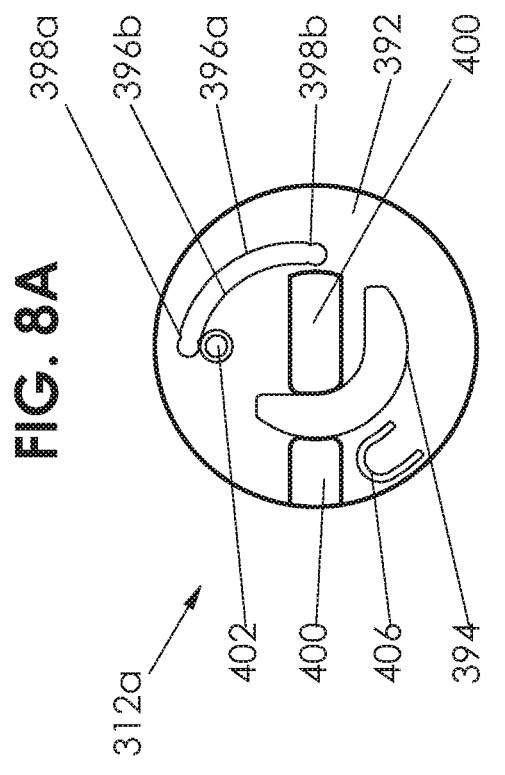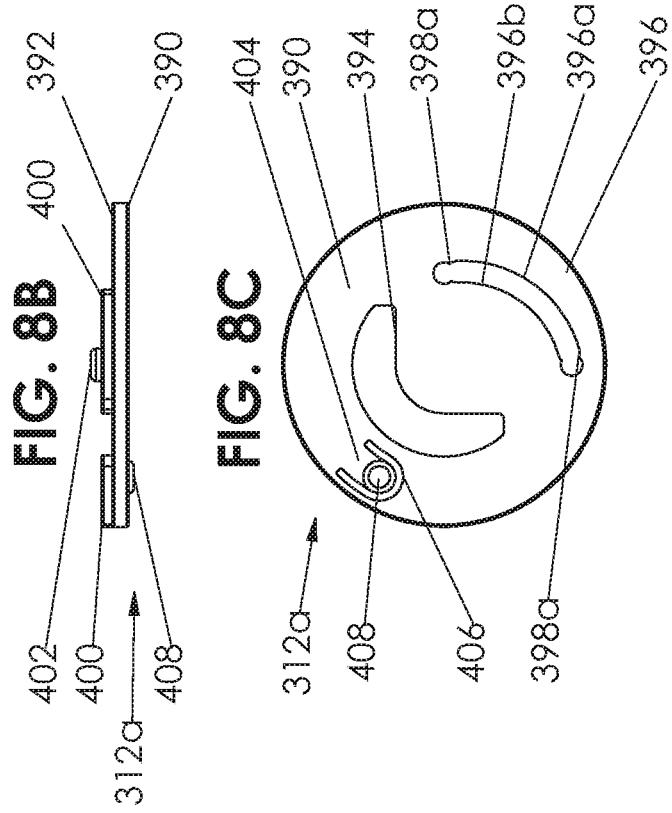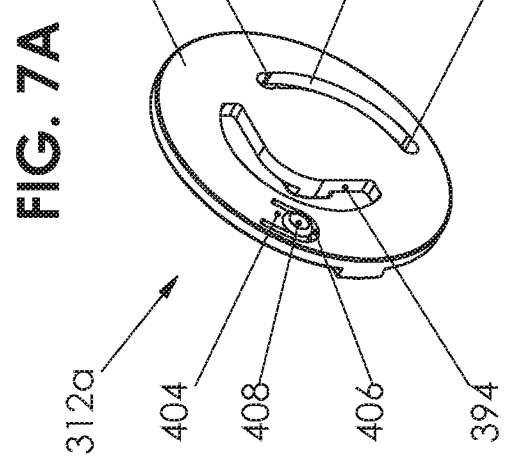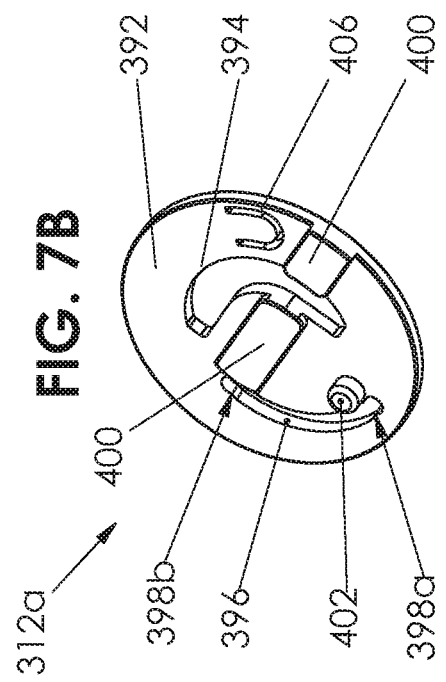

FIG. 10A
FIG. 10B
FIG. 10C
FIG. 9A
FIG. 9B

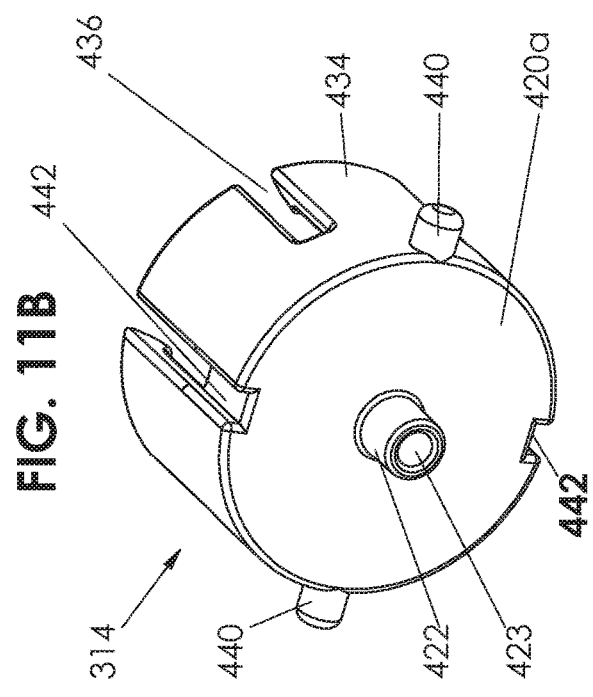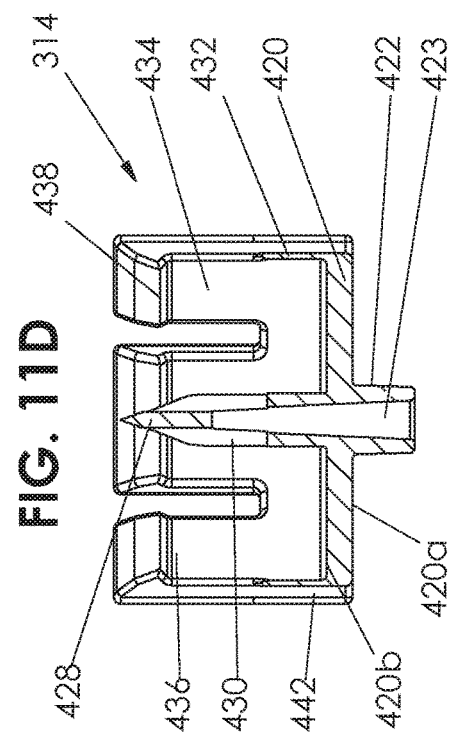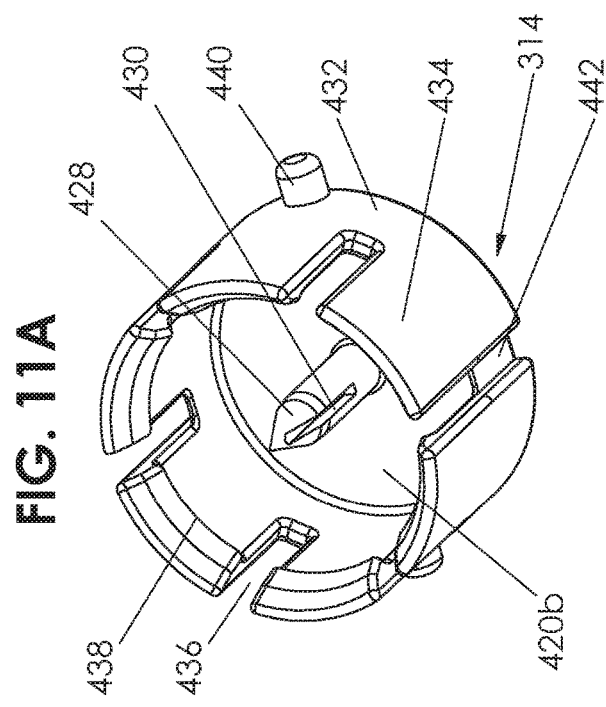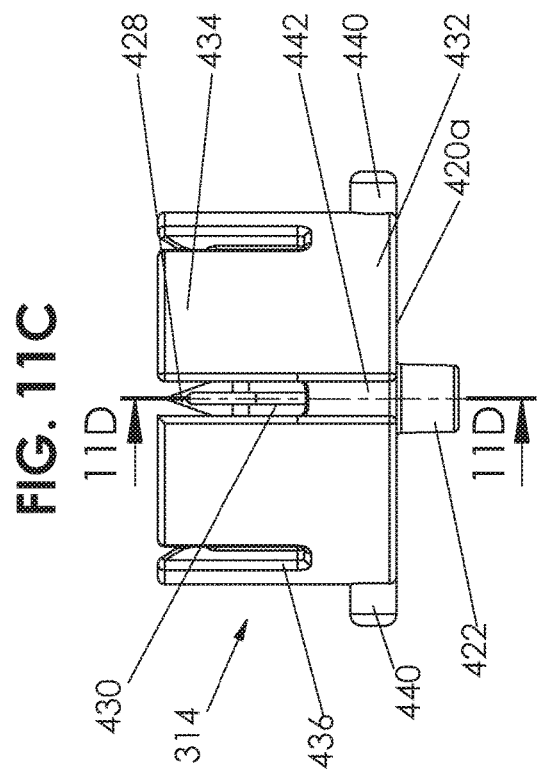

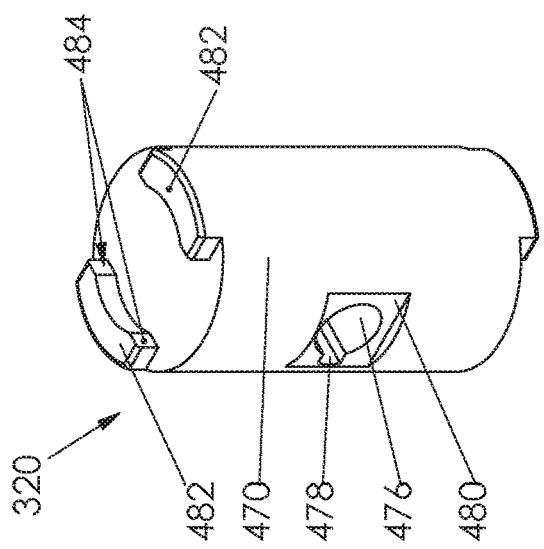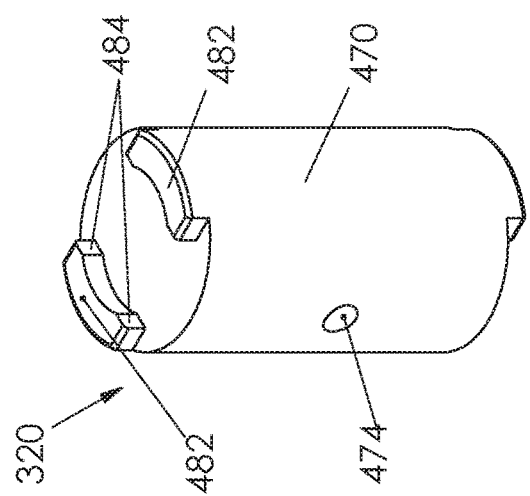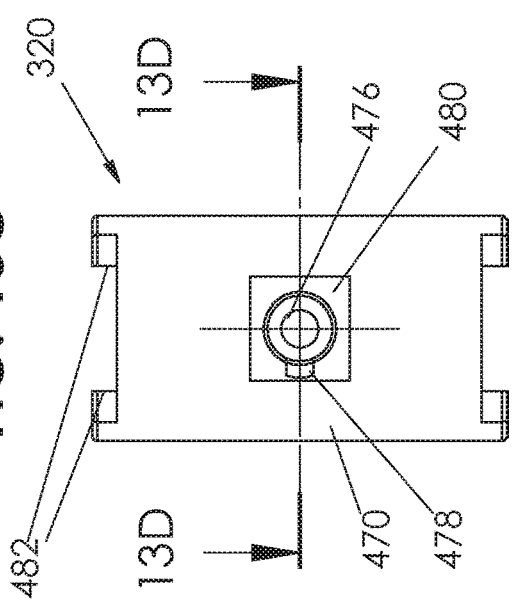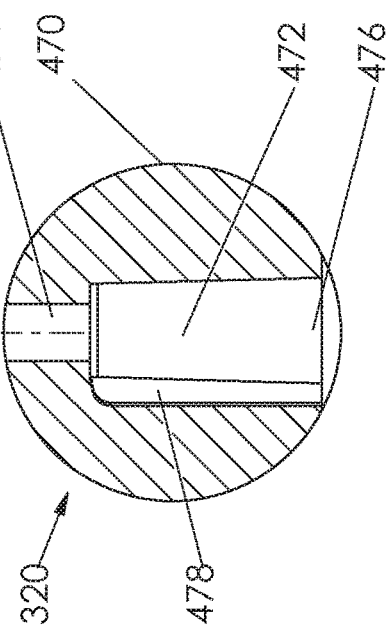

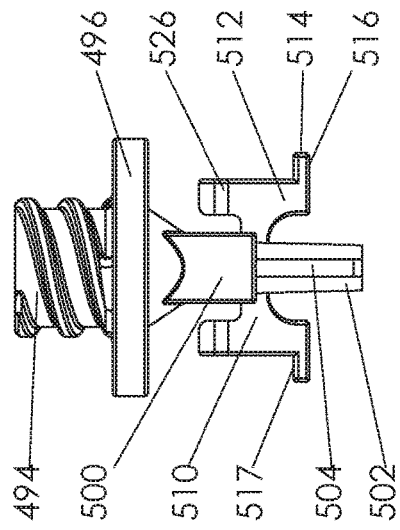
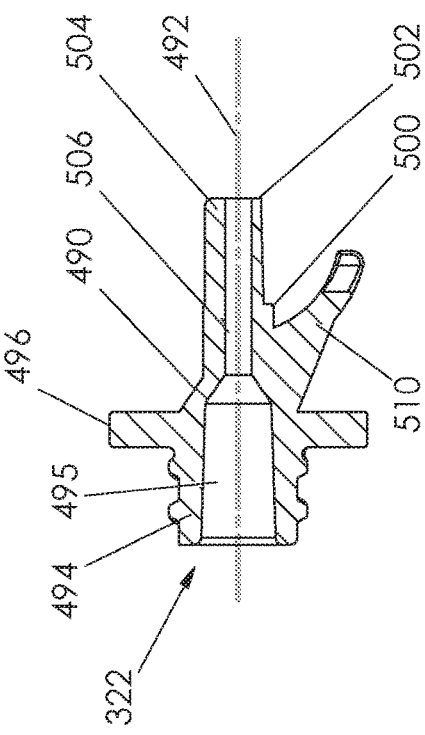
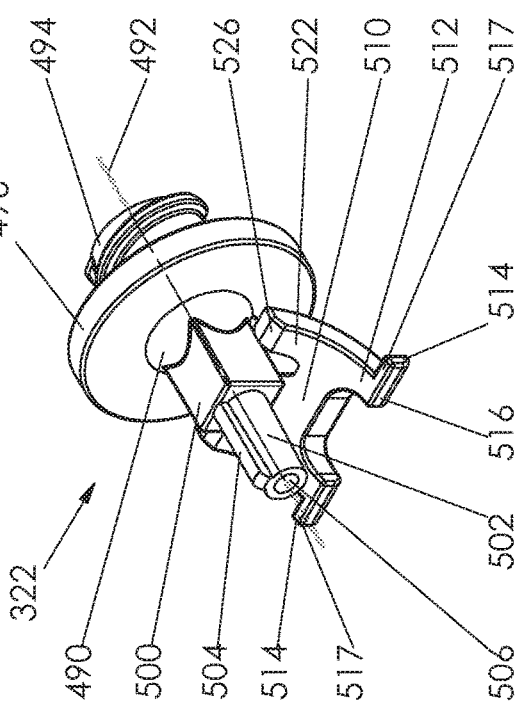
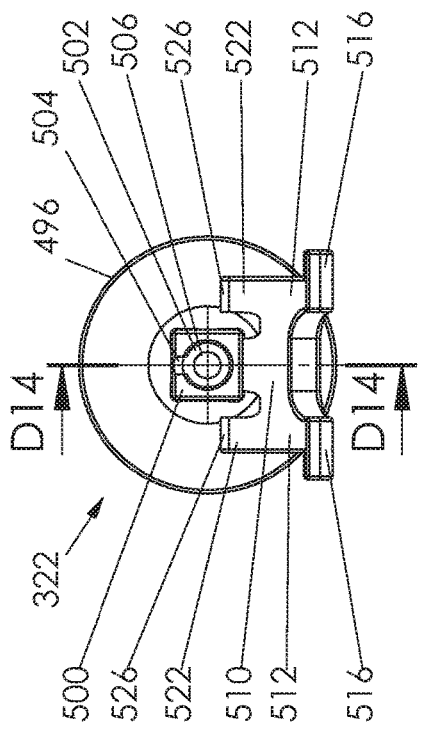

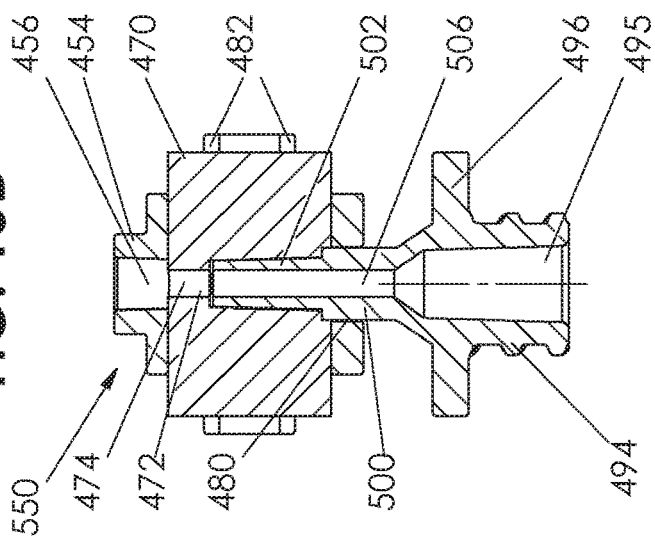
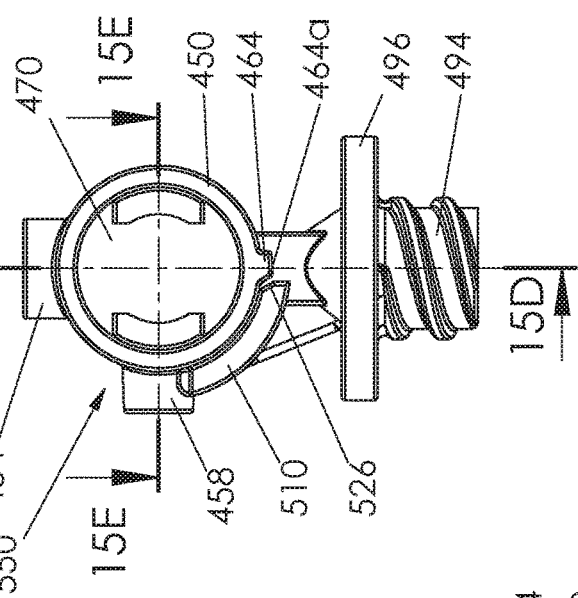
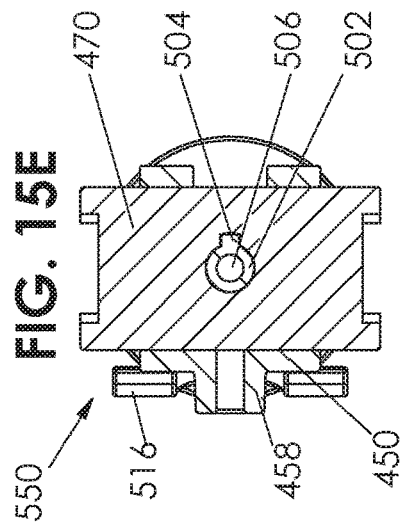
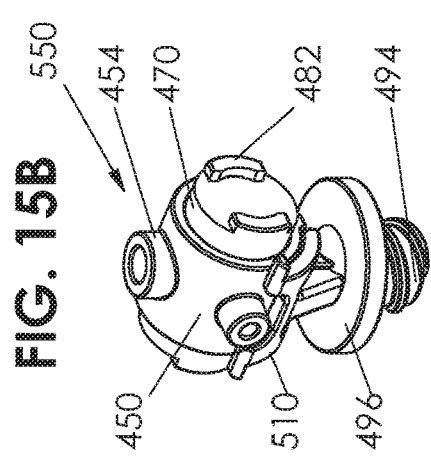
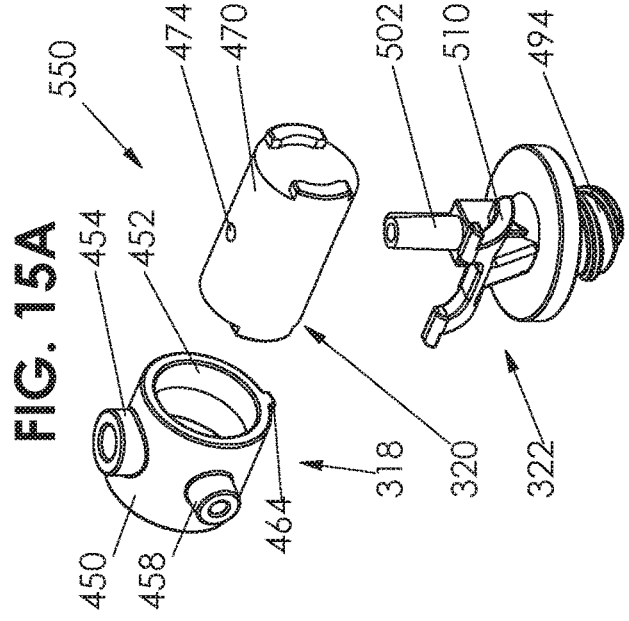

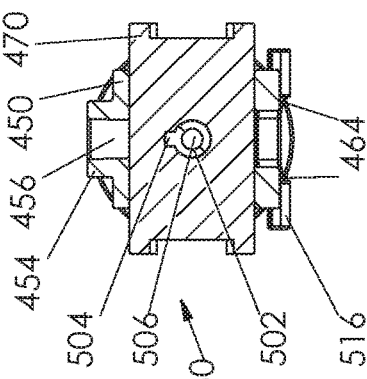
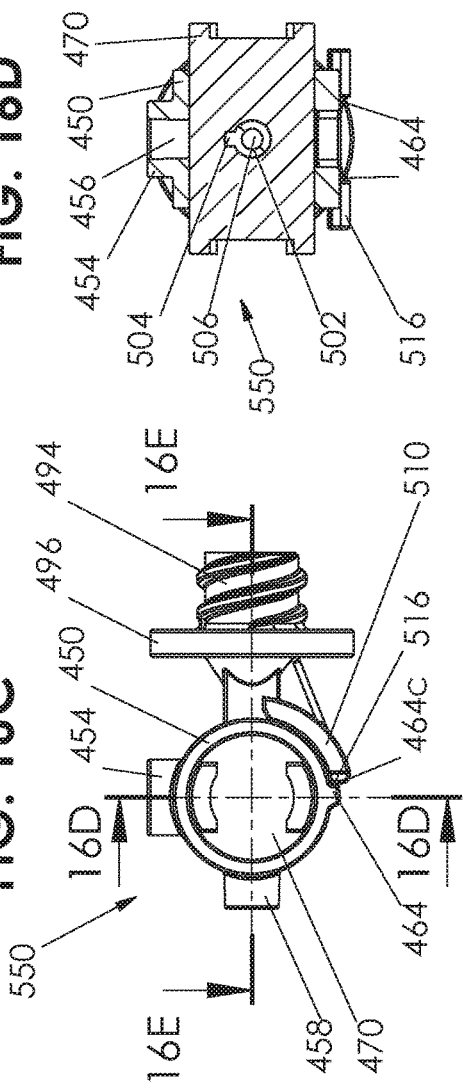
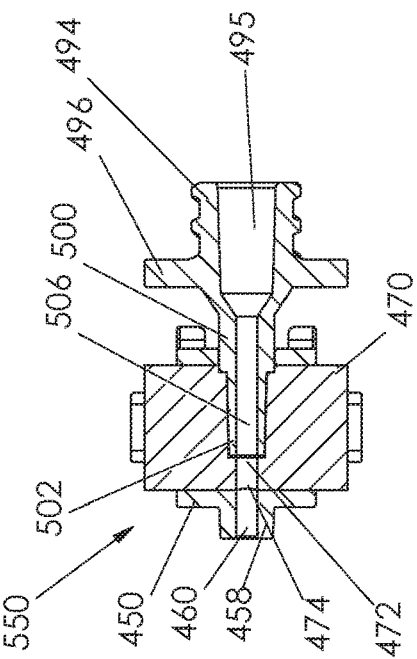
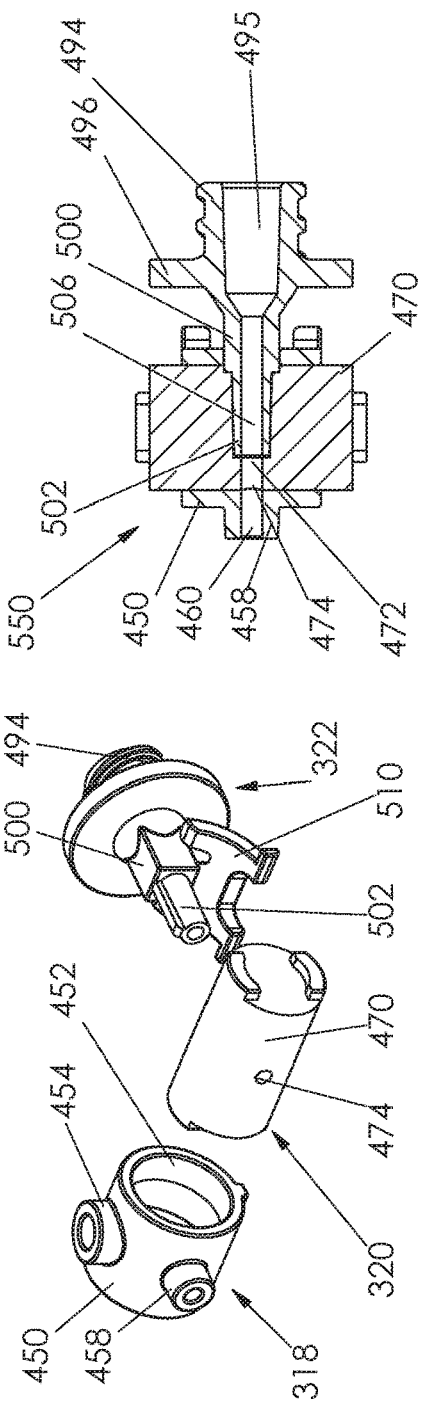
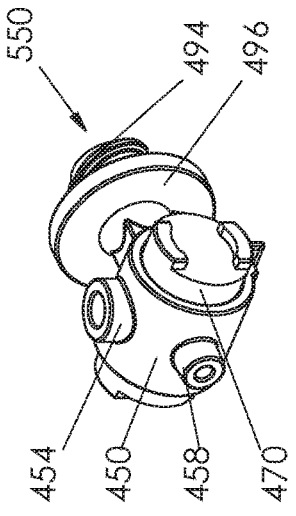

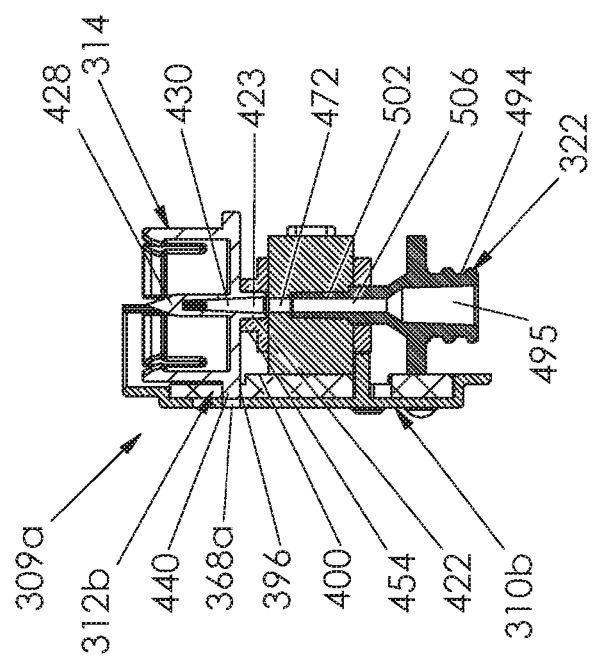
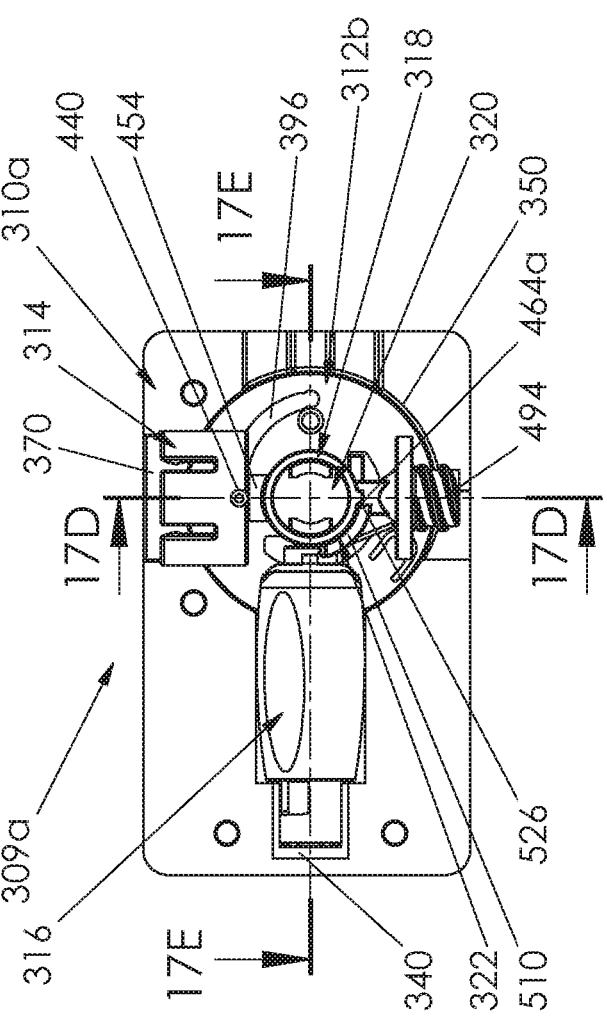
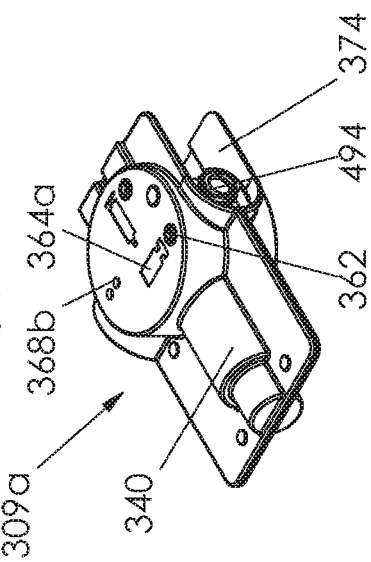
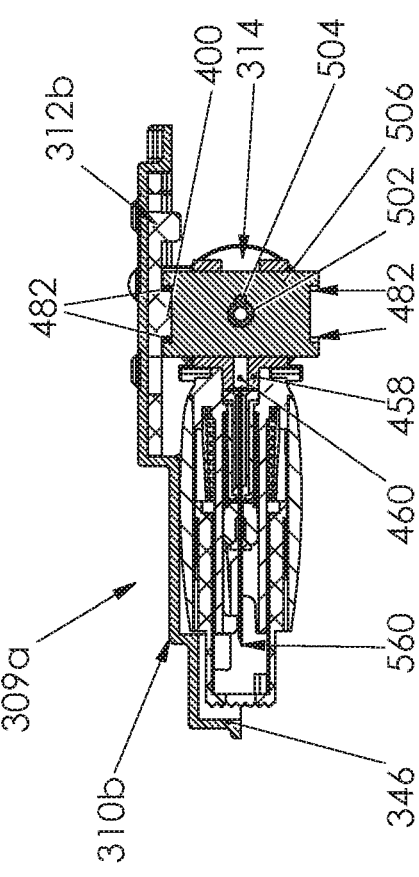

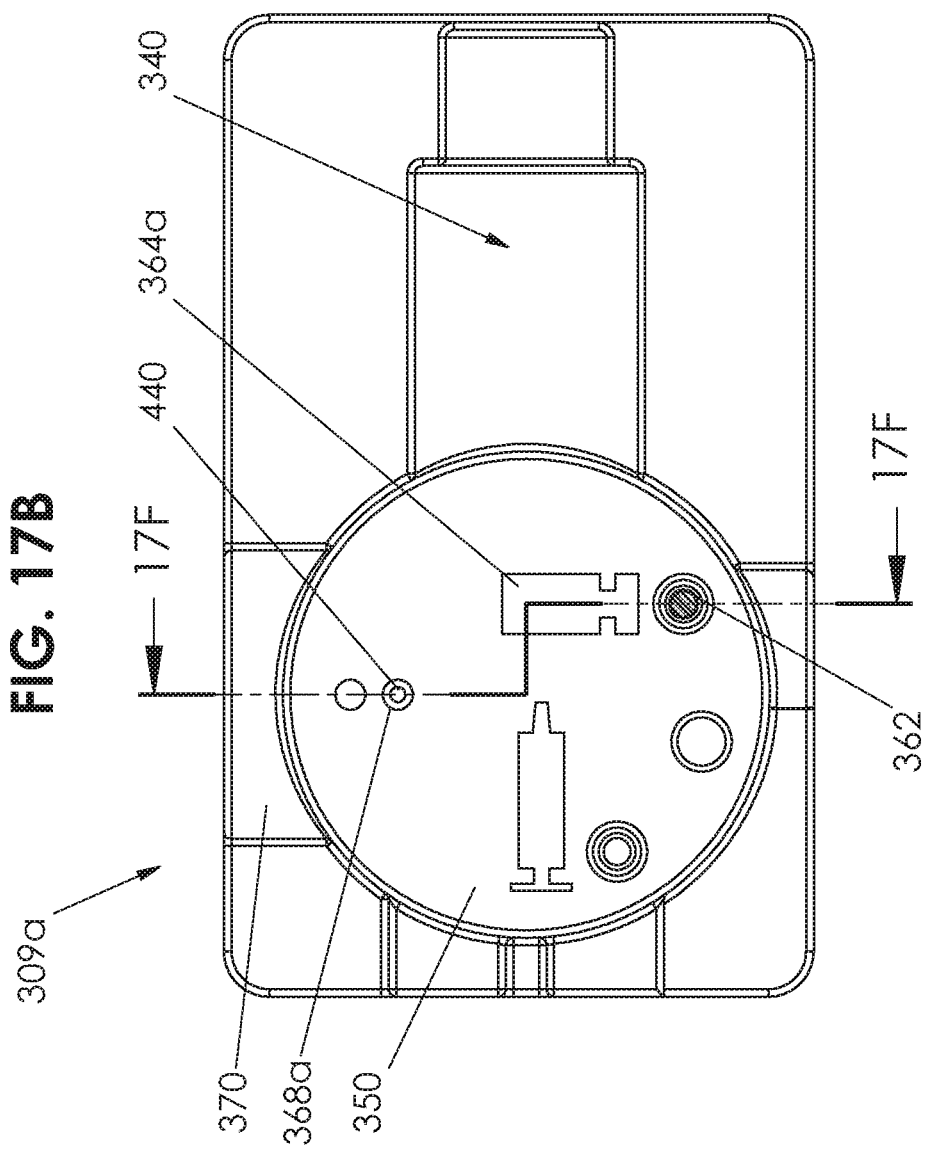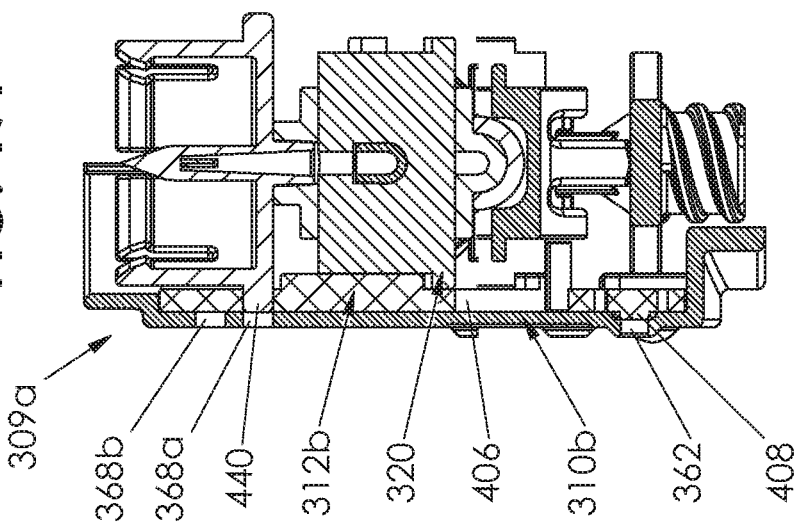

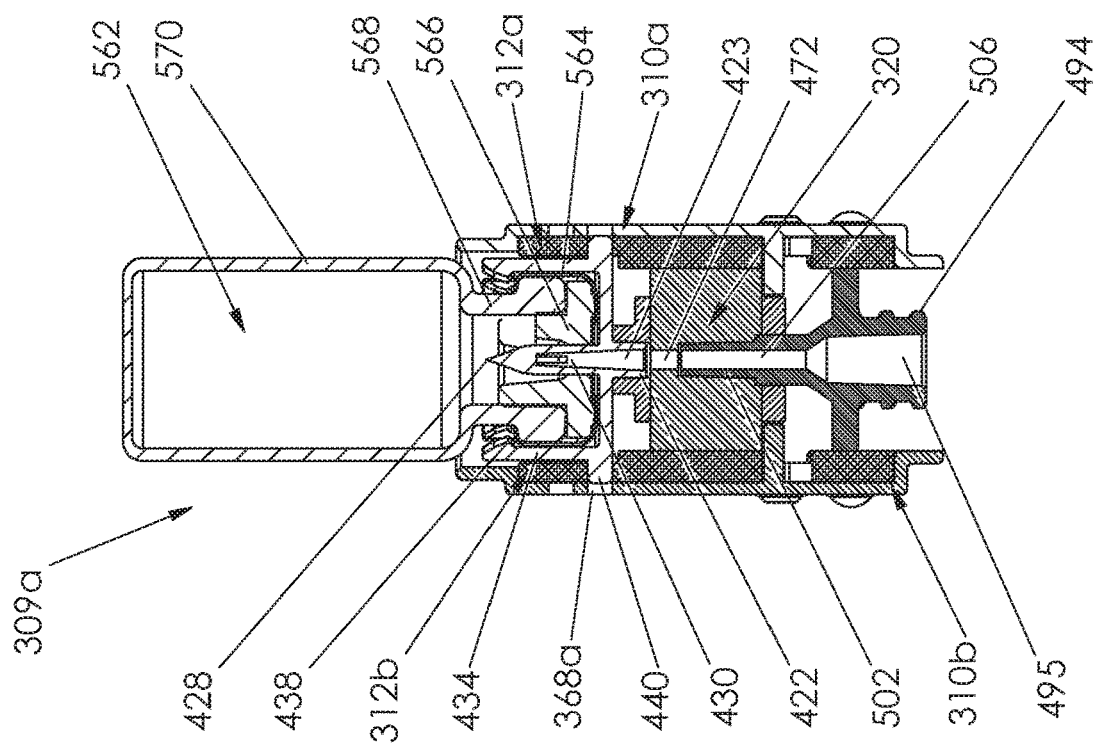
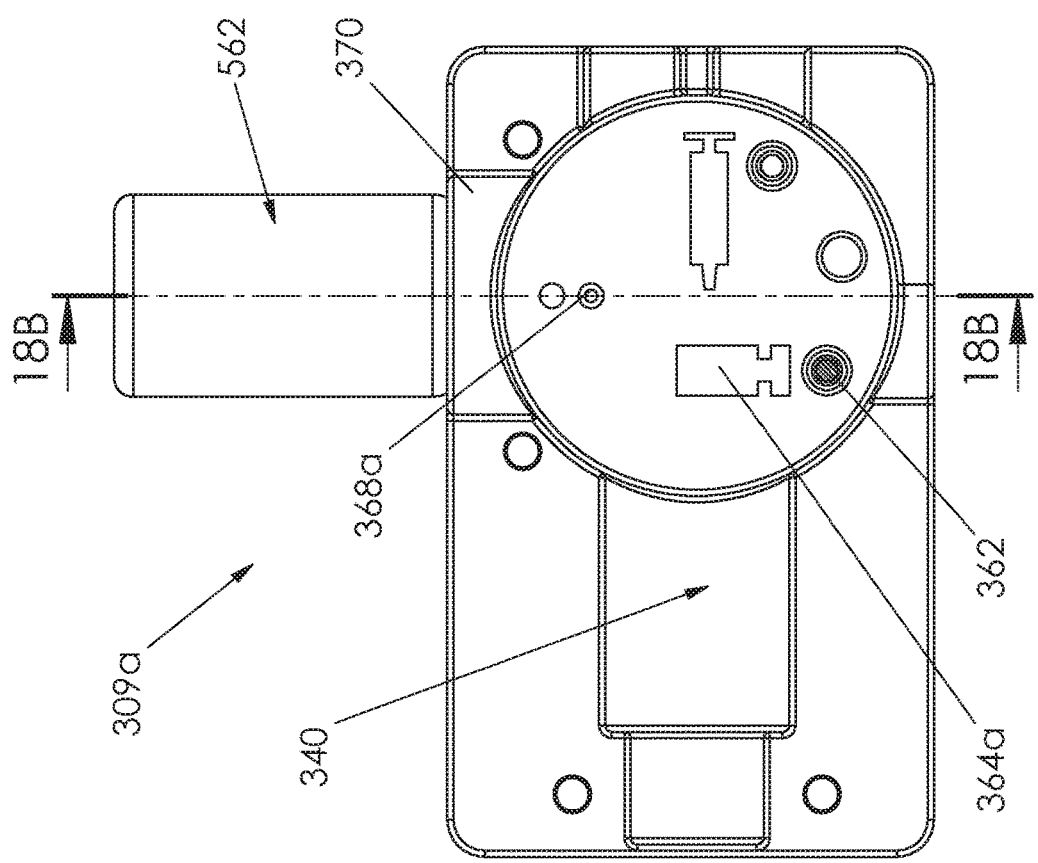

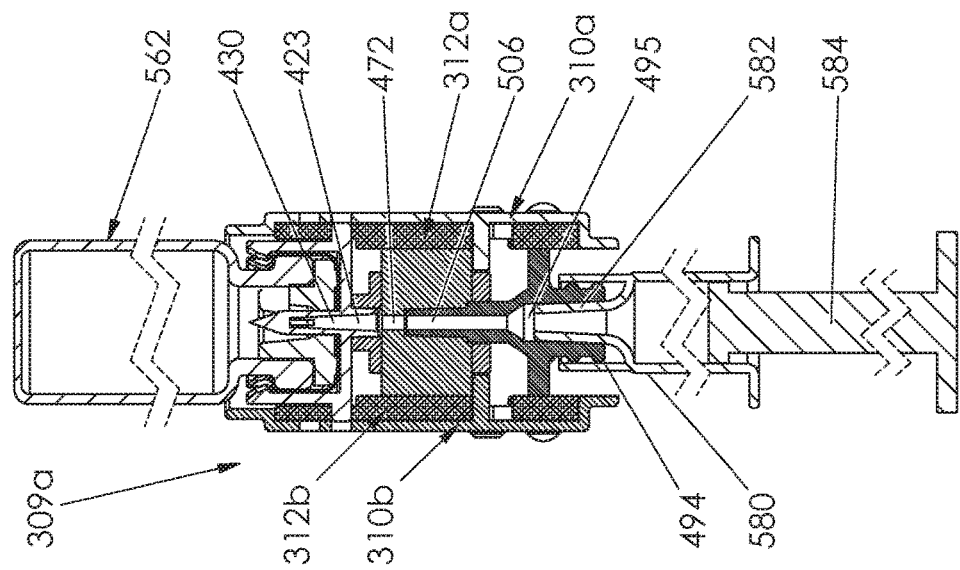
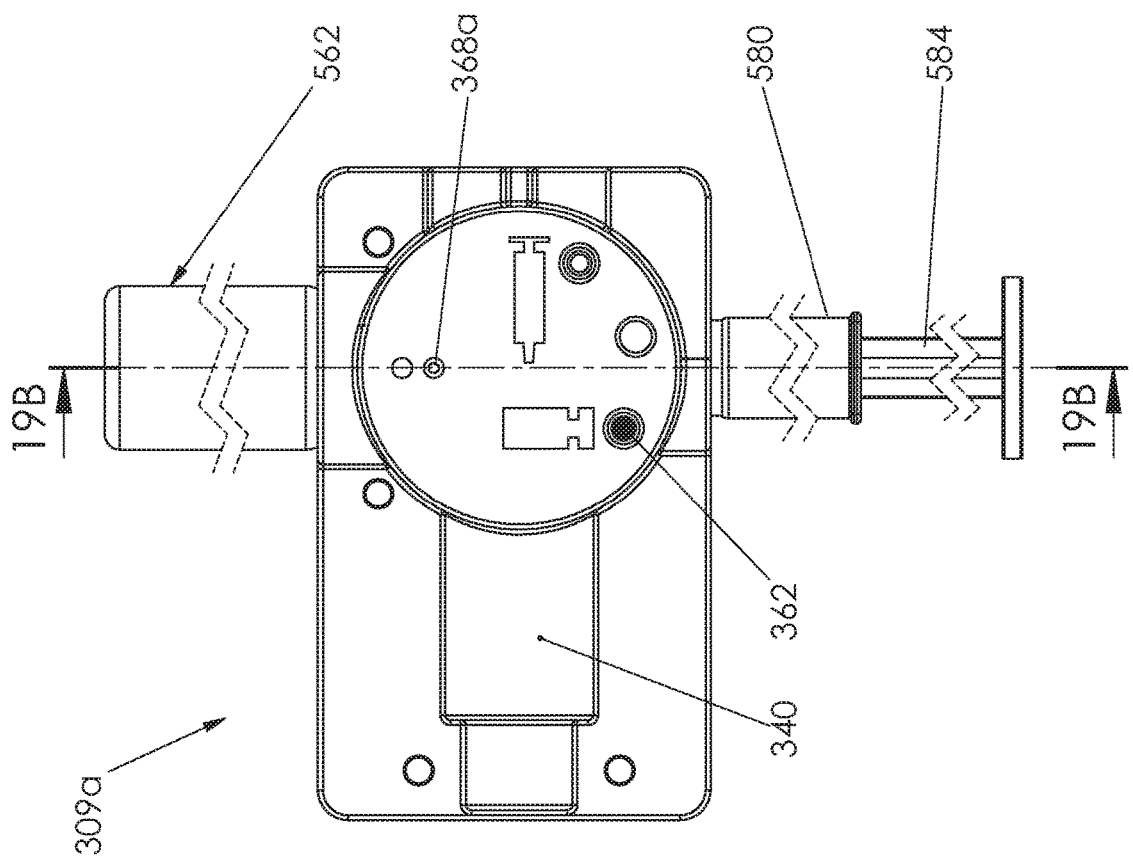

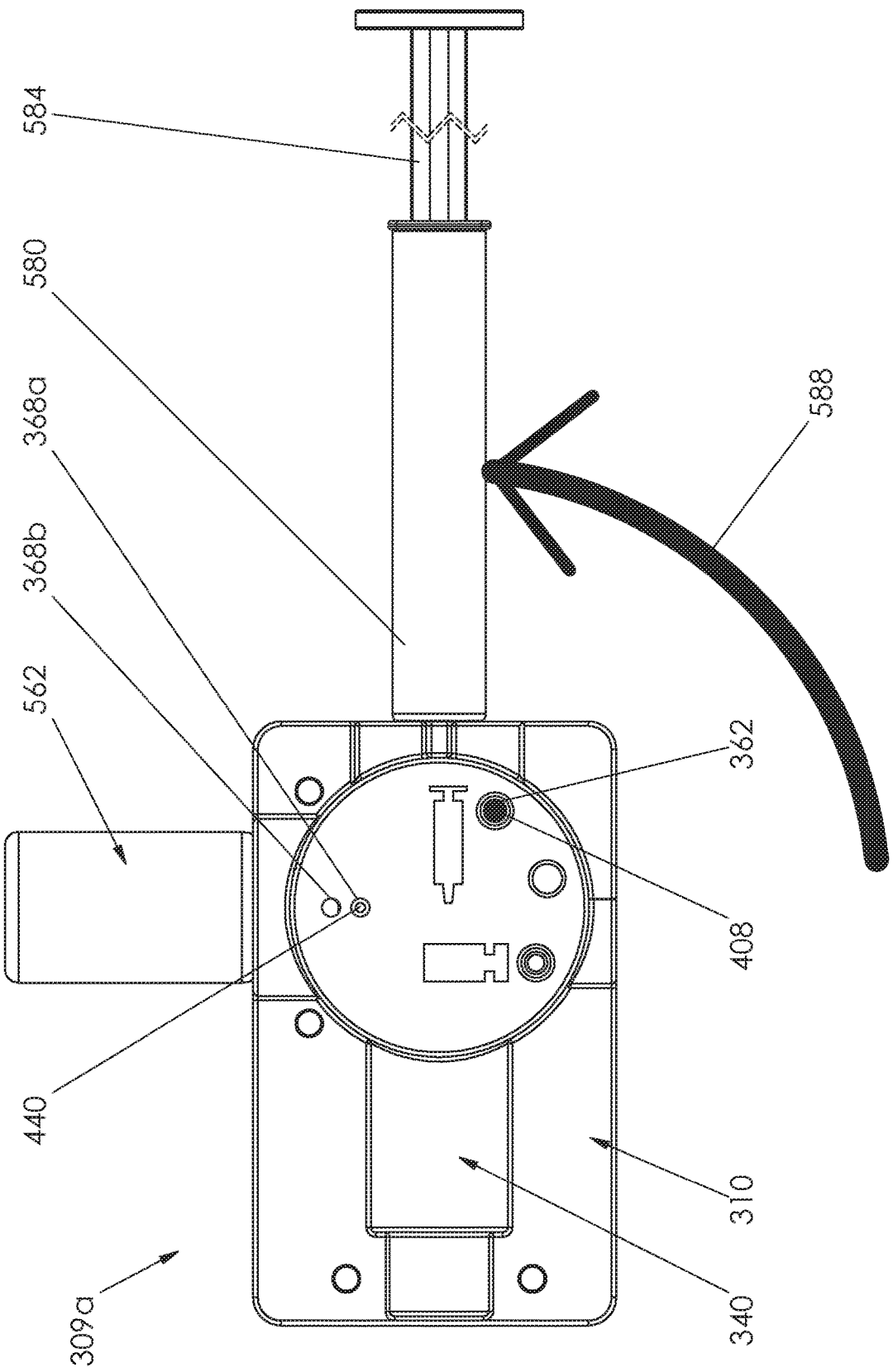

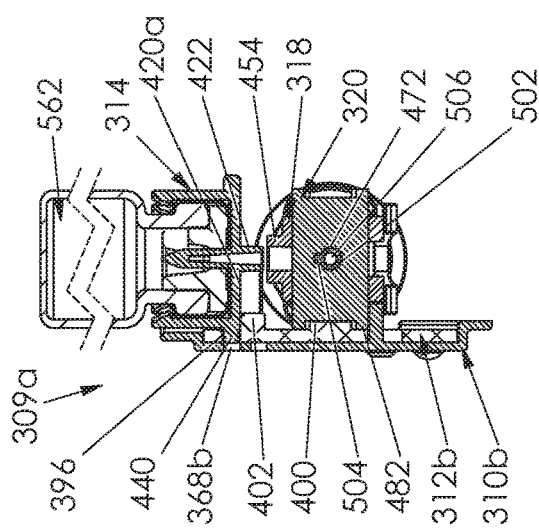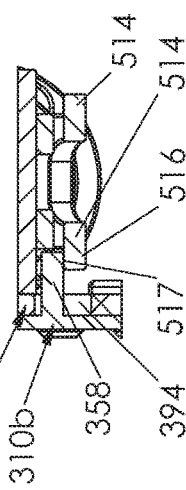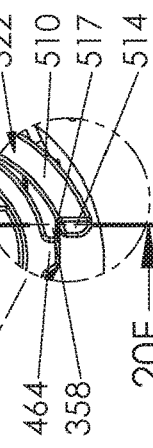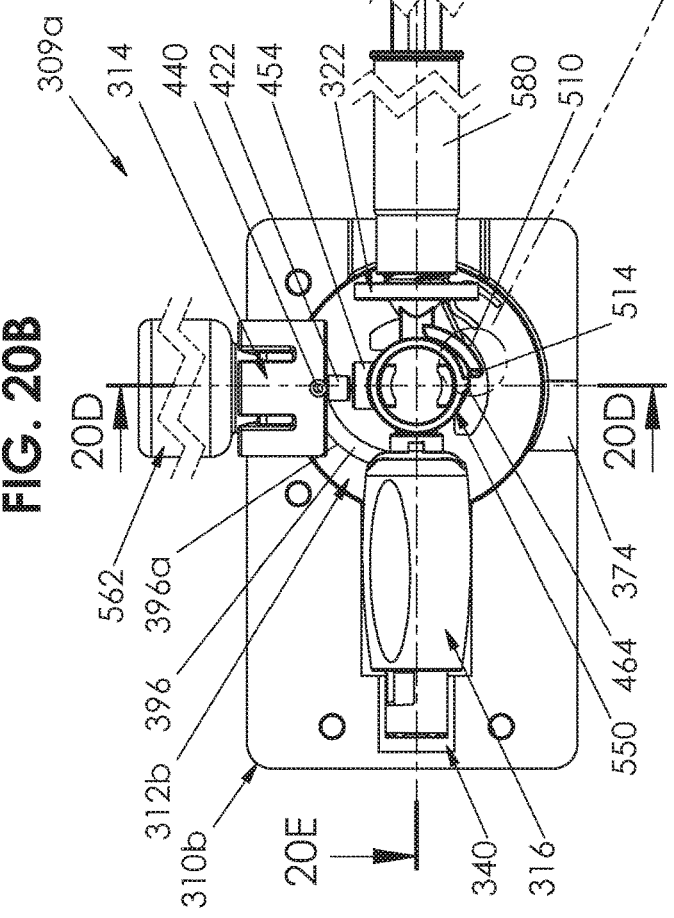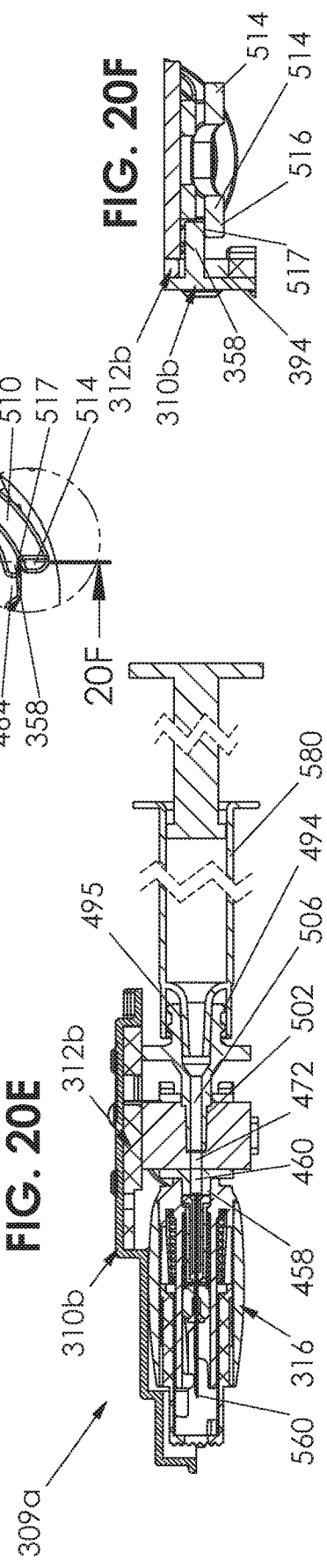

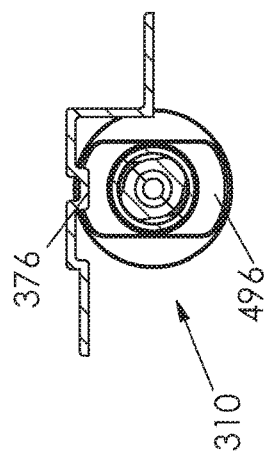
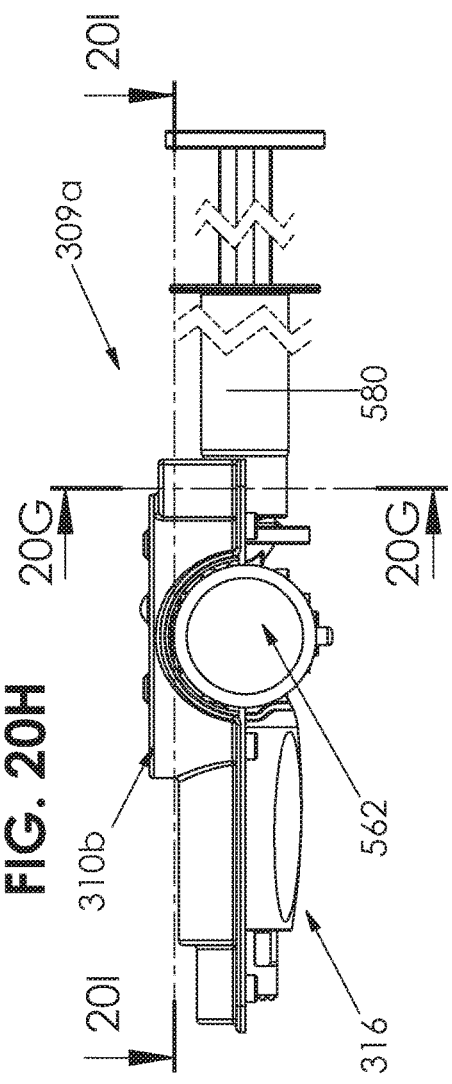
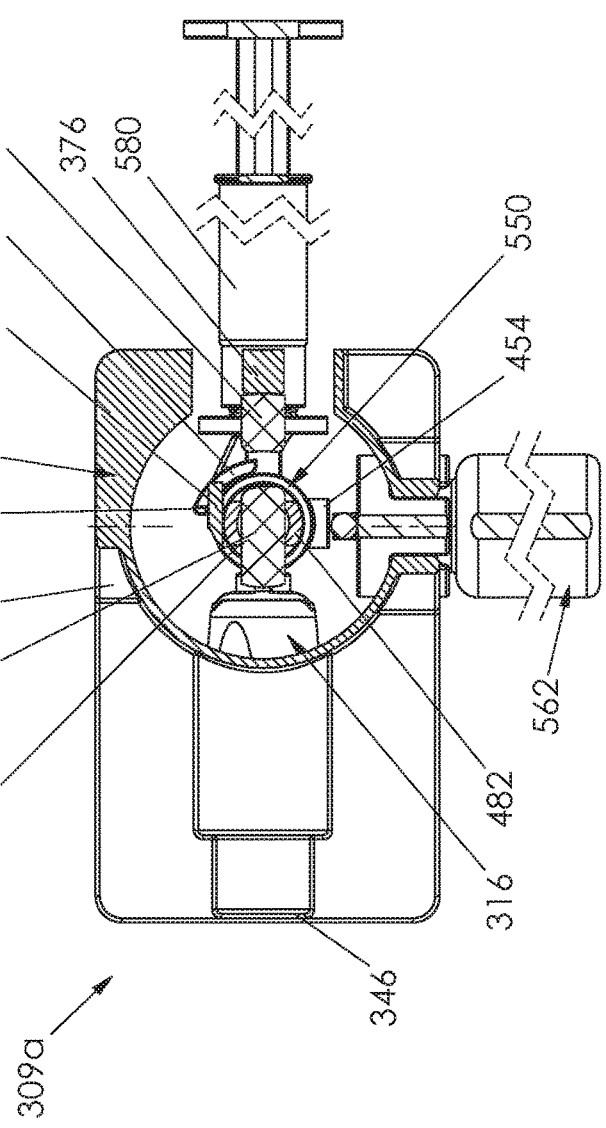

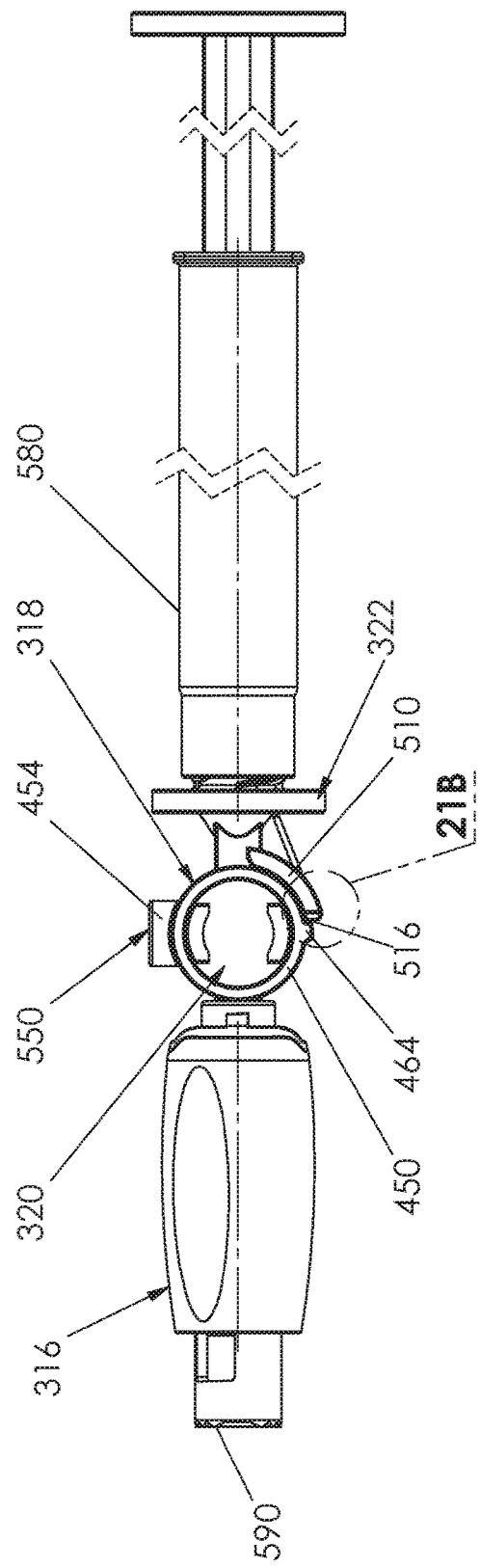
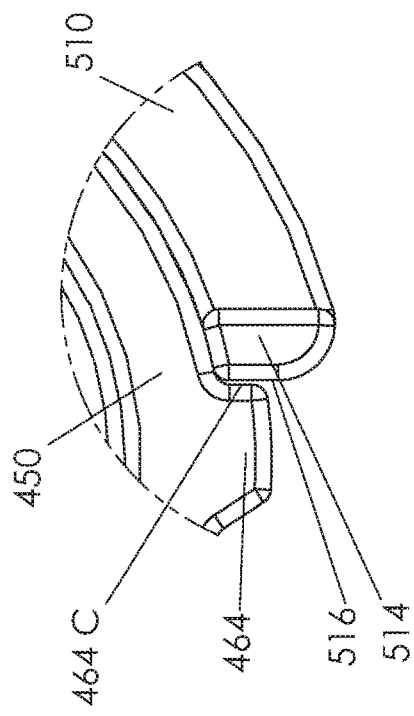

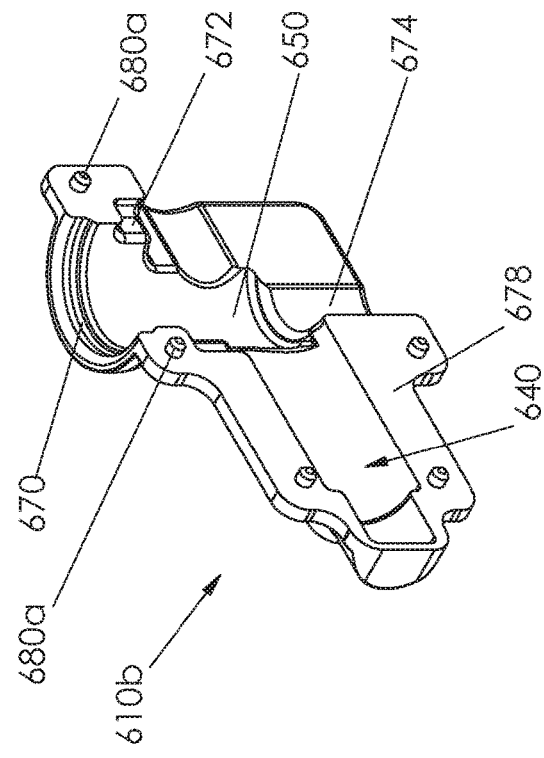
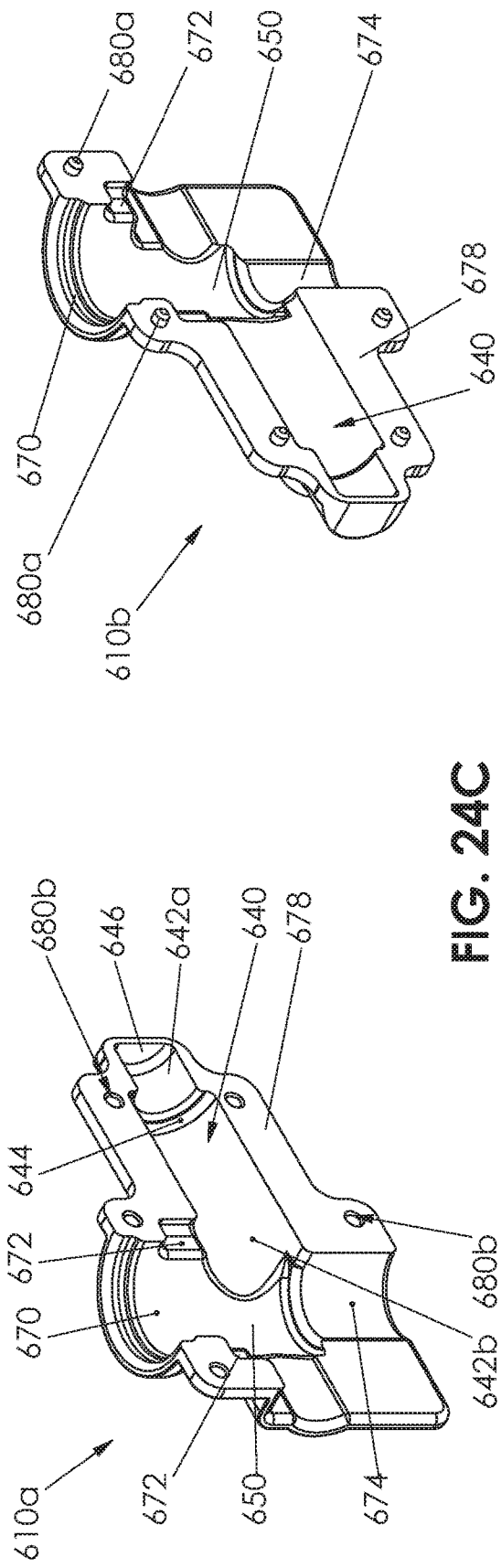
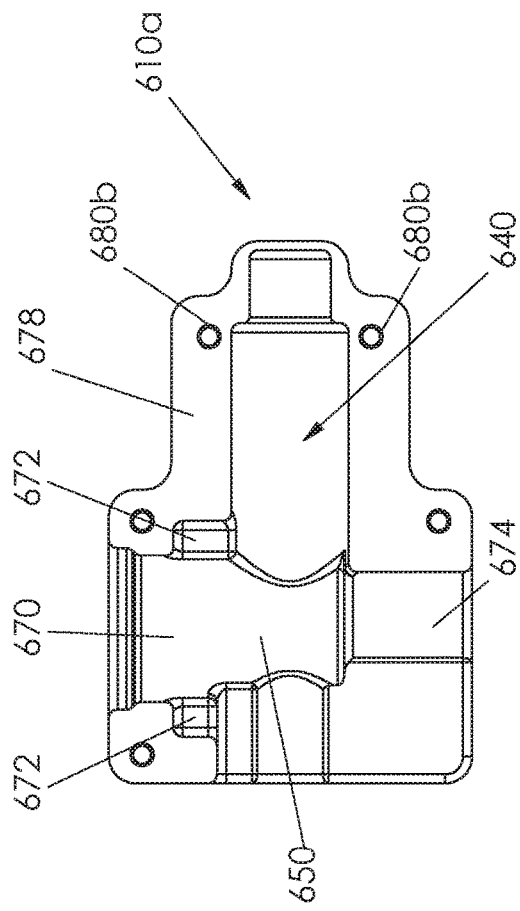

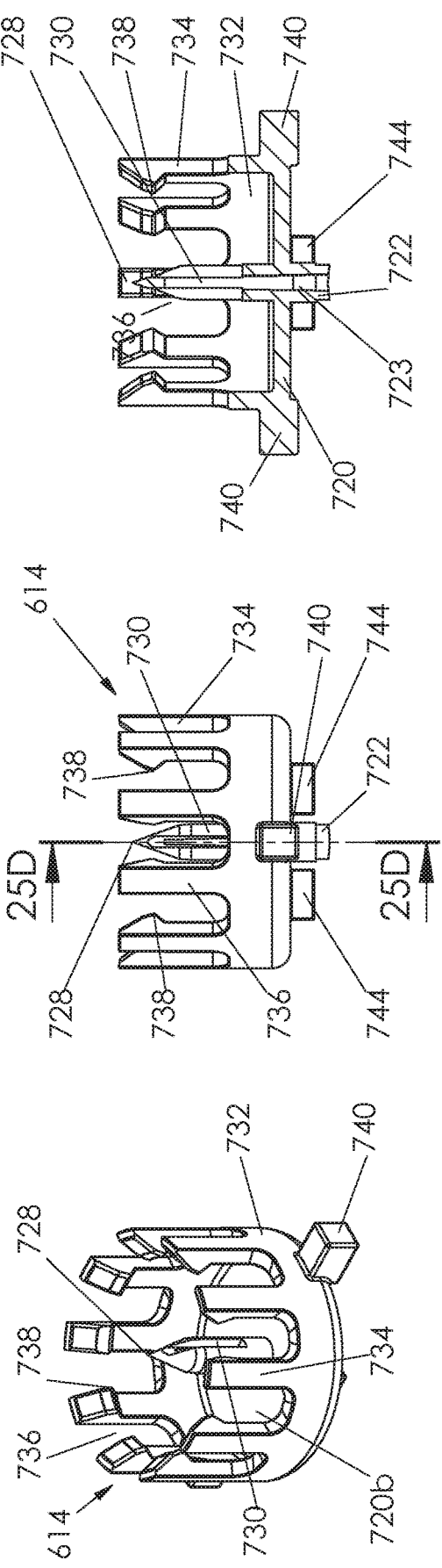

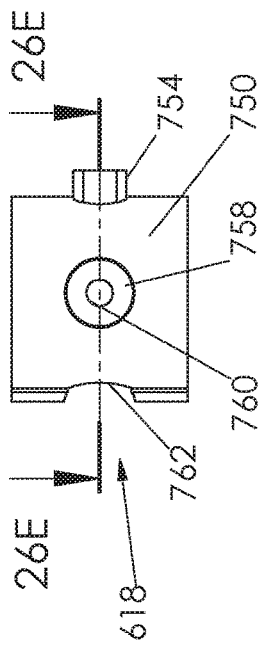
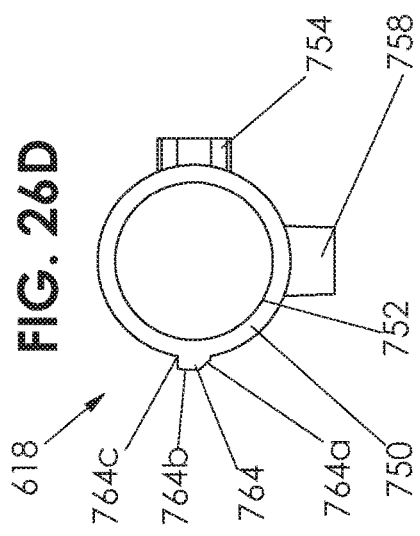
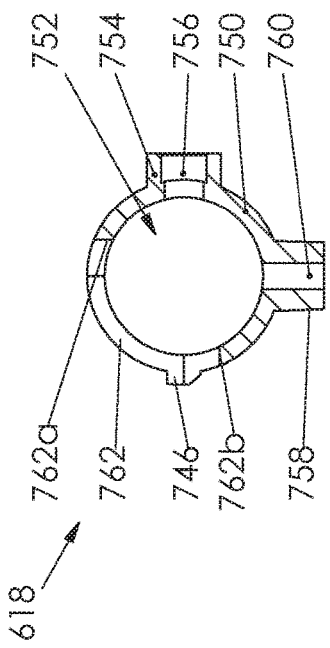
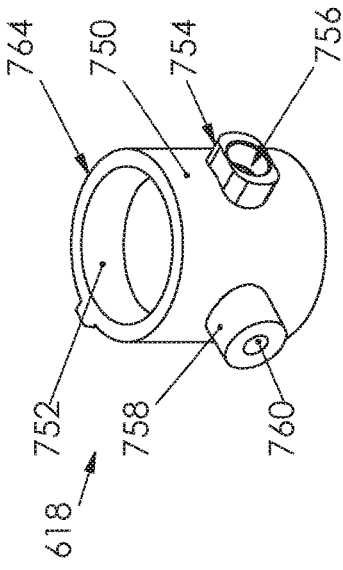
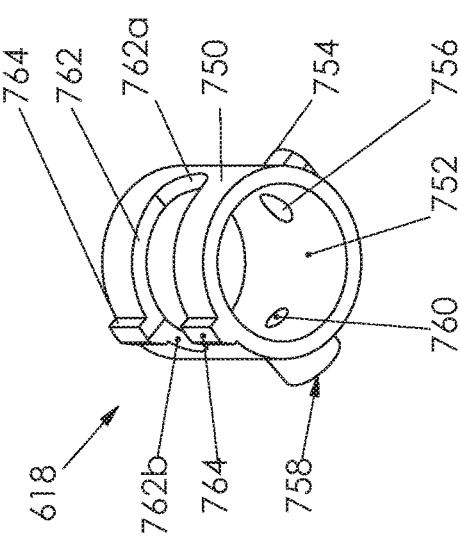

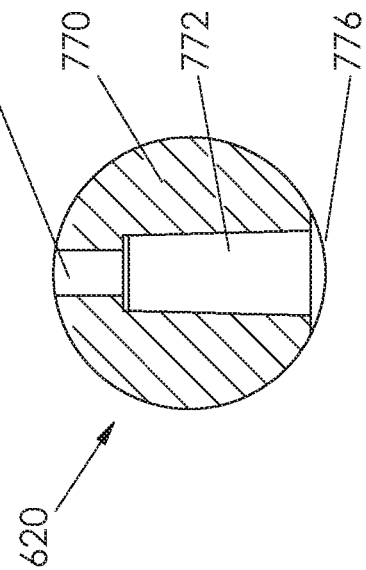
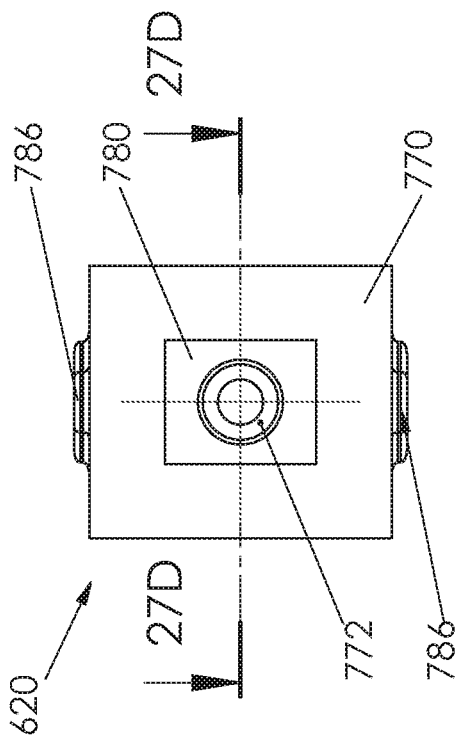
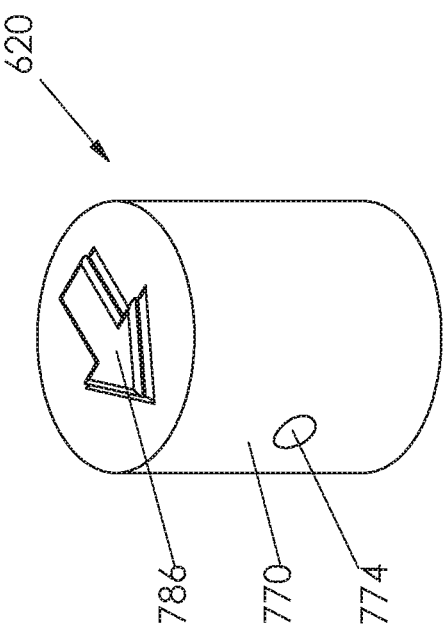
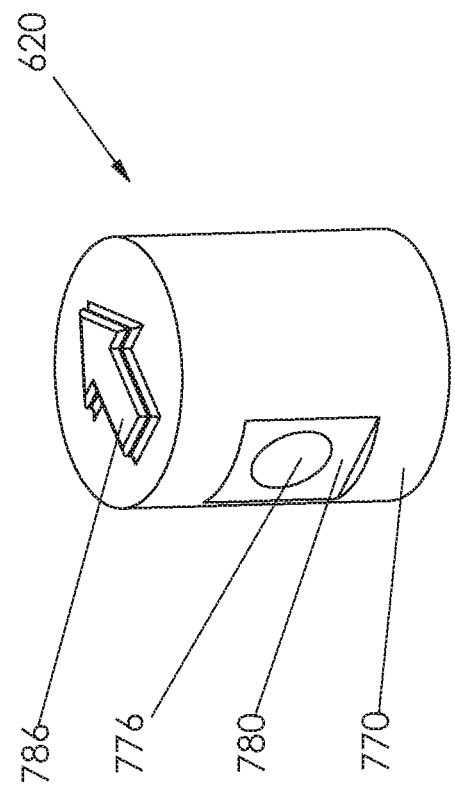

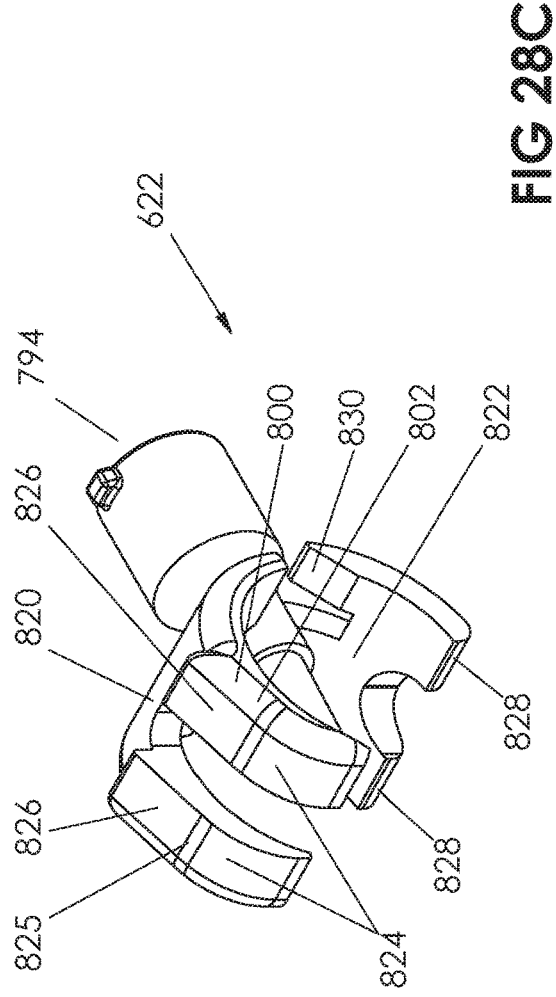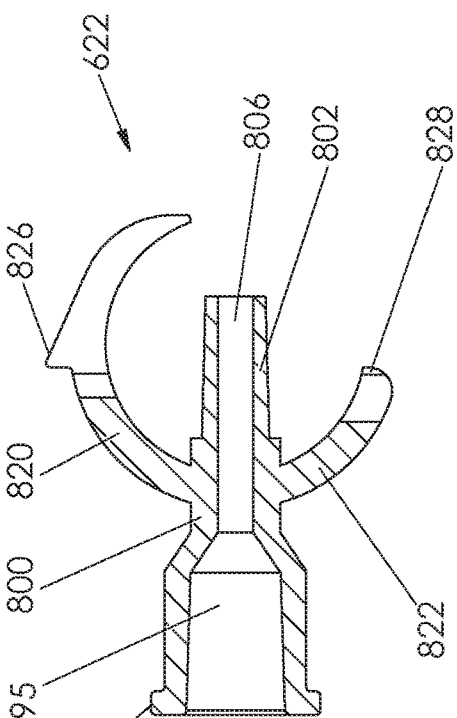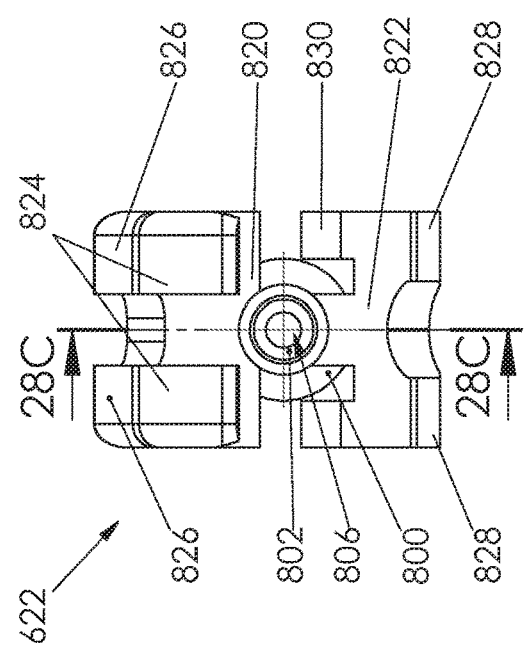

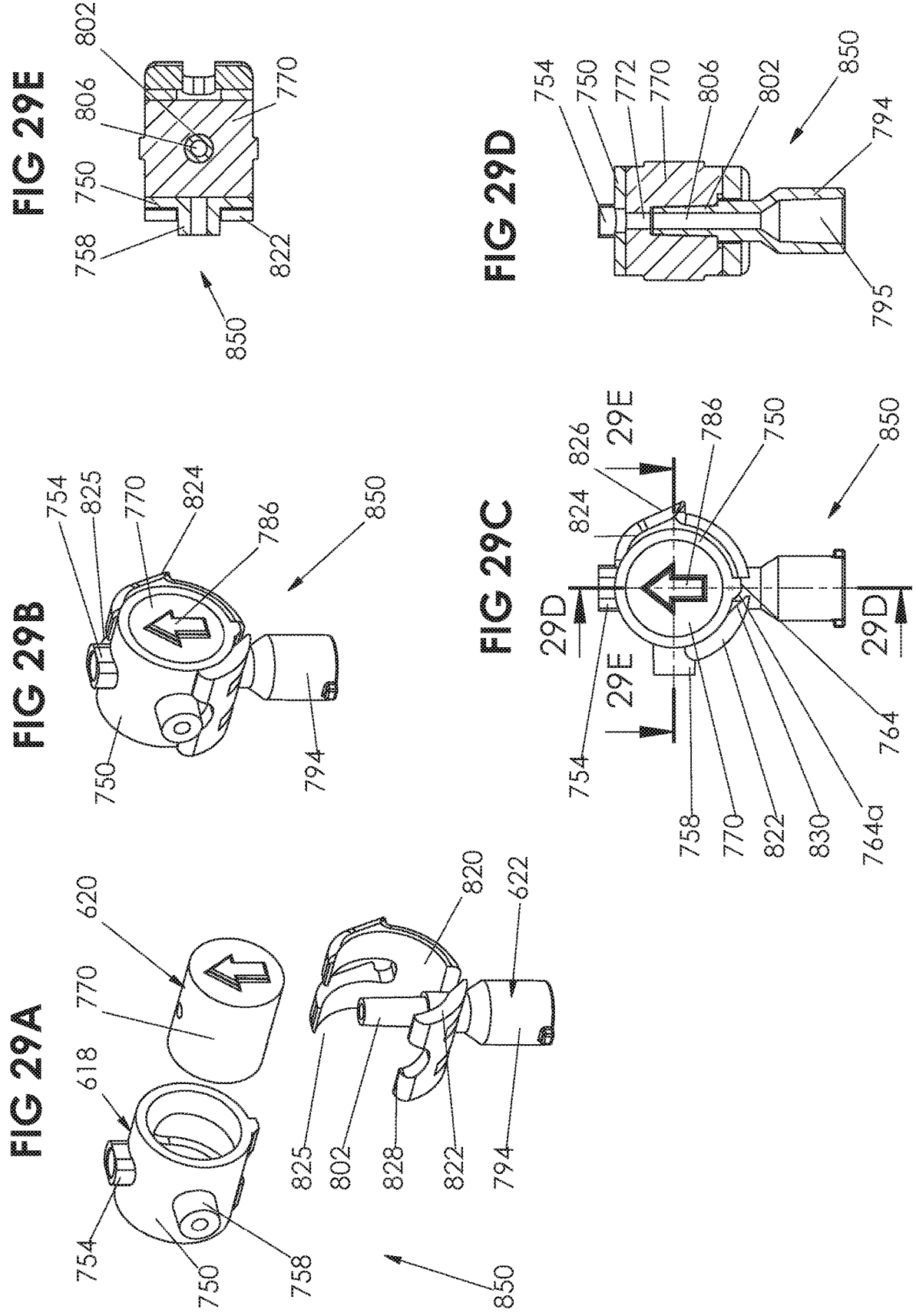

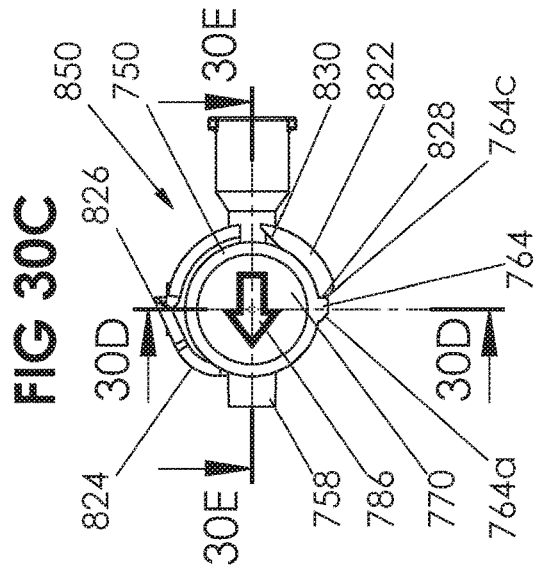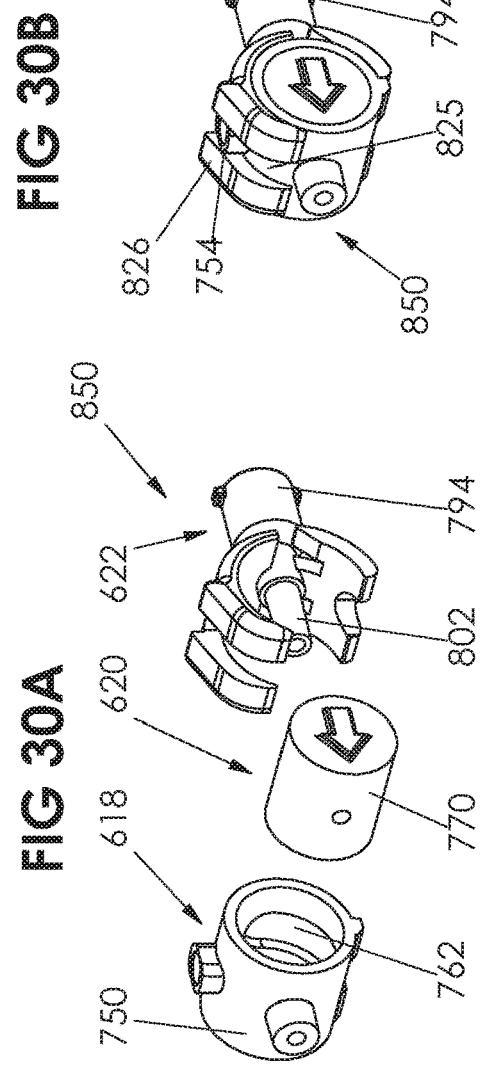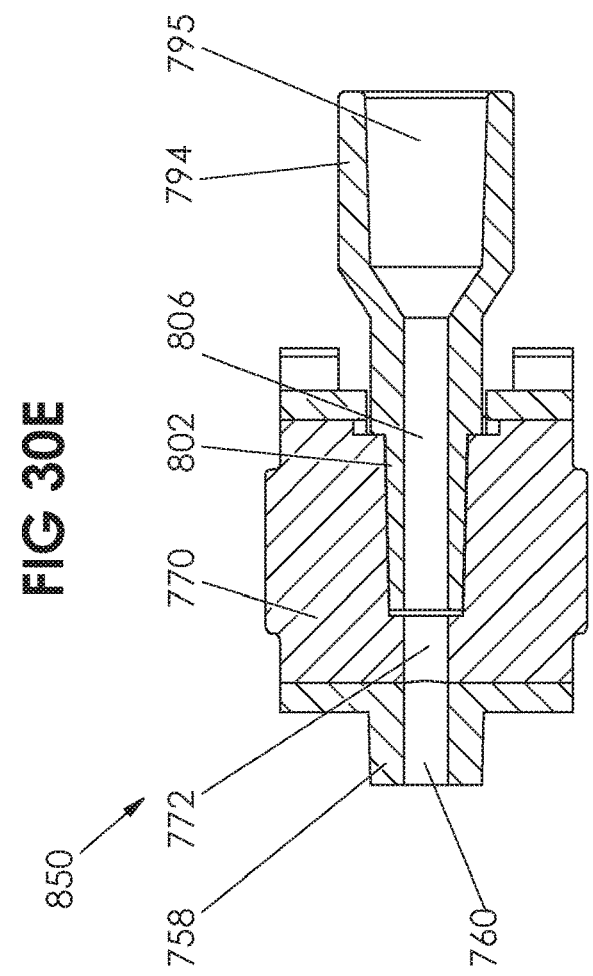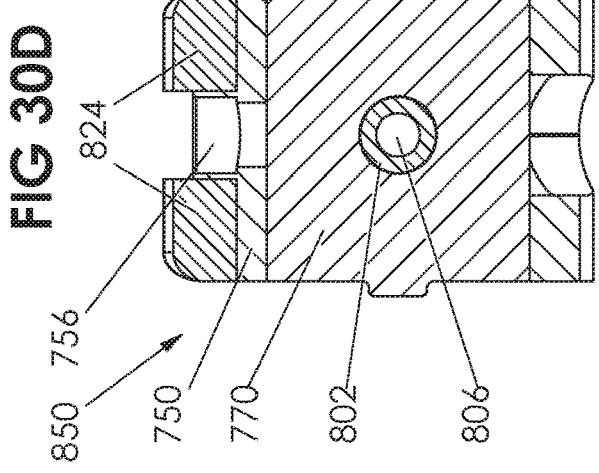

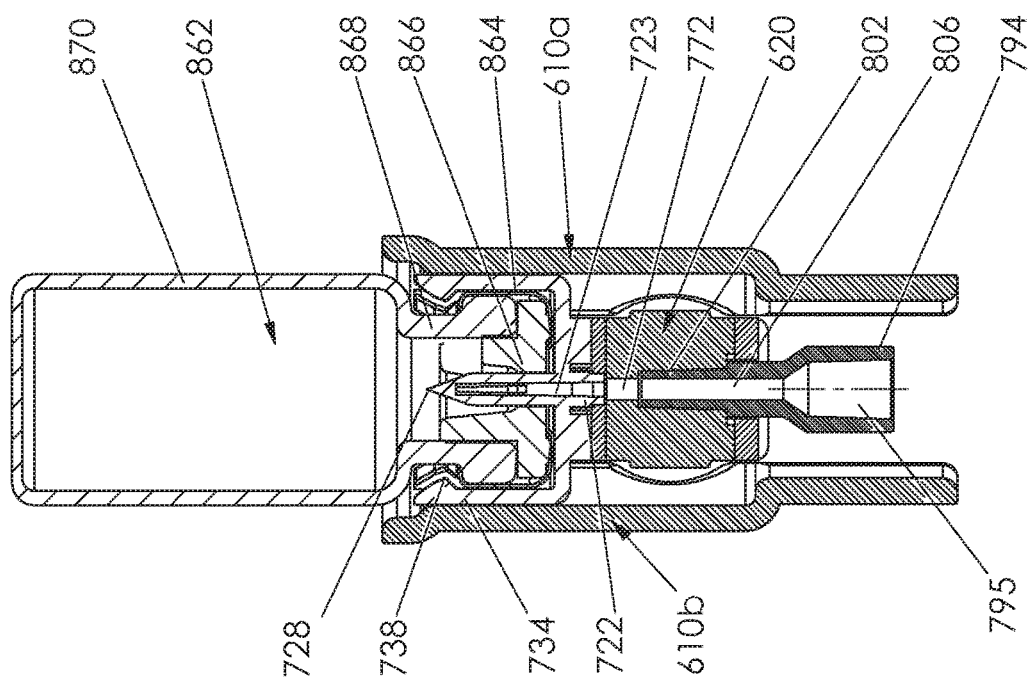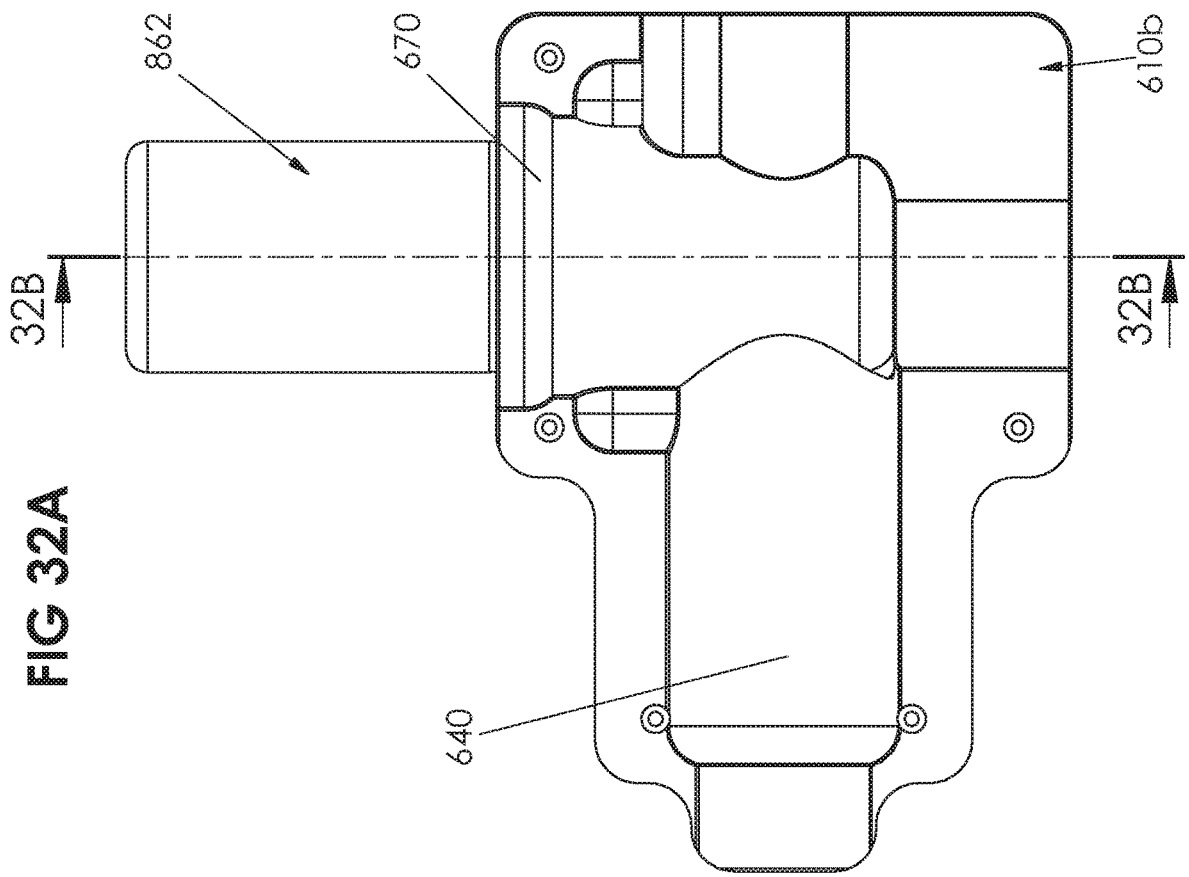

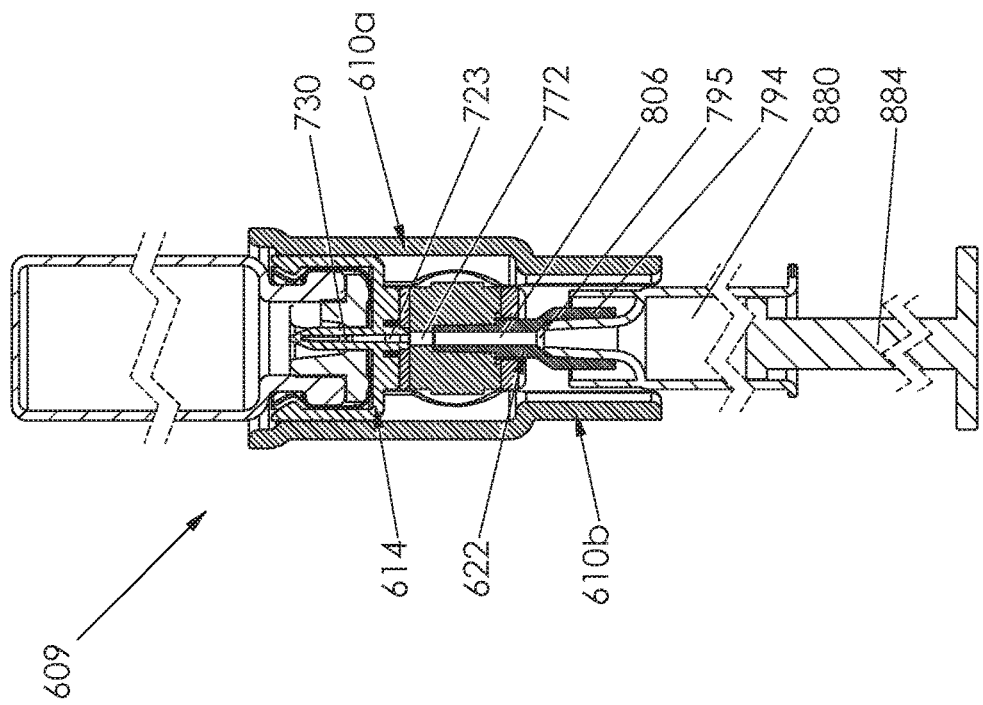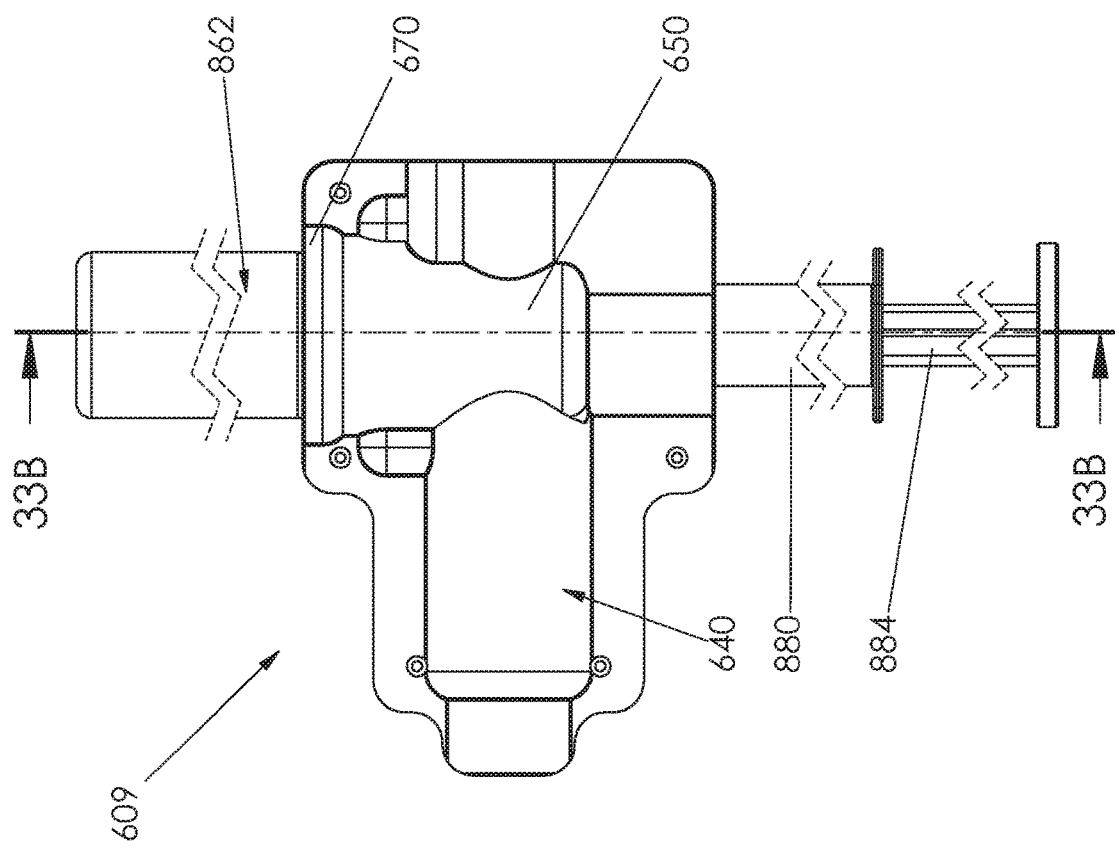

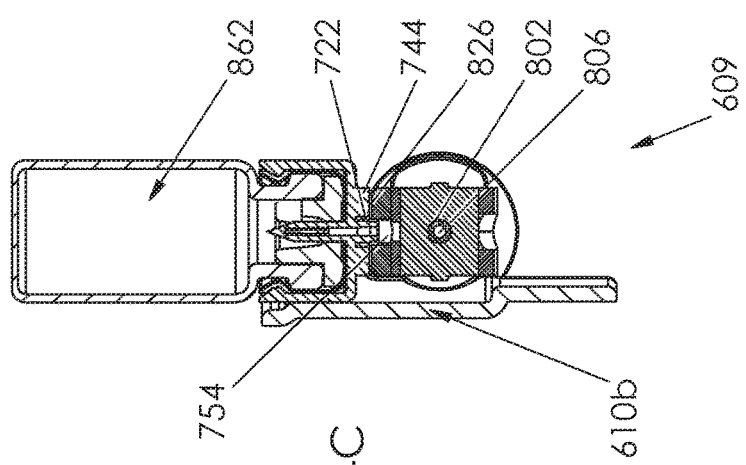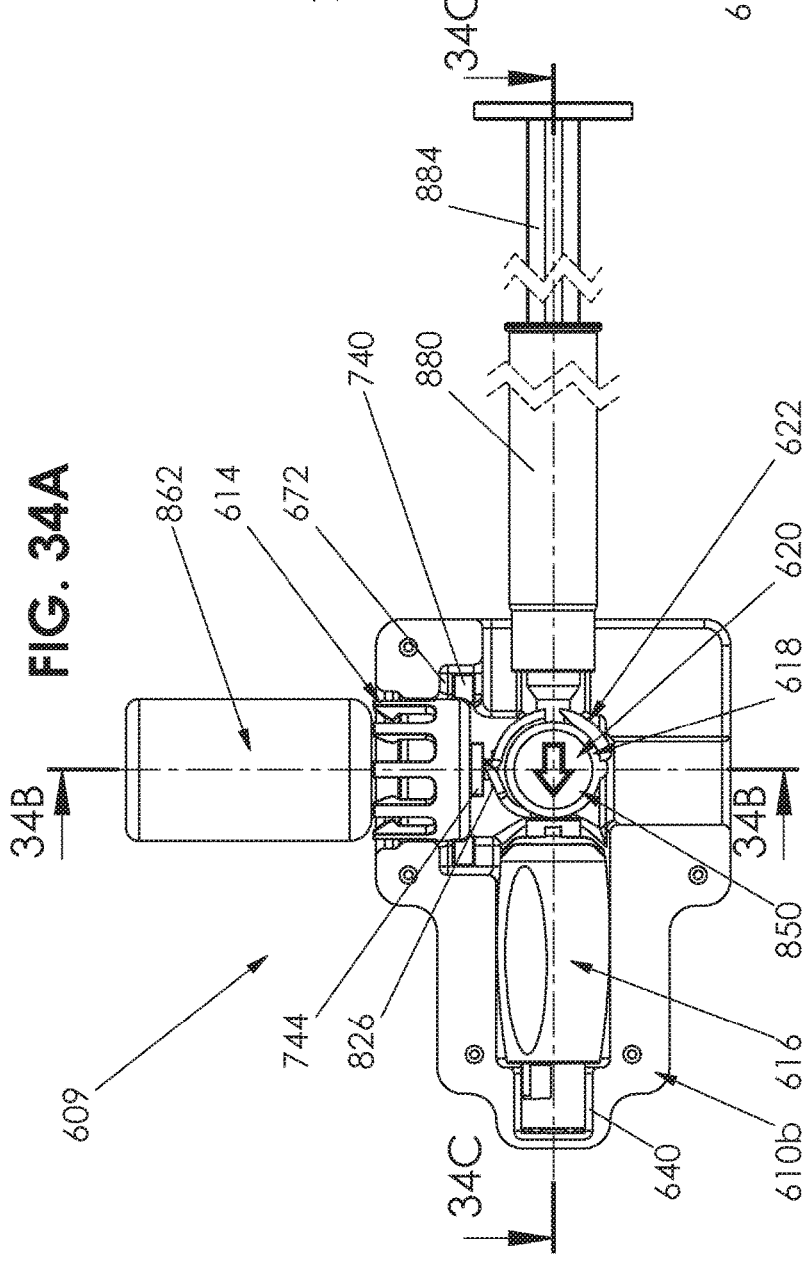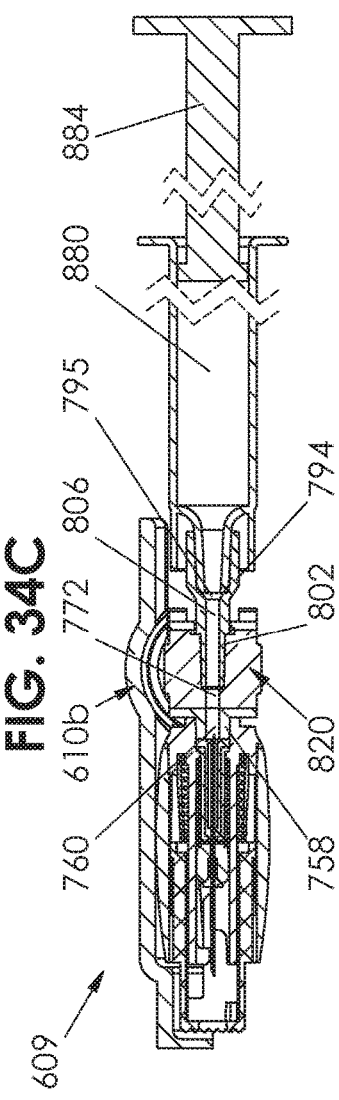

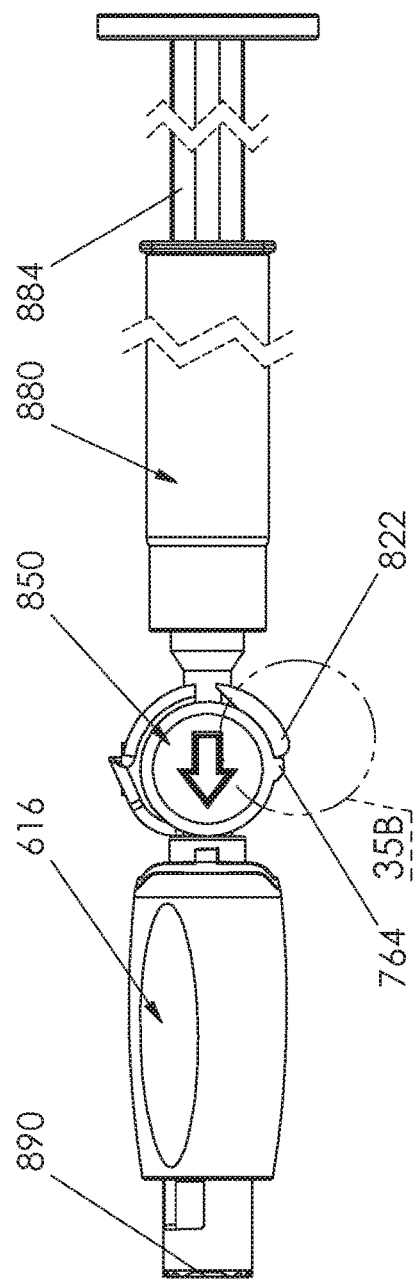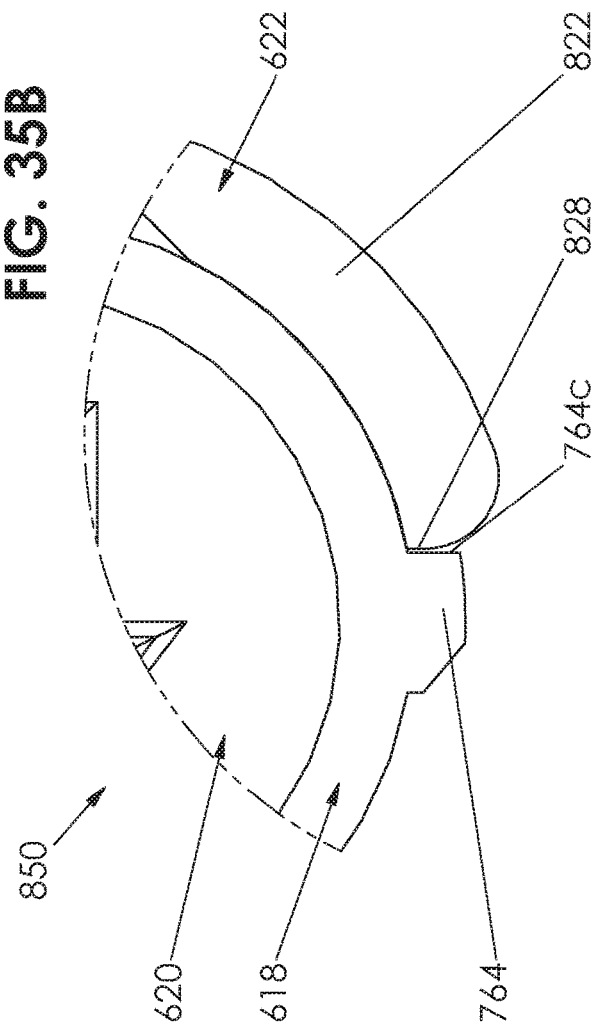

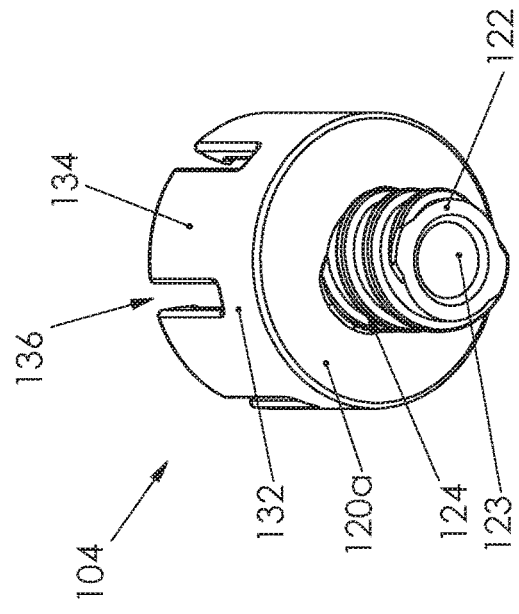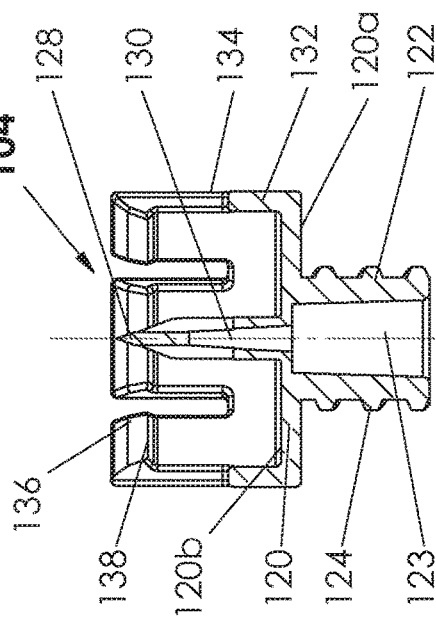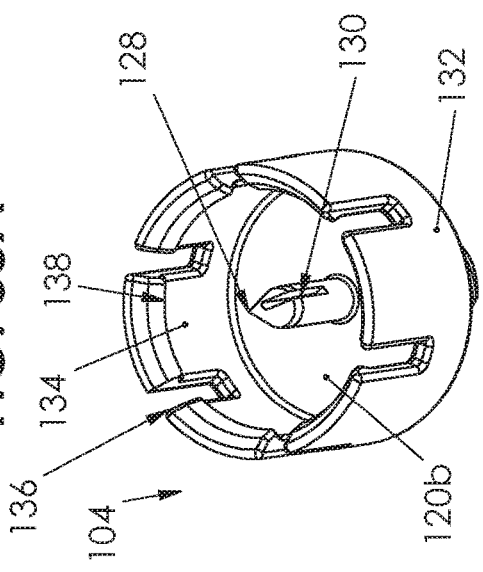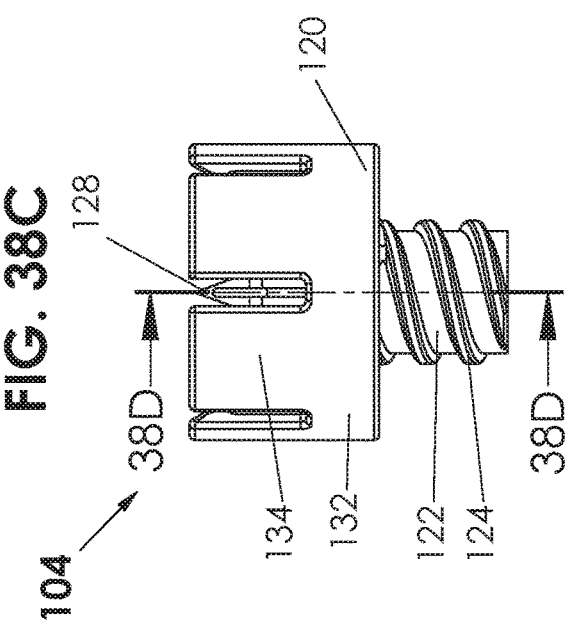

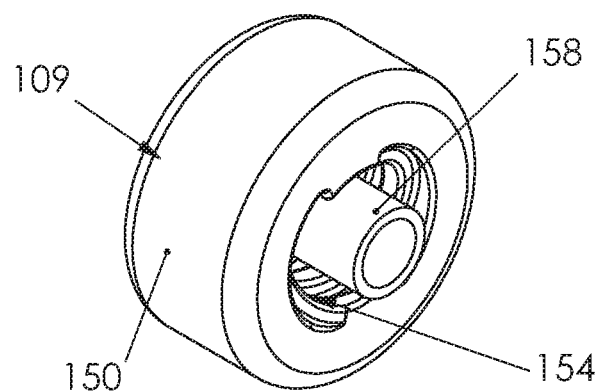
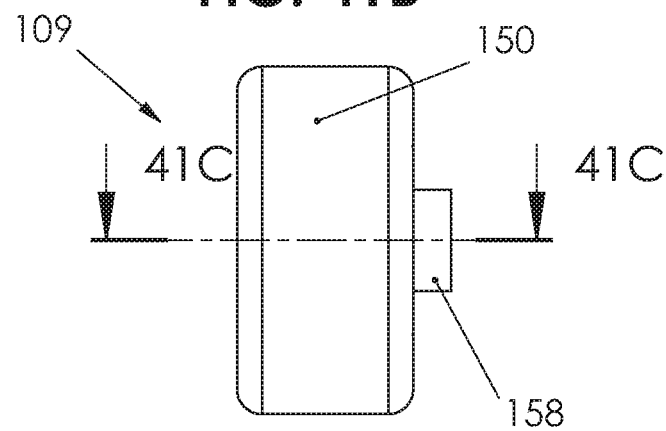
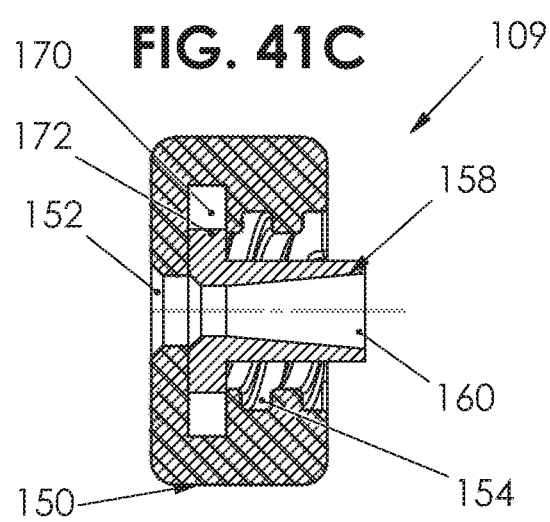

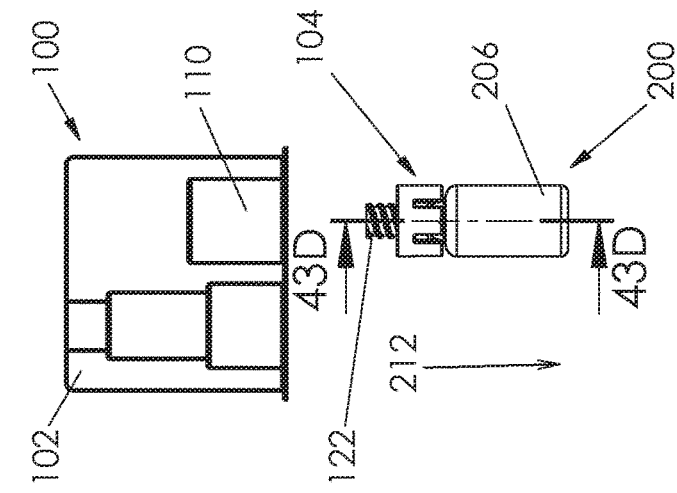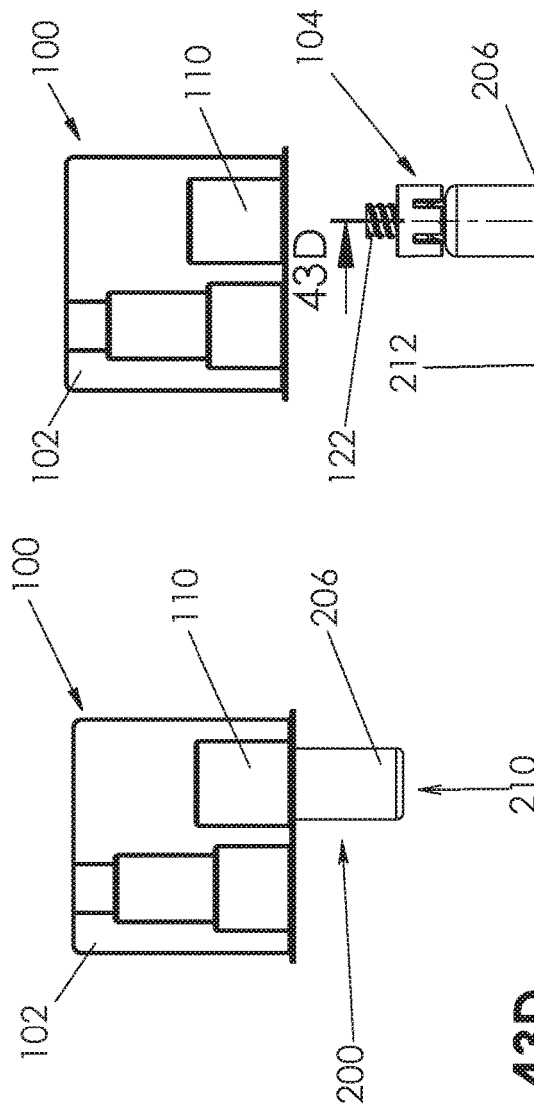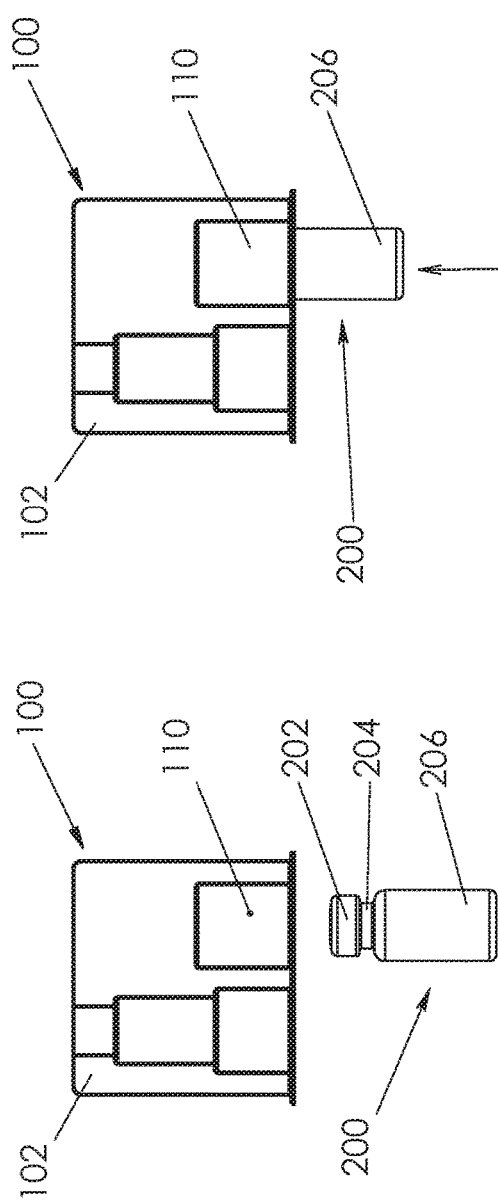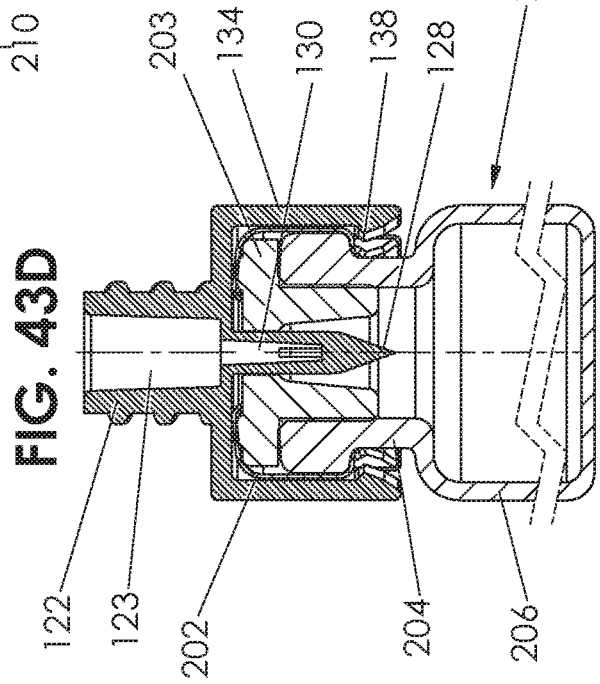

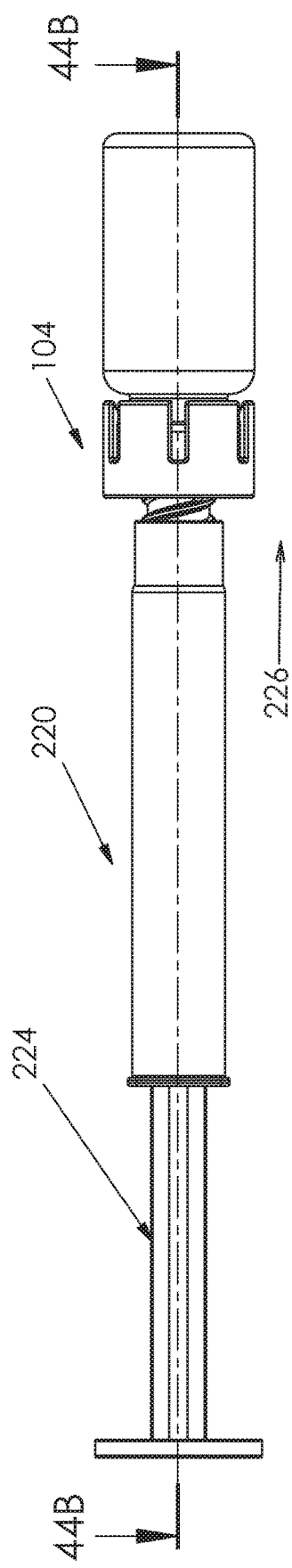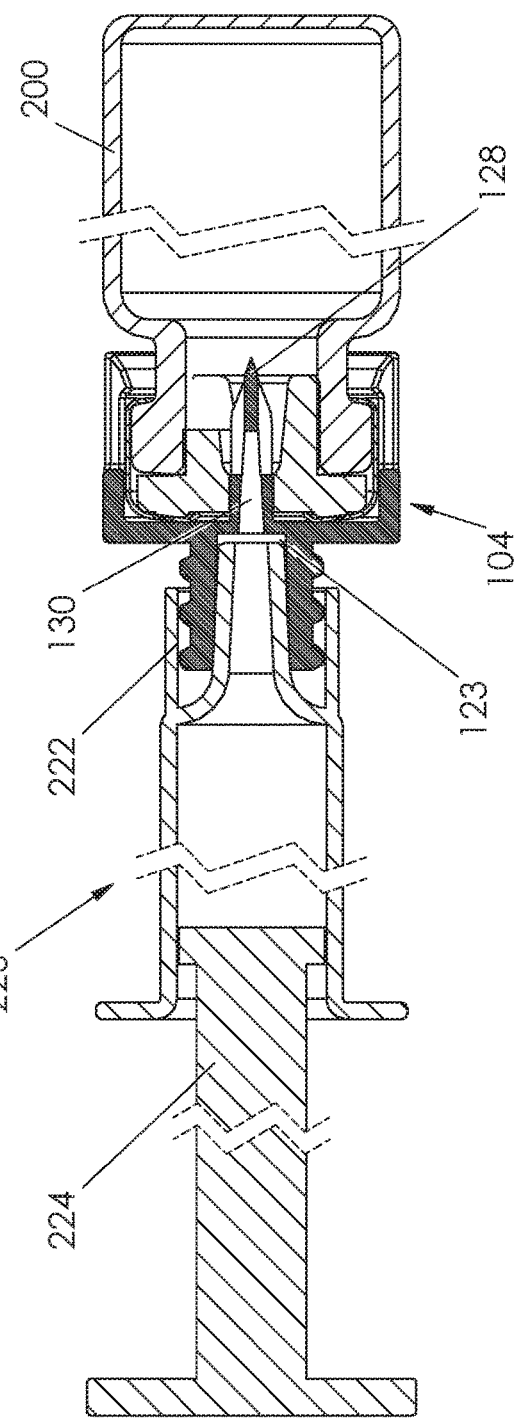

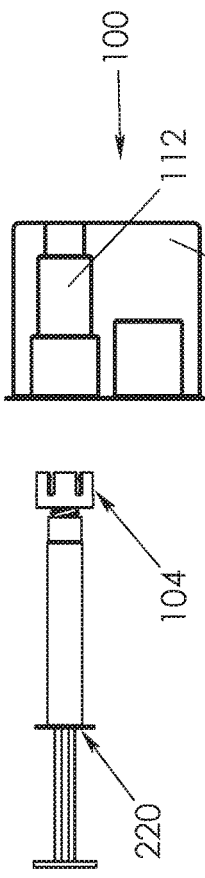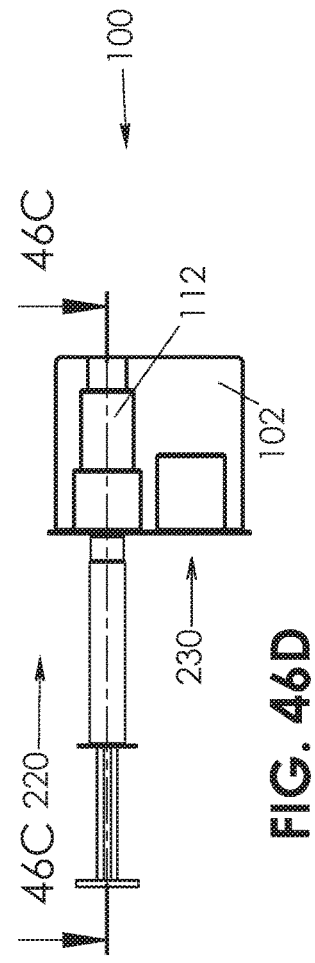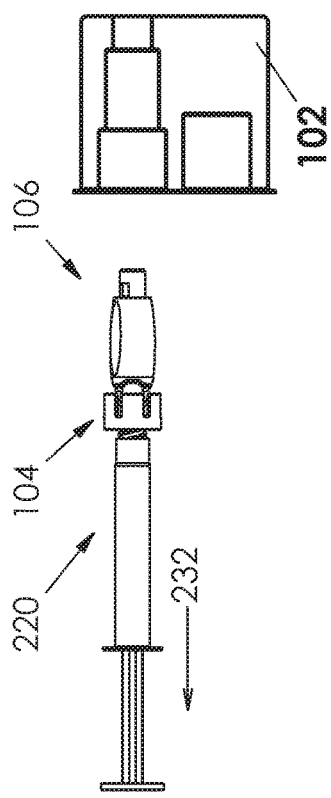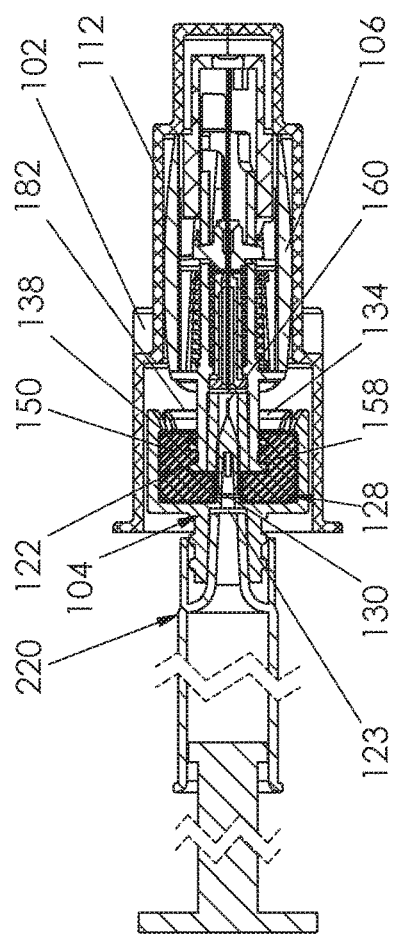
FIG. 46A
FIG. 46B
FIG. 46C
FIG. 46D

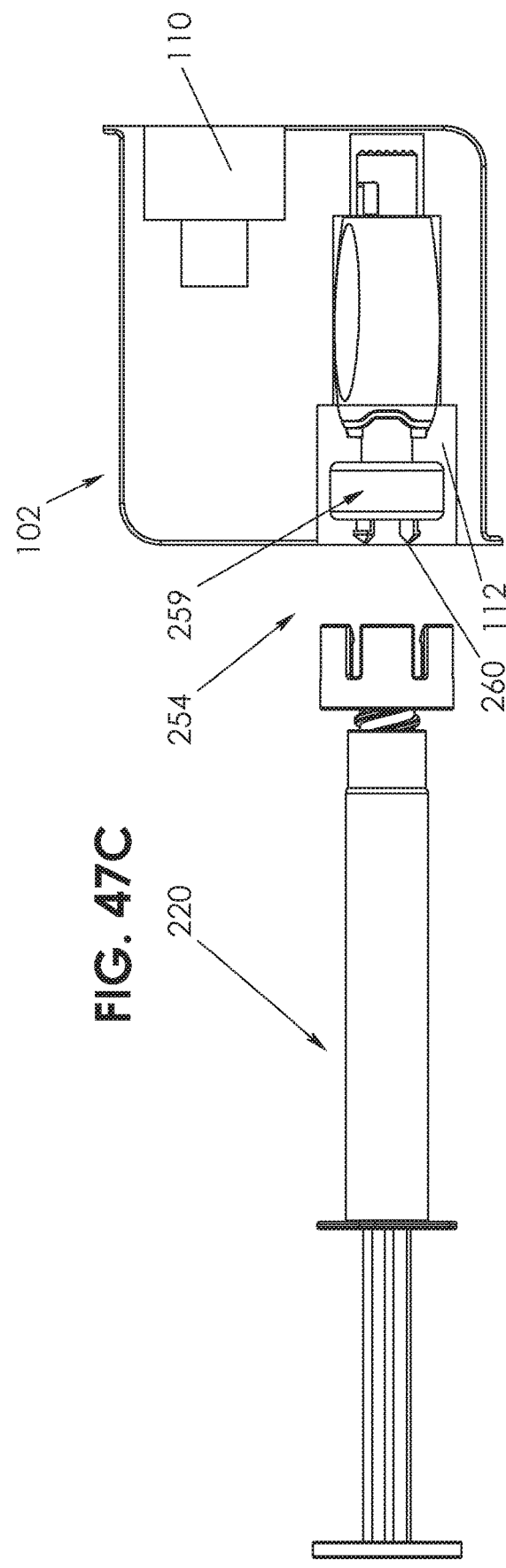

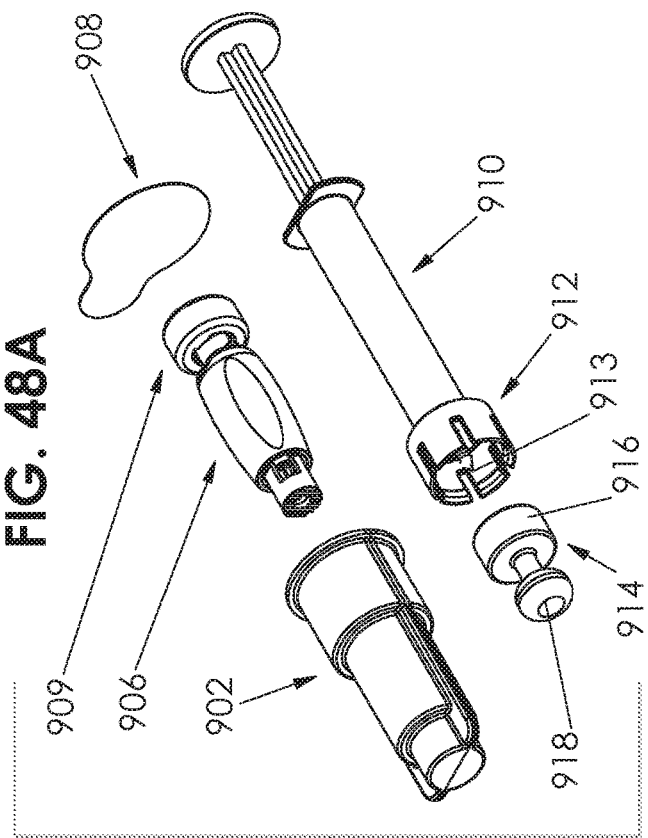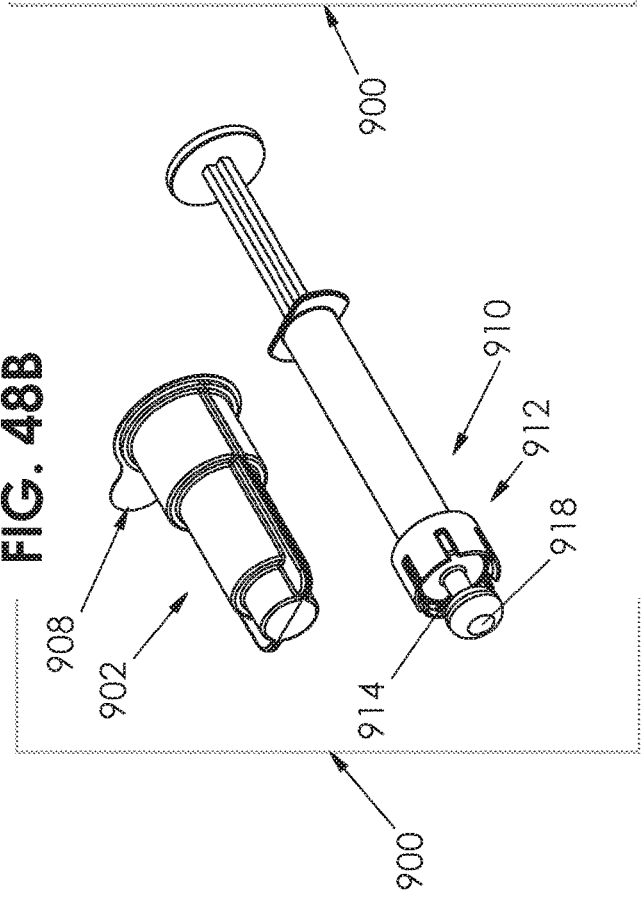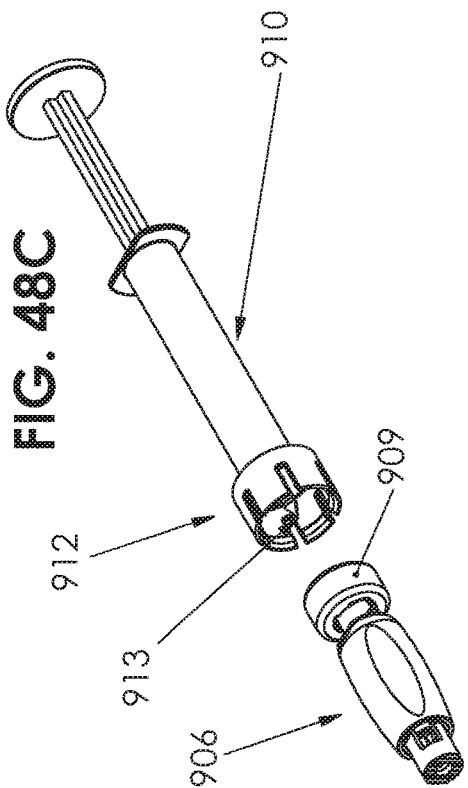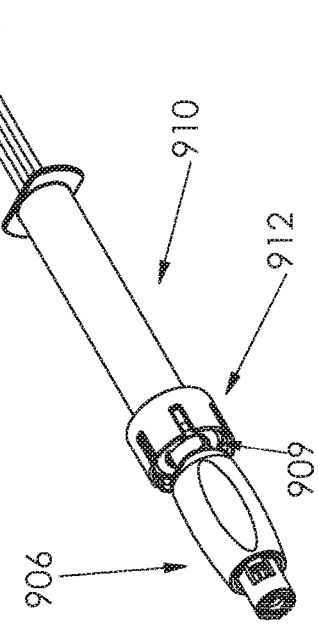

SYSTEMS FOR INTERFACING BETWEEN A SYRINGE, A DRUG VIAL AND A NEEDLE

FIELD AND BACKGROUND OF THE INVENTION

The invention, in some embodiments, relates to the field of injection devices, and more specifically to unitary and multi-part devices for interfacing between a drug vial, a syringe, and a needle, and to methods of use thereof.

SUMMARY OF THE INVENTION

In accordance with an aspect of the present invention, there is provided an injection system including a vial adaptor for connection to a vial, an injection device port for connection to an injection device, a hypodermic needle, and a valve, functionally associated with the vial adaptor, the injection device port, and the needle, the valve having a first orientation wherein the injection device port is in fluid flow communication with the vial adaptor and a second orientation wherein the injection device port is in fluid flow communication with the hypodermic needle, wherein rotation of the injection device port between a first position and a second position thereof, drives transition of the valve from the first orientation to the second orientation.

In some embodiments, in the first orientation of the valve, the injection device port is not in fluid flow communication with the needle. In some embodiments, in the second orientation of the valve, the injection device port is not in fluid flow communication with the vial adaptor.

In some embodiments, in the first orientation of the valve the vial adaptor is located in a first position and is connected to a port of the valve, and wherein in the second orientation of the valve, the vial adaptor is located in a second position, longitudinally displaced from the first position, and is disconnected from the valve. In some embodiments, the disconnection between the vial adaptor and the valve is driven by rotation of the injection device port.

In some embodiments, the vial adaptor is permanently connected to the port of the valve.

In some embodiments, in the first orientation, a longitudinal axis of the vial adaptor coincides with a longitudinal axis of the injection device port. In some embodiments, in the second orientation, a longitudinal axis of the needle coincides with a longitudinal axis of the injection device port.

In some embodiments, the needle includes an automatic needle.

In some embodiments, in the second orientation of the valve, the valve is locked and transition of the valve into the first orientation is prevented.

In some embodiments, the injection system further includes a housing, the housing including a needle compartment housing the needle, a valve compartment housing the valve, a vial adaptor port housing the vial adaptor and enabling access thereto for connection of a vial thereto, and an injection device rotation port housing the injection device port and enabling rotation thereof so as to drive transition of the valve from the first orientation to the second orientation.

In some embodiments, the needle compartment is sized so that the needle cannot move freely therein. In some embodiments, the needle is fully enclosed within the needle compartment and is tamper proof.

In some embodiments, the housing further includes at least one valve position marker, the valve position marker adapted to provide to a user an indication whether the valve is in the first orientation or in the second orientation. In some embodiments, the valve indication includes at least one of a visual indication, and audible indication, and a tactile indication.

In some embodiments, the housing further includes at least one vial adaptor position marker, the vial adaptor position marker adapted to provide to a user a vial adaptor indication whether the vial adaptor is connected to the valve or is disconnected from the valve. In some embodiments, the vial adaptor indication includes at least one of a visual indication, an audible indication, and a tactile indication.

In some embodiments, the housing further includes an injector removal path, wherein, in the first orientation of the valve, the injector removal path is blocked thereby preventing removal of the needle from the housing, and in the second orientation of the valve the injector removal path enables removal of the injection device port, the valve, and the needle from the housing as a single unit.

In accordance with another aspect of the present invention, there is provided a method for preparing an injection device for injection, the method including:

providing an injection system according to any one of the preceding claims;

when the valve is in the first orientation, connecting a vial to the vial adaptor and connecting an injection device to the injection device port;

drawing liquid from the vial into the injection device, the liquid passing through the vial adaptor, the valve, and the injection device port;

rotating the injection device relative to the vial adaptor, thereby rotating the injection device port and transitioning the valve from the first orientation to the second orientation and locking the valve so as to prevent transition of the valve back to the first orientation.

In some embodiments, drawing liquid includes at least one of mixing and reconstituting of at least one of powder and a lyophilized drug with a liquid in the injection device. In some embodiments, at least one of mixing and reconstituting further includes removing the vial from the vial adaptor and connecting a second vial, different from the vial, to the vial adaptor.

In some embodiments, the needle, the valve, and the injection device port are enclosed in a housing portion, the method further including removing the needle, the valve, the injection device port, and the injection device, as a single unit, from the housing portion.

In accordance with yet another aspect of the present invention, there is provided an adaptor for connecting a vial adaptor to an injection device, including a base portion sized and adapted for connection to a vial adaptor, and including a spike bore adapted to receive a spike of the vial adaptor and a connector portion configured for connection to a connector of an injection device, the connector portion having a connector bore defined therein, the connector bore being longitudinally aligned with the spike bore.

In some embodiments, the connector portion includes a thread therein configured for connection to a luer connector. In some embodiments, the connector portion is configured for connection to a luer connector. In some embodiments, the luer connector includes a female luer connector of a hypodermic needle.

In some embodiments, the spike bore includes an elastomeric seal. In some embodiments, the connector portion includes a tubular portion adapted to seal against a bore of the injection device.

In some embodiments, the base portion is sized to correspond to the circumference of a medicine vial. In some embodiments, the base portion is sized to engage a vial adaptor by friction. In some embodiments, the base portion further includes a locking mechanism adapted to removably lock the base portion to a vial adaptor, when engaged therewith.

In accordance with an additional aspect of the present invention, there is provided a needle device, including an adaptor as described hereinabove and a hypodermic needle connected to the connector portion of the adaptor.

In some embodiments, the adaptor and the hypodermic needle are integrally formed. In some embodiments, the needle includes an automatic needle.

In accordance with a further aspect of the present invention, there is provided an injection system including a needle device as described hereinabove, a vial adaptor, and an injection device, the base portion of the needle device sized to fit and engage in the vial adaptor.

In some embodiments, the vial adaptor is irremovably attached to an end of the injection device. In some embodiments, the vial adaptor is integrally formed with the injection device. In some embodiments, the vial adaptor is irremovably bonded to the injection device by at least one of welding and an adhesive.

In some embodiments, a lumen of the vial adaptor is in fluid flow communication with a lumen of the injection device, such that a liquid disposed in the injection device can be expelled therefrom via the vial adaptor.

In some embodiments, the injection device is prefilled with an injection fluid, the system further including a spike shield engaging and sealing a spike of the vial adaptor so as to prevent contamination of the injection fluid.

In some embodiments, the injection system further includes a casing housing the needle device and at least one vial including a fluid, the casing enabling access to the vial, and only subsequently enabling access to the needle device.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIGS. 1A and 1B are exploded view illustrations of a system for interfacing between a syringe, a drug vial, and a needle, according to two different embodiments of the teachings herein;

FIGS. 2A and 2B are simplified pictorial illustrations of the systems of respective FIGS. 1A and 1B as assembled according to an embodiment of the teachings herein;

FIGS. 3A and 3B are pictorial illustrations of two portions of a housing forming part of the system of FIGS. 1A and 2A according to an embodiment of the teachings herein;

FIGS. 4A, 4B, and 4C are, respectively, inner side view, top view, and outer side view planar illustrations of the housing portion of FIG. 3A;

FIGS. 5A and 5B are pictorial illustrations of two portions of a housing forming part of the system of FIGS. 1B and 2B according to another embodiment of the teachings herein;

FIGS. 6A, 6B, and 6C are, respectively, inner side view, top view, and outer side view planar illustrations of the housing portion of FIG. 5A;

FIGS. 7A and 7B are pictorial illustrations of a cam disk forming part of the system of FIGS. 1A and 2A according to an embodiment of the teachings herein;

FIGS. 8A, 8B, and 8C are, respectively, inner side view, top view, and outer side view planar illustrations of the cam disk of FIGS. 7A and 7B;

FIGS. 9A and 9B are pictorial illustrations of cam disks forming part of the system of FIGS. 1B and 2B according to another embodiment of the teachings herein;

FIGS. 10A, 10B, and 10C are, respectively, inner side view, top view, and outer side view planar illustrations of the cam disk of FIGS. 9A and 9B;

FIGS. 11A, 11B, 11C, and 11D are, respectively, top and bottom view pictorial illustrations, a side view planar illustration, and a sectional illustration of a vial adaptor forming part of the systems of FIGS. 1A-2B according to an embodiment of the teachings herein;

FIGS. 13A, 13B, 13C, and 13D are, respectively, two side view pictorial illustrations, a side view planar illustration, and a sectional illustration of a valve core forming part of the systems of FIGS. 1A to 2B according to an embodiment of the teachings herein;

FIGS. 14A, 14B, 14C, and 14D are, respectively, a pictorial illustration, a front view planar illustration, a top view planar illustration, and a sectional illustration of a valve driver forming part of the systems of FIGS. 1A to 2B according to an embodiment of the teachings herein;

FIGS. 15A, 15B, 15C, 15D, and 15E are, respectively, an exploded view illustration, a pictorial illustration, a side view planar illustration, and two sectional illustrations of a valve comprising the valve housing of FIGS. 12A-12E, the valve core of FIGS. 13A-13D, and the valve driver of FIGS. 14A-14C according to an embodiment of the teachings herein, in a first valve position;

FIGS. 16A, 16B, 16C, 16D, and 16E are, respectively, an exploded view illustration, a pictorial illustration, a side view planar illustration, and two sectional illustrations of the valve of FIGS. 15A-15E in a second valve position;

FIGS. 17A, 17B, 17C, 17D, 17E, and 17F are, respectively, a pictorial illustration, a side view planar illustration, a partially cutaway side view planar illustration, and three sectional illustrations of the system of FIGS. 1A and 2A according to an embodiment of the teachings herein, in an initial operational position;

FIGS. 18A and 18B are, respectively, a side view planar illustration and a sectional illustration of the injection system of FIGS. 17A-17F in a vial connection operational position;

FIGS. 19A and 19B are, respectively, a side view planar illustration and a sectional illustration of the injection system of FIGS. 17A-17F in a syringe connection and medicine reconstitution or transfer operational position;

FIGS. 20A, 20B, 20C, 20D, 20E, 20F, 20G, 20H, and 20I are, respectively, a side view planar illustration, a partially cut away side view planar illustration, an enlarged view of a portion of FIG. 20B, four sectional illustrations, a partially cutaway top view planar illustration, and a sectional illustration, of the injection system of FIGS. 17A-17F in a syringe rotation, vial adaptor disengagement, and needle connection operational position;

FIGS. 21A and 21B are, respectively, a top view planar illustration of a needle, valve, and syringe removed from the system of FIGS. 17A-17F and ready for injection, and an enlarged view of a portion of FIG. 21A;

FIGS. 24A, 24B, and 24C are, respectively, pictorial illustrations of two portions of a housing forming part of the system of FIGS. 22 and 23 according to an embodiment of the teachings herein, and an inner side view planar illustration of the housing portion of FIG. 24A;

FIGS. 25A, 25B, 25C, and 25D are, respectively, top and bottom view pictorial illustrations, a side view planar illustration, and a sectional illustration of a vial adaptor forming part of the system of FIGS. 22 and 23 according to an embodiment of the teachings herein;

FIGS. 26A, 26B, 26C, 26D, and 26E are, respectively, a side view pictorial illustration, a top view pictorial illustration, a side view planar illustration, a top view planar illustration, and a sectional illustration of a valve housing forming part of the system of FIGS. 22 and 23 according to an embodiment of the teachings herein;

FIGS. 27A, 27B, 27C, and 27D are, respectively, two side view pictorial illustrations, a side view planar illustration, and a sectional illustration of a valve core forming part of the system of FIGS. 22 and 23 according to an embodiment of the teachings herein;

FIGS. 28A, 28B, and 28C are, respectively, a pictorial illustration, a front view planar illustration, and a sectional illustration of a valve driver forming part of the system of FIGS. 22 and 23 according to an embodiment of the teachings herein;

FIGS. 29A, 29B, 29C, 29D, and 29E are, respectively, an exploded view illustration, a pictorial illustration, a side view planar illustration, and two sectional illustrations of a valve comprising the valve housing of FIGS. 26A-26E, the valve core of FIGS. 27A-27D, and the valve driver of FIGS. 28A-28C according to an embodiment of the teachings herein, in a first valve position;

FIGS. 30A, 30B, 30C, 30D, and 30E are, respectively, an exploded view illustration, a pictorial illustration, a side view planar illustration, and two sectional illustrations of the valve of FIGS. 29A-29E in a second valve position;

FIGS. 32A and 32B are, respectively, a side view planar illustration and a sectional illustration of the injection system of FIGS. 31A-31D in a vial connection operational position;

FIGS. 33A and 33B are, respectively, a side view planar illustration and a sectional illustration of the injection system of FIGS. 31A-31D in a syringe connection and medicine transfer and reconstitution operational position;

FIGS. 34A, 34B and 34C are, respectively, a partially cut away side view planar illustration, and two sectional illustrations of the injection system of FIGS. 31A-31D in a syringe rotation and needle fluid communication operational position;

FIGS. 35A and 35B are, respectively, a side view planar illustration of a needle, valve, and syringe removed from the system of FIGS. 31A-31D and ready for injection, and an enlarged view of a portion of FIG. 35A;

FIGS. 38A, 38B, 38C, and 38D are, respectively, top and bottom view pictorial illustrations, a side view planar illustration, and a sectional illustration of a vial adaptor forming part of the system of FIGS. 36-37D according to an embodiment of the teachings herein;

FIGS. 41A, 41B, and 41C are, respectively, a pictorial illustration, a side view planar illustration, and a sectional illustration of a needle adaptor forming part of the system of FIG. 36 according to another embodiment of the teachings herein;

FIGS. 43A, 43B, and 43C are side view planar illustrations of three steps of connecting a vial adaptor of FIGS. 38A-38D to a vial using the system of FIG. 37A and removal of the vial adaptor from the casing;

FIG. 43D is a sectional illustration of the connection between the vial adaptor and the vial following completion of the step of FIG. 43C;

FIGS. 44A and 44B are, respectively, a side view planar illustration and a sectional illustration of a step of connecting a syringe, optional mixing/reconstitution, and drawing fluid from the drug vial and adaptor of FIGS. 43C-43D into a syringe;

FIGS. 46A and 46B are side view planar illustrations of the step of connecting the syringe and vial adaptor of FIGS. 45A-45B to a needle adaptor and needle using the system of FIG. 37A;

FIG. 46C is a sectional illustration of the connection between the vial adaptor, needle adaptor, and needle during the step of FIG. 46B;

FIG. 46D is a side view planar illustration of the connected syringe, vial adaptor, needle adaptor, and needle ready for injection;

FIG. 47A is a pictorial illustration of a vial adaptor forming part of a system such as the system of FIG. 36, according to an embodiment of the teachings herein;

FIG. 47B is a pictorial illustration of a needle adaptor forming part of a system such as the system of FIG. 36 according to an embodiment of the teachings herein, and constructed to snap fit with the vial adaptor of FIG. 47A;

FIG. 47C is a partially cut-away side view planar illustration of a step of connecting a syringe having attached thereto the vial adaptor of FIG. 47A to a needle having attached thereto the needle adaptor of FIG. 47B;

FIG. 47D is a pictorial illustration of the vial adaptor of FIG. 47A when connected to the needle adaptor of FIG. 47B, according to an embodiment of the teachings herein;

FIG. 48A is an exploded view illustration of another system for interfacing between a syringe, a drug vial, and a needle, the system including a spike shield, according to an embodiment of the teachings herein;

FIG. 48B is a simplified pictorial illustration of the system of FIG. 48A, as assembled;

FIG. 48C is a simplified pictorial illustration of the system of FIG. 48A in a needle connection operational position; and FIG. 48D is a simplified pictorial illustration of the system of FIG. 48A, ready for injection.

DESCRIPTION OF SOME EMBODIMENTS OF THE INVENTION

Figure 12A:
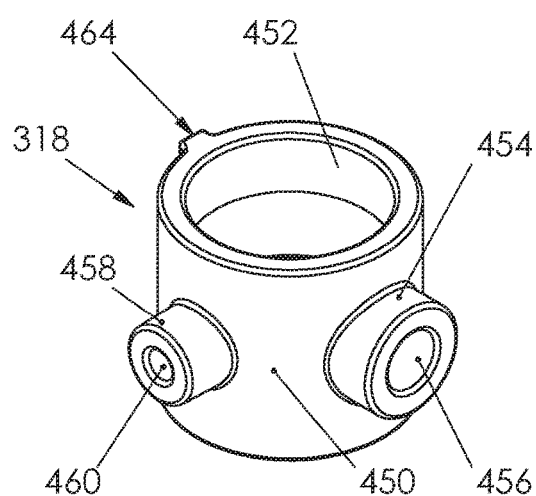
FIGS. 12A, 12B, 12C, 12D, and 12E are, respectively, a side view pictorial illustration, a top view pictorial illustration, a side view planar illustration, a top view planar illustration, and a sectional illustration of a valve housing forming part of the systems of FIGS. 1A to 2B according to an embodiment of the teachings herein.
Figure 12B:
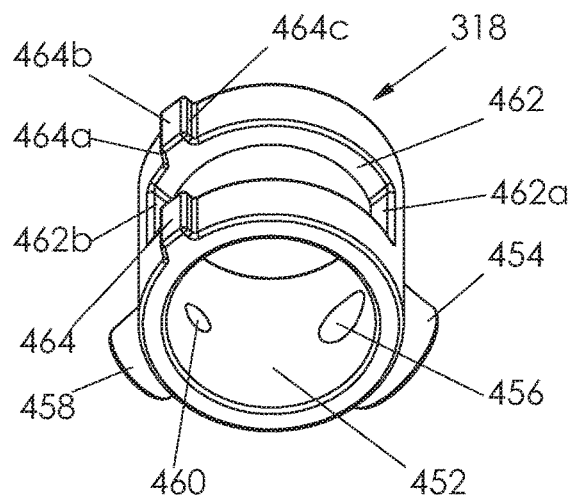

The invention, in some embodiments, relates to the field of injection devices, and more specifically to unitary and multi-part devices for interfacing between a drug vial, a syringe, and a needle, and to methods of use thereof.

The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment of the invention in detail, it is to be understood that the invention is not limited in its applications to the details of construction and the arrangement of the components and/or methods set forth in the following description and/or illustrated in the drawings and/or the Examples. The invention can be implemented with other embodiments and can be practiced or carried out in various ways. It is also understood that the phraseology and terminology employed herein is for descriptive purpose and should not be regarded as limiting.

Reference is now made to FIGS. 1A and 1B, which are exploded view illustrations of systems 300a and 300b for interfacing between a syringe, a drug vial, and a needle, according to two different embodiments of the teachings herein, and to FIGS. 2A and 2B, which are simplified pictorial illustrations of the systems 300a and 300b of respective FIGS. 1A and 1B as assembled according to an embodiment of the teachings herein.

As seen in FIG. 1A, the system 300a according to the teachings herein includes a casing 302 associated with a seal 308, the casing 302 housing an injection system 309a (seen in FIG. 2A) including a housing 310 defined by a pair of housing portions 310a and 310b, a pair of cam disks 312a and 312b, a vial adaptor 314, a needle 316, a valve housing 318, a valve core 320, and a valve driver 322.

Similarly, as seen in FIG. 1B, the system 300b according to the teachings herein includes a casing 302 associated with a seal 308, the casing 302 housing an injection system 309b (seen in FIG. 2B) including a housing 310 defined by a pair of housing portions 310c and 310d, a pair of cam disks 312c and 312d, a vial adaptor 314, a needle 316, a valve housing 318, a valve core 320, and a valve driver 322.

Casing 302 and seal 308 typically form a sterile package, so as to prevent contamination of the injection systems 309a or 309b disposed therein prior to its use for injection of a medicament. In some embodiments casing 302 comprises wall portions 330 defines a hollow space 332 for housing injection systems 309a or 309b. Each of wall portions 330 typically terminates in a lip portion 334 configured to sealingly engage seal 308. Typically, seal 308 includes a seal grip 336 for the user to grip the seal 308 for removal thereof. In some embodiments, hollow space 332 is sized so that injection system 309a or 309b engages walls 330 and cannot freely move around within space 332.

Housing portions 310a and 310b may be any suitable housing portions, for example as described hereinbelow with reference to FIGS. 3A to 4C. Housing portions 310c and 310d may be any suitable housing portions, for example as described hereinbelow with reference to FIGS. 5A to 6C. As explained in further detail hereinbelow, housing portions 310a and 310b may be mirror image symmetric, such that the housing portions symmetrically engage each other while enclosing other components of the injection system 309a. Similarly, housing portions 310c and 310d may be mirror image symmetric, such that the housing portions symmetrically engage each other while enclosing other components of injection system 309b. Housing portions 310a and 310b, and 310c and 310d, may be formed as one unitary housing, or as two or more housing portions separated at different locations, and assembled to each other by ultrasonic welding, bonding, snap fit engagement or any other suitable form of engagement.

Figures 9A, 9B, 10A, 10B, 10C:
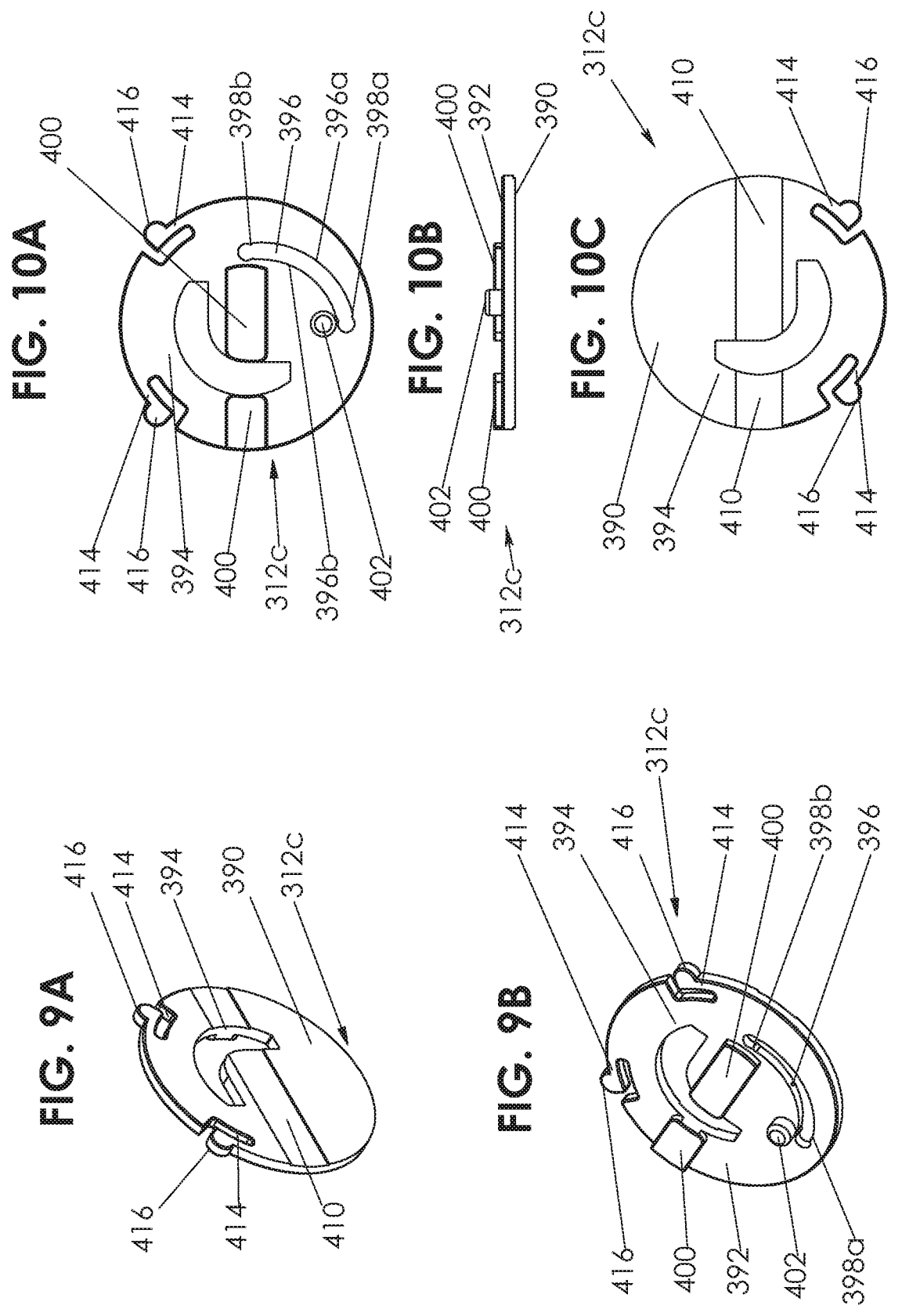

Cam disks 312a and 312b may be any suitable cam disks, for example as described hereinbelow with reference to FIGS. 7A to 8C. Similarly, cam disks 312c and 312d may be any suitable cam disks, for example as described hereinbelow with reference to FIGS. 9A to 10C. As explained in further detail hereinbelow, cam disks 312a and 312b, and cam disks 312c and 312d, may be mirror image symmetric, such that the cam disks may symmetrically oppose each other within housing 310 and engage opposite sides of the vial adaptor 314 for driving motion thereof.

The vial adaptor 314 may be any suitably configured vial adaptor, for example as described hereinbelow with reference to FIGS. 11A to 11D. As explained in further detail hereinbelow, in use, the vial adaptor engages the cam disks 312a and 312b or cam disks 312c and 312d, and is driven thereby between two positions within injection system 309a or 309b, respectively.

The needle 316 may be any suitable needle, including a standard hypodermic needle such as a BD Regular Bevel Needle or a safety needle such as a BD SafetyGlide Hypodermic Needle, both commercially available from Becton Dickinson and Company of 1 Becton Drive, Franklin Lakes, N.J. 07417-1880. In some embodiments, the needle 106 is an automatic injection needle, for example as disclosed in U.S. Pat. No. 7,901,382, filed on Sep. 15, 2004 and entitled "AUTOMATIC NEEDLE DEVICE" and in U.S. patent application Ser. No. 14/505,690, filed on Oct. 3, 2014 and entitled "AUTOMATIC NEEDLE APPARATUS" which are fully incorporated by reference herein.

The valve housing 318 may be any suitable valve housing, for example as described hereinbelow with reference to FIGS. 12A to 12E. The valve core 320 may be any suitable valve core, for example as described hereinbelow with reference to FIGS. 13A to 13D. The valve driver 322 may be any suitable valve driver, for example as described hereinbelow with reference to FIGS. 14A to 14C. As explained in further detail hereinbelow with reference to FIGS. 15A to 16E, valve housing 318, valve core 320, and valve driver 322 together form a valve 550 (FIGS. 15A-16E) which can assume two operative valve positions.

Reference is now made to FIGS. 3A and 3B, which are pictorial illustrations of housing portions 310a and 310b forming part of the system 300a of FIGS. 1A and 2A, to FIGS. 4A, 4B, and 4C, which are, respectively, inner side view, top view, and outer side view planar illustrations of the housing portion 310*a* of FIG. 3A, to FIGS. 5A and 5B, which are pictorial illustrations of housing portions 310*c* and 310*d* of system 300*b* of FIGS. 1B and 2B, and to FIGS. 6A, 6B, and 6C, which are, respectively, inner side view, top view, and outer side view planar illustrations of the housing portion 310*c* of FIG. 5A.

It is appreciated that, in some embodiments, housing portions 310*a* and 310*b*, and housing portions 310*c* and 310*d*, may be mirror image symmetrical, such that any elements included in one of the housing elements are included in the other of the housing elements as well, even if not clearly visible in the drawings of the other housing element. In other embodiments, elements included in one of the housing elements may not be included in the other.

As seen in FIGS. 3A-6C, each of housing portions 310*a*, 310*b*, 310*c*, and 310*d* includes a generally tubular needle compartment 340, configured to house needle 316 (FIGS. 1A-1B). Typically, the needle compartment 340 is sized so that the needle 316 cannot move freely within the compartment. In some embodiments, such as those shown in FIGS. 3A to 6C, the needle compartment 340 may include a first portion 342*a* having a first diameter, and a second portion 342*b* having a second diameter, greater than the diameter of first portion 342*a*, and a shoulder 344 defined between the first and second portions. As such, when needle 316 is situated within compartment 340, the tip of the needle is disposed within narrower portion 342*a* and the body of the needle, which typically has a greater diameter, is disposed in wider portion 342*b*. This ensures that all parts of the needle are kept relatively in place and cannot move freely within the compartment 340, and that the needle cannot "slip" too far into the compartment as the wider portion of the needle is blocked by shoulder 344, thus preventing premature actuation of automatic needle device and protecting other needle types from needle tip damage. The end of needle compartment 340, designed to be adjacent to the tip of the needle when the needle is disposed therein, is sealed by a wall portion 346. It is appreciated that in some embodiments, wall portion 346 may only partially close needle compartment 340 or may not exist at all, leaving the compartment open.

Each of housing portions 310*a*, 310*b*, 310*c* and 310*d* further includes a generally circular cam and valve compartment 350, functionally associated with needle compartment 340. Cam and valve compartment 350 includes a wall 354 having protruding from an inner surface thereof towards the interior of housing 310 a generally trapezoidal fin 358, including a sloped surface 360, and configured so as to prevent the valve disposed within compartment 350 from locking in a fixed position until removal of the valve from the housing 310, as explained in further detail hereinbelow with reference to FIGS. 20A-20I.

In some embodiments, cam and valve compartment 350 includes one or more markers 362 of valve position. As explained in further detail hereinbelow, markers 362 cooperate with a portion of cam disks 312 so as to provide to the user an indication of the operative position of the valve disposed within valve compartment 350. In some embodiments markers 362 comprise an indentation out of compartment 350, or a throughgoing hole, such that the portion of cam disks 312 cooperative therewith is visible therethrough.

In some embodiments, such as the embodiment of FIGS. 3A-4C, the indication may be a tactile indication and/or a visual indication and/or an audible indication, for example provided by a click between marker 362 and a portion of disks 312*a* and 312*b* described hereinbelow with reference to FIGS. 7A to 8C. In other embodiments, such as the embodiment of FIGS. 5A-6C, the circumference of cam and valve compartment 350 includes a plurality of locking points 363, which cooperate with corresponding locks in cam disks 312*c* and 312*d* described hereinbelow with reference to FIGS. 9A to 10C, to provide a tactile and/or audible click and/or visual indication when the cam disk and valve have reached the end of the range of motion and are in one of the two or more operative positions.

In some embodiments, the indication may be a visual indication, for example provided by a color visible through windows of markers 362 and/or through suitable user feedback windows 364. For example, in the embodiment of FIGS. 3A-4C, when the valve is positioned so as to allow engagement with a vial, a visual indication is provided in window 364*a* shaped like a vial, and when the valve is positioned so as to allow injection, a visual indication is provided in window 364*b* shaped like a syringe, in addition to the indication provided by markers 362. As another example, in the embodiment of FIGS. 5A-6C, when the valve is positioned so as to allow engagement with a vial, a visual indication is provided in window 364*a* indicating connection of the vial to the syringe by the numerals 1 and 2, and when the valve is positioned so as to allow injection, a visual indication is provided in window 364*b* comprising arrows indicating a direction of extraction of the syringe, in addition to the indication provided by markers 362.

In some embodiments, windows 364 may allow the user to see graphic indications, icons, or colors disposed on or painted onto cam disks 312. For example, in the embodiment of FIGS. 5A-6C, windows 364*a* and 364*b* cooperate with a colored stripe 410 on cam disks 312*c* and 312*d* described hereinbelow with reference to FIGS. 9A to 10C, such that the color is visible through the windows 364*a* or 364*b* depending on the orientation of the cam disks 312*c* and 312*d*.

In some embodiments, such as the embodiment of FIGS. 3A-4C, cam and valve compartment 350 includes one or more markers 368 of vial adaptor position. As explained in further detail hereinbelow, markers 368 cooperate with protrusions on vial adaptor 314 described hereinbelow with reference to FIGS. 11A-11D, so as to provide to the user an indication of the operative position of the vial adaptor 314. In some embodiments, the indication may be a tactile and/or an audible indication, for example provided by a click between marker 368 and the vial adaptor 314. In some embodiments, the indication may be a visual indication, for example provided by a color visible through windows of markers 368. Specifically, an internal marker 368*a* corresponds to a first position of the vial adaptor 314, which is axially closer to compartment 350 along axis 373, and external marker 368*b* corresponds to a second position of vial adaptor 314 axially further from compartment 350 along axis 373.

Extending out of cam and valve compartment 350, typically adjacent markers 368 is a vial adaptor port 370 configured to house vial adaptor 314 (FIGS. 1A-1B). Vial adaptor port 370 may include two or more vial adaptor guides 372 for guiding the vial adaptor 314 radially inward and outward relative to cam and valve compartment 350 along an axis 373, without changing the orientation of vial adaptor 314 relative to the housing portions, as explained hereinbelow with reference to FIGS. 17A-17F and 20A-20I. In some embodiments, such as the embodiment of FIGS. 3A-4C, the vial adaptor guides 372 comprise guiding protrusions, configured to cooperate with corresponding slots in vial adaptor 314. In other embodiments, such as the embodiment of FIGS. 5A-6C, the vial adaptor guides 372 comprise guiding slots, configured to cooperate with corresponding protrusions in vial adaptor 314.

A syringe rotation port 374 extends from cam and valve compartment 350 and spans approximately 90 degrees of the circumference thereof, from longitudinal alignment with the vial adaptor port 370 to longitudinal alignment with the needle compartment 340. As explained hereinbelow with reference to FIGS. 19A-20I, the syringe rotation port 374 is configured to allow rotation of a syringe connected to valve 550 between two operative positions, thereby driving rotation of the valve 550 between the two operative positions thereof. Disposed within port 374, at a position which is longitudinally aligned with needle compartment 340, is a valve guide 376 configured to ensure that the valve and needle do not move out of the housing 310 when the valve is not aligned with needle compartment 340, and to guide the valve and needle longitudinally out of the housing 310 when the valve and needle are being removed from the housing, as explained in further detail hereinbelow with reference to FIGS. 20A-21B. In the illustrated embodiments, the valve guide 376 comprises a protruding guide rail configured to cooperate with a recess in the valve 550.

Surrounding valve and cam compartment 350 and needle compartment 340, outside of ports 370 and 374, is a frame 378, configured to be connected to the frame 378 of the corresponding housing portion 310a or 310b or 310c and 310d, for example by mechanical engagement of protrusions 380a disposed on frame 378 of one of housing portions 310a and 310b in recesses 380b disposed in frame 378 of the other of housing portions 310a and 310b. In the embodiment of FIGS. 3A-4C the protrusions 380a and corresponding recesses 380b are pin connectors. By contrast, in the embodiment of FIGS. 5A-6C, the protrusions 380a and corresponding recesses 380b are differently shaped connectors. It is appreciated that housing portions 310a and 310b, and similarly housing portions 310c and 310d, may be connected to each other using any type of connection mechanism, such as snap fit engagement, adhesive, soldering, ultrasonic soldering, screws, nuts and bolts, or any other suitable connection mechanism.

In some embodiments, such as that shown in FIGS. 5A-6C, the exterior of housing portions 310c and 310d may include user grips 382, so as to provide the user with a convenient and comfortable location to grip housing 310 during use of system 309b without interfering with operation of system 309b.

Reference is now made to FIGS. 7A and 7B, which are pictorial illustrations of cam disk 312a forming part of the system 300a of FIGS. 1A and 2A, to FIGS. 8A, 8B, and 8C, which are, respectively, inner side view, top view, and outer side view planar illustrations of the cam disk 312a of FIGS. 7A and 7B, to FIGS. 9A and 9B, which are pictorial illustrations of cam disk 312c forming part of the system 300b of FIGS. 1B and 2B, and to FIGS. 10A, 10B, and 10C, which are, respectively, inner side view, top view, and outer side view planar illustrations of the cam disk 312c of FIGS. 9A and 9B.

It is appreciated that cam disks 312a and 312b, as well as cam disks 312c and 312d, are preferably mirror image symmetrical, such that any elements shown in FIGS. 7A to 8C for cam disk 312a are also included cam disk 312b and any elements shown in FIGS. 9A to 10C for cam disk 312c are also included in cam disk 312d, with suitable mirroring, even if not explicitly shown in drawings.

As seen, each of cam disks 312 comprises a generally circular disk and has a first, exterior surface 390 configured, when injection system 309a or 309b (FIGS. 1A-1B) is assembled, to face the housing portion 310 adjacent thereto, exterior surface 390 being shown with particular clarity in FIGS. 7A, 8C, 9A, and 10C. Each of cam disks 312 also includes a second, interior surface 392 configured, when injection system 309a or 309b (FIGS. 1A-1B) is assembled, to face the valve 550, interior surface 392 being shown with particular clarity in FIGS. 7B, 8A, 9B, and 10A.

Each of the cam disks 312 includes a throughgoing slot 394, configured, when the injection system 309 (FIGS. 1A-1B) is assembled, to allow rotation of disks 312 within compartment 350 of the housing portion 310 without interfering with fin 358 of the adjacent housing portion 310 (FIGS. 3A-6C) as explained hereinbelow with reference to FIGS. 17A-17F and 20A-20I.

Each of cam disks 312 further includes an integrally formed double sided, curved cam slot 396, configured, when injection systems 309a and 309b are assembled, to engage the vial adaptor 314 (FIGS. 1A-1B) and to move it radially along axis 373 (FIGS. 4A and 6A) away from and towards the center of the cam disk 312, as explained hereinbelow with reference to FIGS. 17A-17F and 20A-20I. In some embodiments, such as the embodiment of FIGS. 7A-8C, the cam slot 396 extends through the entire thickness of cam disks 312a and 312b, whereas in other embodiments, such as the embodiment of FIGS. 9A-10C, the cam slot 396 does not extend through exterior surface 390 of cam disk 312c and 312d.

As seen with particular clarity in FIGS. 8A, 8C, 10A, and 10C, cam slot 396 includes an outwardly pushing surface 396b which engages the vial adaptor 314 when moving the vial adaptor along axis 373 (FIGS. 4A and 6A) away from the center of disk 312, and an inwardly pushing surface 396a which engages the vial adaptor 314 when moving the vial adaptor along axis 373 towards the center of disk 312. Additionally, cam slot 396 includes at two ends thereof position stoppers 398a and 398b, configured to provide stability to the vial adaptor 314 when it is in each of the two positions, such that when vial adaptor 314 engages position stopper 398a it is in its outward most position and is further away from the center of disk 312 along axis 373, and when vial adaptor 314 engages position stopper 398b it is in its inward most position, engages the valve, and is closer to the center of disk 312 along axis 373.

Interior surface 392 has formed thereon a protruding valve guide 400, configured, when injection systems 309a and 309b are assembled, to engage valve core 320 (FIGS. 1A-1B) so as to convey rotation of the valve core 320 to rotation of the cam disk 312, to lock the valve core from being removed from housing 310 (FIGS. 3A-6C) when the valve 550 is in its first position, and, together with guide 376 of housing 310 (FIG. 3A), to guide the valve 550 and needle 316 (FIGS. 1A-1B) longitudinally out of the housing 310 when the valve and needle are being removed from the housing 310, as explained in further detail hereinbelow with reference to FIGS. 20A-21B.

In some embodiments, a blocking protrusion 402 protrudes from interior surface 392 of cam disk 312, adjacent positions stopper 398a of cam slot 396. Blocking protrusion 402 is configured, when injection systems 309a and 309b are assembled and when the vial adaptor 314 (FIGS. 1A-1B) engages position stopper 398a and is farthest from the center of disk 312 along axis 373, to prevent motion of the vial adaptor towards the center of disk 312 along axis 373, which motion is not caused by rotation of the disk, as explained hereinbelow with reference to FIGS. 20A-20I.

Turning specifically to the embodiment of FIGS. 7A to 8C, which is configured to cooperate with housing portions 310a and 310b shown in FIGS. 3A to 4C, it is seen that exterior surface 390 of cam disks 312a and 312b includes a tab 404 defined by a throughgoing U-shaped slot 406, and including a protrusion 408. Tab 404 is somewhat flexible and resilient, and is configured so that protrusion 408 may engage, and "click into", one of valve position markers 362 in housing 310a or 310b of FIGS. 3A-4C, thereby to provide a tactile and/or audible indication of the valve being stable in one of its two positions, and not being between positions. In some embodiments, protrusion 408 is colored and is visible to the user through the housing 310, such that when the protrusion 408 engages one of markers 362 the user may visually identify the current position of the valve, whether suitable for drawing liquid into or from a vial or for injection.

In the embodiment of FIGS. 9A to 10C, which is configured to cooperate with housing portions 310c and 310d shown in FIGS. 5A to 6C, it is seen that exterior surface 390 of cam disks 312c and 312d includes a painted valve position marker region 410, configured, when injection system 309b is assembled, to be visible through marker window 364 of housing 310 (FIGS. 5A-6C), such that when the valve 550 is in the first position, suitable for drawing liquid from or into a vial, the color of marker region 410 is visible through windows 364a in housing portions 310c and 310d, and when the valve 550 is in the second position, suitable for removal of the valve and needle from housing 310, the color of marker region 410 is visible through windows 364b in housing portions 310c and 310d.

Additionally, formed on a circumference of disks 312c and 312d at a 90 degree offset from one another, are a pair of tabs 414, each terminating in a hemispherical locking protrusion 416. The tabs 414 are somewhat flexible and resilient, and are configured so that each locking protrusion 416 may engage, and "click into", one of locking points 363 in housing portions 310c and 310d of FIGS. 5A-6C, thereby to provide a tactile and/or audible indication of the valve 550 being stable in one of its two positions, and not being between positions.

Reference is now made to FIGS. 11A, 11B, 11C, and 11D which are, respectively, top and bottom view pictorial illustrations, a side view planar illustration, and a sectional illustration of a vial adaptor 314 forming part of the systems 300a and 300b according to an embodiment of the teachings herein, the sectional illustration taken along section lines 11D-11D in FIG. 11C.

As seen in FIGS. 11A to 11D, vial adaptor 314 includes a generally circular base 420 having first and second base surfaces 420a and 420b opposing one another. Extending longitudinally outwardly, generally from the center of first base surface 420a, is a hollow tubular protrusion 422 having a fluid flow path 423 therethrough and defining a connector.

Extending longitudinally outwardly, generally from the center of second base surface 420b, is a hollow spike 428 defining a fluid path 430 therethrough. The fluid path 430 of spike 428 is in fluid flow communication with fluid path 423 of tubular protrusion 422. Extending longitudinally outwardly from a circumference of base 420 is a generally circumferential side wall 432 which at a suitable height thereof is split into a plurality of side wall segments 434 separated by gaps 436. Each of wall segments 434 terminates in a radially inwardly extending protrusion 438, which is adapted, in use, to engage a drug vial. In some embodiments, protrusions 438 are configured for irremovable snap-fit engagement with the drug vial, and in other embodiments the protrusions 438 are configured for releasable engagement with the neck of the drug vial. Furthermore, other embodiments may not include protrusions 438 at all, and/or have side wall 432 extend to the full height of the vial adaptor, without splitting into segments 434 and without defining gaps 436.

It is appreciated that the width of, or the number of degrees of the circumference covered by, each segment 434, as well as the width of, or number of degrees of the circumference covered by, each gap 436, may vary depending on the specific embodiment.

It will be appreciated by people of skill in the art, that the height of side wall 432, the width of segments 434, and the width of gaps 436, determine how difficult it would be for a user to remove a vial from the vial adaptor 314.

Extending radially outwardly from side wall 432 are a pair of pins 440, offset from one another by 180 degrees. When injection systems 309a and 309b (FIGS. 1A-1B) are assembled, pins 440 are configured to engage cam slot 396 of cam disks 312 (FIGS. 7A-10C) such that rotational movement of disks 312 is translated into vertical movement of vial adaptor 314 towards or away from the center of the cam disks 312, along axis 373 (FIGS. 4A and 6A). Additionally, at least the exterior surface of pins 440 may be colored such that in use pins 440 may be visible through markers 368 of housing 310 (FIGS. 3A-4C), so as to provide to the user an indication of the axial position of vial adaptor 314 relative to the housing 310.

Side wall 432 further includes a pair of guides 442, configured to cooperate with vial adaptor guides 372 of housing 310 (FIGS. 3A-6C) to guide the vial adaptor when moving axially along axis 373 within housing 310. In some embodiments, such as the illustrated embodiment, the guides 442 comprise slots configured to cooperate with protruding vial adaptor guides in the housing 310 (for example as shown in FIGS. 3A-4C). In other embodiments (not shown), the guides 442 comprise protruding rails configured to cooperate with vial adaptor guide slots in the housing 310 (for example as shown in FIGS. 5A-6C).

Figure 12C:
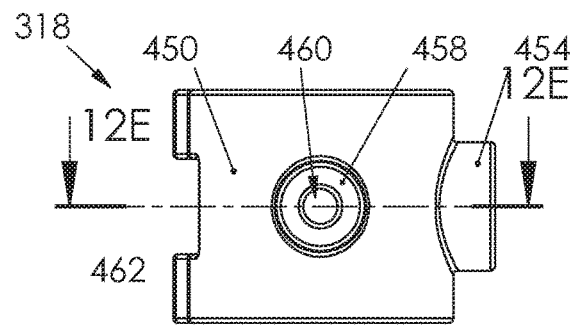
Figure 12D:
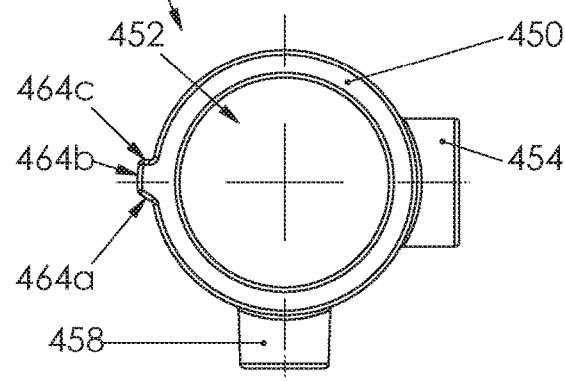
Figure 12E:
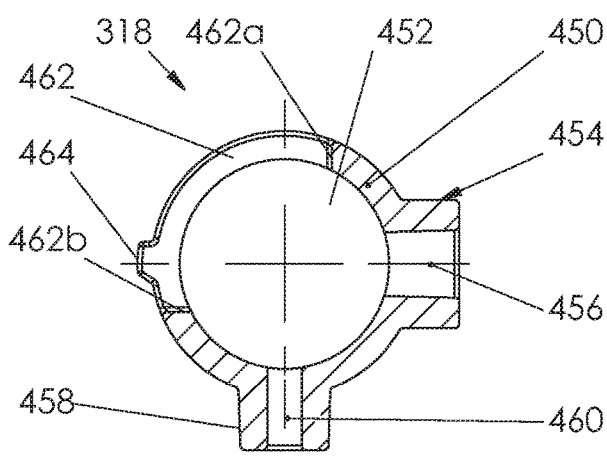

Reference is now made to FIGS. 12A, 12B, 12C, 12D, and 12E, which are, respectively, a side view pictorial illustration, a top view pictorial illustration, a side view planar illustration, a top view planar illustration, and a sectional illustration of valve housing 318 forming part of the systems 300a and 300b according to an embodiment of the teachings herein, the sectional illustration taken along section lines 12E-12E in FIG. 12C.

As seen, valve housing 318 comprises a generally cylindrical body portion 450 defining a central bore 452. A vial adaptor port 454 protrudes radially outwardly from body portion 450, and defines a fluid flow path 456 therein. When injection systems 309a and 309b (FIGS. 1A-1B) are assembled, vial adaptor port 454 is configured to reversibly engage vial adaptor 314, as explained in further detail hereinbelow. Protruding radially outwardly from body portion 450, and offset by 90 degrees from vial adaptor port 454, is a needle port 458 defining a fluid flow path 460 therein. When injection system 309a and 309b (FIGS. 1A-1B) are assembled, needle port 458 is configured to permanently and irremovably engage needle 316 (FIGS. 1A-1B). Both fluid flow path 456 and fluid flow path 460 are in fluid flow communication with bore 452.

It is appreciated that in some embodiments, needle 316 and valve housing 318 may be produced as a unitary element, such that they are permanently connected to one another at needle port 458. In other embodiments, the needle 316 may be connected to the needle port 458 of the valve housing 318 by the end user, for example when the needle is a typical hypodermic needle, and can be connected to the valve following removal of the valve 550 and a syringe connected thereto from housing 310 as seen in FIGS. 21A-21B.

A throughgoing slot 462 is defined in body portion 450. The slot 462 spans approximately 90 degrees of the circumference of the body portion, and has one end 462a generally offset by 180 degrees from needle port 458, and a second end 462b generally offset by 180 degrees from vial adaptor port 454. Slot 462 is configured to allow for rotation of a syringe functionally associated with the valve core 320 (FIGS. 1A-1B) between the second end 462b, wherein the syringe is aligned with and in fluid flow communication with vial adaptor port 454, and the first end 462a, wherein the syringe is aligned with and in fluid flow communication with needle port 458.

Extending radially outwardly from body portion 450, on either side of slot 462 near end 462b thereof, are a pair of locking protrusions 464, defining a first surface 464a facing end 462b of slot 462, a second surface 464b facing radially outwardly from body portion 450, and a third surface 464c facing end 462a of slot 462. In use, locking protrusions 464 are configured to engage surfaces of valve driver 322 (FIGS. 1A-1B) so as to prevent undesired rotation of the valve, as explained in detail with reference to FIGS. 17A-17F and 20A-20I. As seen with particular clarity in FIGS. 12D and 12E, surface 464c generally forms a right angle with the exterior surface of housing 450 and with surface 464b. However, surface 464a forms an obtuse angle with surface 464b and with the exterior surface of housing 450, the significance of which is explained in detail hereinbelow with reference to FIG. 17C.

Reference is now made to FIGS. 13A, 13B, 13C, and 13D, which are, respectively, two side view pictorial illustrations, a side view planar illustration, and a sectional illustration of valve core 320 forming part of systems 300a and 300b according to an embodiment of the teachings herein, the sectional illustration taken along section lines 13D-13D in FIG. 13C.

As seen, valve core 320 comprises a solid cylindrical body portion 470 having a bore 472 extending therethrough in a direction transverse to the longitudinal axis of the body portion 470. In some embodiments, bore 472 may be internally tapered or may include multiple circumferences therein, as shown in FIG. 13D, such that a first port thereof 474 has a smaller circumference than a second port thereof 476.

In some embodiments, an elongate slot 478 is cut out of cylindrical body portion 470 and extends along at least part of bore 472 starting at port 476. In some embodiments, port 476 is surrounded by an angular, and in some embodiments, square, recess 480 in body portion 470.

Extending longitudinally outwardly from body portion 470 at the top and bottom ends thereof, along a portion of the circumference of body portion 470, are two pairs of guiding protrusions 482. Protrusions 482 each include two planar, non-curved, shoulder surfaces 484 on either end thereof. In use, valve guides 400 of cam disks 312 (FIGS. 7A to 10C) are configured to be disposed between protrusions 482 and to engage shoulder surfaces 484, so as to transfer rotational motion of the valve core 318 to cam disks 312. Additionally, engagement between the protrusions 482 and valve guides 400 of cam disks 312 prevents the user from removing the valve 550 from the housing 310 when the valve is not aligned with the needle 316, and guides the valve and needle out of the housing 310 smoothly along the guides 400 and along guide 376 of the housing 310 (FIGS. 3A-6C) when the valve is aligned with the needle.

Reference is now made to FIGS. 14A, 14B, 14C, and 14D, which are, respectively, a pictorial illustration, a front view planar illustration, a top view planar illustration, and a sectional illustration of a valve driver 322 forming part of the systems 300a and 300b according to an embodiment of the teachings herein, the sectional illustration taken along section lines 14D-14D in FIG. 14B.

As seen, valve driver 322 comprises a hollow elongate body portion 490 arranged along a longitudinal axis 492. At a distal end thereof, body portion 490 includes a female luer connector 494, which may be threaded as shown in the illustrated embodiment, or may include any other type of suitable connector, and defines a fluid flow path 495 therein. In some embodiments, a generally circular guard disk 496, aligned with axis 492, is disposed along the luer connector 494 towards a proximal end thereof. In some embodiments, the guard disk 496 has a circumference greater than that of luer connector 494, and is configured to guide the user to rotate the valve 550 by holding a syringe connected thereto, rather than by holding the valve itself.

Extending proximally to luer connector 494 and guard disk 496 along longitudinal axis 492 is a valve core connector portion including an polygonal portion 500, here shown as a square portion, configured to be seated within recess 480 of valve core 320 (FIGS. 13A-13D) and to prevent rotation of the valve driver 322 relative to valve core 320 when the two are connected. Disposed proximally to angular portion 500 is a hollow tubular portion 502 having an elongate rib 504 formed on an exterior thereof. Tubular portion 502 and rib 504 are configured to be seated within bore 472 and slot 478 of valve core 320 (FIGS. 13A-13D), respectively, to enable the user to drive rotation of the valve core by interaction with the valve driver 322 while preventing rotation of the valve driver 322 relative to the valve core 320. Polygonal portion 500 and tubular portion 502 together define a fluid flow path 506, which is in fluid flow communication with flow path 495 of luer connector 494.

Extending outwardly from elongate body portion 490, generally at a sharp angle relative to longitudinal axis 492, is a flexible leaf spring 510. Leaf spring 510 is generally curved, and is configured to extend about the exterior of valve housing 318 (FIGS. 12A-12E) as explained hereinbelow with respect to FIGS. 15A-16E. Extending from the end of leaf spring 510 on either side thereof are legs 512, each terminating in a protrusion 514 extending outwardly therefrom in a direction perpendicular to longitudinal axis 492. Protrusions 514 each define a proximally facing surface 516 and an inwardly facing surface 517, which are configured to engage protrusions 464 of the valve housing 318 (FIGS. 12A-12E) in one position thereof as explained hereinbelow. At an end thereof adjacent guard 496, leaf spring 510 includes legs 522, each terminating in an angled surface 526, which is configured to engage protrusions 464 of valve housing 318 in another position of the valve, as explained hereinbelow.

Reference is now made to FIGS. 15A, 15B, 15C, 15D, and 15E, which are, respectively, an exploded view illustration, a pictorial illustration, a side view planar illustration, and two sectional illustrations of a valve 550 comprising valve housing 318, valve core 320, and valve driver 322 according to an embodiment of the teachings herein, in a first valve position suitable for connection to a medicine vial, the sectional illustrations taken along respective section lines 15D-15D and 15E-15E in FIG. 15C, and to FIGS. 16A, 16B, 16C, 16D, and 16E, which are, respectively, an exploded view illustration, a pictorial illustration, a side view planar illustration, and two sectional illustrations of the valve 550 in a second valve position suitable for fluid communication with needle 316, the sectional illustrations taken along respective section lines 16D-16D and 16E-16E in FIG. 16C.

As seen, when valve 550 is constructed, valve core 320 slidingly fits within bore 452 of valve housing 318 such that the exterior of valve core body portion 470 sealingly engages an interior wall of valve housing body portion 450.

Additionally, the valve core connector portion of the valve driver 322 is disposed within bore 472 of the valve core, such that tubular portion 504 is seated within bore 472 adjacent port 476 thereof, rib 504 of valve driver 322 is disposed within slot 478 of the valve core 320, and at least part of polygonal portion 500 of the valve driver 322 is disposed within recess 480 of the valve core 320. Engagement of rib 504 with slot 478 and of polygonal portion 500 with recess 480 ensures that rotation of the valve driver 322 will result in rotation of valve core 320, and not in a change of relative positioning between the valve driver 322 and the valve core 320. It is appreciated that tubular portion 502 is inserted into bore 472 though slot 462 in valve housing 318, such that tubular portion 502 is free to rotate within slot 462, and such that luer connector 494 of valve driver 322 extend out of valve housing 318, is accessible for connection of a corresponding luer connector thereto, and may be used as a handle for driving rotation of valve driver 322 within valve housing 318. Furthermore, spring leaf 510 of valve driver 322 extends about part of an exterior surface of body portion 450 of valve housing 318.

It is appreciated that the engagement between bore 472 with the tubular portion 502 of valve driver 322 causes rotation of the valve driver 322 within slot 462 of the valve housing 318, for example by rotation of luer connector 494 thereof or an element connected thereto, to result in corresponding rotation of valve core 320.

Turning specifically to the first valve position shown in FIGS. 15A to 15E, as seen with particular clarity in FIG. 15D, bore 472 of the valve core and tubular portion 502 disposed therein are aligned with vial adaptor port 454 of valve housing 318, such that fluid flow path 495 of luer connector 494, fluid flow path 506 of tubular portion 502, bore 472 and port 474 thereof, and fluid flow path 456 of vial adaptor port 454 are all in fluid flow communication, and fluid can flow freely therethrough. By contrast, in this valve position, there is no fluid flow path between bore 472 of the valve core 320 and needle port 458 of the valve housing 318, as seen in FIG. 15E.

Turning specifically to FIG. 15C, it is seen that leaf spring 510 of the valve driver 322 surrounds the exterior of housing portion 450 of the valve housing 318, such that angled surface 526 of the leaf spring engage angled surfaces 464a of protrusions 464 of housing portion 450, thereby to provide mild resistance to turning of the valve driver and valve to the second position (shown in FIGS. 16A-16E). However, the engagement of surfaces 526 and 464a does not lock the valve driver 322 relative to the valve housing 318 or prevent rotation of the valve core 320.

Turning now to the second valve position shown in FIGS. 16A to 16E, as seen with particular clarity in FIG. 16E, bore 472 of the valve core and tubular portion 502 disposed therein are aligned with needle port 458 of valve housing 318, such that fluid flow path 495 of luer connector 494, fluid flow path 506 of tubular portion 502, bore 472 and port 474 thereof, and fluid flow path 460 of needle port 458 are all in fluid flow communication, and fluid can flow freely therethrough. By contrast, in this valve position, there is no fluid flow path between bore 472 of the valve core and vial adaptor port 454 of the valve housing, as seen in FIG. 16D.

Turning specifically to FIG. 16C, it is seen that leaf spring 510 of the valve driver 322 has rotated about the exterior of housing portion 450 of the valve housing 318 away from needle port 458, such that now surfaces 516 of the leaf spring engage surfaces 464c of protrusions 464 of housing portion 450, thereby to lock the valve driver 322, and consequently the valve core 320, from being rotated relative to the valve housing 318 back to the first valve position (shown in FIGS. 15A-15E).

It is appreciated that the following description of FIGS. 17A-21B relates to the process of use of injection system 309a, shown in FIGS. 1A and 2A. However, the embodiment of injection system 309b has a substantially similar structure, and thus a substantially similar process of use.

Reference is now made to FIGS. 17A, 17B, 17C, 17D, 17E, and 17F, which are, respectively, a pictorial illustration, a side view planar illustration, a partially cutaway side view planar illustration, and three sectional illustrations of an injection system 309a of FIGS. 1A and 2A, in an initial operational position, the sectional illustrations 17D and 17E taken along respective section lines and directions 17D-17D and 17E-17E in FIG. 17C, and sectional illustration 17F taken along section lines 17F-17F in FIG. 17B.

It is appreciated that FIG. 17C is a planar side view figure of the system 309, having housing portions 310a cam disk 312a (FIGS. 1A-1B) removed therefrom, so as to clearly illustrate the interactions between the valve components 318, 320, and 322, the vial adaptor 314, the needle 316, the cam disks 312 (shown by a single cam disk), and the housing 310 in the initial operational position of the injection system 309. It is further appreciated that the orientation of cam disk 312a not shown in FIG. 17C is entirely symmetrical to the position of cam disk 312b shown in the Figure, and similarly the orientation of housing portion 310a not shown in FIG. 17C is symmetrical to the position of housing portion 310b shown therein.

As seen clearly in FIG. 17C, in the initial operational position, cam disks 312 and a valve 550 constructed of valve housing 318, valve core 320, and valve driver 322 as described hereinabove with reference to FIGS. 15A to 15E, is disposed within cam and valve compartment 350 of housing 310. Needle 316 is disposed within needle compartment 340 of housing 310. Vial adaptor 314 is disposed in vial adaptor port 370 of housing 310, such that connector 422 of the vial adaptor sealingly engages vial adaptor port 454 of valve housing 318. Additionally, pins 440 of vial adaptor 314 are disposed within cam slots 396 of cam disks 312 (also seen in FIG. 17D), and are located in position stopper 398b thereof (position stopper 398b is positioned behind vial adaptor 314). As such, the cam disks 312 are oriented such that valve guides 400 are substantially aligned with vial adaptor 314 as seen in FIG. 17E.

As mentioned above with respect to FIGS. 15A-15E, and as seen in FIG. 17C, in the first position of valve 550, angled surfaces 526 of the leaf spring 510 of valve driver 322 engage angled surfaces 464a of protrusions 464 of valve portion 318, thereby to provide mild resistance to turning of the valve driver and consequently the valve. Turning specifically to FIG. 17D, it is seen that the valve 550 is in the orientation shown in FIGS. 15A-15E, such that luer connector 494 of valve driver 322 is in fluid flow communication with spike 428 of vial adaptor 314. Specifically, an uninterrupted fluid flow path exists between flow path 495 of luer connector 494 and fluid path 430 of spike 428 via fluid flow path 506 of tubular portion 502 of valve driver 322; bore 472 of valve core 320; and fluid flow path 423 of connector 422 of vial adaptor 314, which is disposed within opening 456 of vial adaptor port 454 of valve housing 318.

As mentioned above, pins 440 of vial adaptor 314 are disposed within cam slots 396 and are disposed at stopper positions 398*b* thereof, and the cam disks 312 are oriented such that pins 440 are aligned with the first, inner one of vial adaptor position markers 368*a* indicative of the vial adaptor being at a position closer to valve 550 and engaging port 454. As seen in FIGS. 17A and 17B, the color of the tips of pins 440 of the vial adaptor 314 is visible to the user via marker 368*a*. In some embodiments, color is visible to the user via user feedback window 364*a* showing a medicine vial.

Turning to FIG. 17E, it is seen that a connector of needle 316 is connected to needle port 458 of valve housing 318 and forms a fluid flow path between a tip 560 of needle 316 and flow path 460 of port 458. However, as seen, no flow path exists between bore 472 of valve core 320 or flow path 506 of valve driver 322 and needle 316. It is further seen that valve guides 400 of cam disks 312 are disposed between protrusions 482 of valve core 320. As such, the valve guides 400 prevent the needle 316 and valve 550 from being moved in a direction away from wall portion 346 of housing 310, the direction shown by arrow 552. Additionally, the mechanical engagement between valve core 320 and cam disks 312 via engagement of valve guides 400 with protrusions 482 ensures that rotation of valve core 320 will result in corresponding rotation of cam disks 312, as explained in further detail hereinbelow.

Looking now at the view shown in FIG. 17F, it is seen that while pins 440 of vial adaptor 314 are visible in markers 368*a* of housing 310, protrusions 408 of marker tabs 404 of cam disks 312 engage and rest within a first valve position marker 362 of housing 310, such that the user may receive a visual indication of the system being in position for drawing fluid from, or injecting fluid into, a medical vial if one were connected to vial adaptor 314. In embodiments in which housing 310 includes user feedback windows 364, visual feedback may also be provided to the user in window 364*a* illustrating a medicine vial, as shown in FIGS. 17A and 17B.

Reference is now made to FIGS. 18A and 18B, which are, respectively, a side view planar illustration and a sectional illustration of the injection system 309*a* in a vial connection operational position, the sectional illustration taken along section lines 18B-18B in FIG. 18A.

As seen, a user has inserted a medicine vial 562 into vial adaptor 314 by pushing the vial into the vial adaptor as known in the art. The medicine vial 562 may be any suitable, typically sized, medical vial, and includes a head portion 564 sealed by a seal 566, a neck portion 568, and a body portion 570.

As seen with particular clarity in FIG. 18B, following connection of the vial adaptor 314 to the vial 562, spike 428 of vial adaptor 314 has punctured seal 566 of the vial, such that the medicament or diluent included within body portion 570 of the vial is in fluid flow communication with flow path 495 of luer connector 494 of valve driver 322, via path 430 of spike 428 and path 423 of connector 422 of vial adaptor 314, bore 472 of valve core 320, and flow path 506 of valve driver 322.

Additionally, segments 434 of the circumferential wall of vial adaptor 314 are disposed about head portion 564 of vial 562, such that protrusions 438 of the segments 434 engage head portion of the vial. In some embodiments, the engagement between the protrusions 438 and the head portion of the vial is reversible, and the vial may be removed from the vial adaptor 314, whereas in other embodiments the engagement therebetween is irremovable.

Aside from connection of vial 562 to vial adaptor 314, no other changes occur to any of the components of injection system 309 relative to the position illustrated in FIGS. 17A-17F.

Reference is now made to FIGS. 19A and 19B, which are, respectively, a side view planar illustration and a sectional illustration of injection system 309*a* in a syringe connection and medicine reconstitution or transfer operational position, the sectional illustration taken along section lines 19B-19B in FIG. 19A.

As seen, the user connects a suitably sized syringe 580 to female luer connector 494 of valve driver 322, such that the interior of syringe 580 is in fluid flow communication with the medicament or diluent disposed in vial 562 via flow paths 495, 506, 423, and 430 and bore 472, substantially as described hereinabove with reference to FIGS. 18A and 18B. In some embodiments, syringe 580 includes a male luer connector 582 which is connected to the female luer connector 494 of valve driver 322. Once the syringe 580 is connected to valve driver 322, the user may pull a plunger 584 of syringe 580 distally to draw the medicament from vial 562.

It is appreciated that in some embodiments, drawing the medicament from the vial 562 may include additional steps, such as, prior to connecting the syringe 580 to injection system 309 drawing water or another liquid into the syringe, following connection of the syringe and the injection system injecting the liquid from the syringe into the vial 562, mixing the content of the vial 562 with the injected liquid to form a solution or suspension, and drawing the formed solution or suspension back into the syringe as a medicament, and/or any other steps required in other drug preparation protocols known in the art.

Aside from connection of syringe 580 to valve driver 322, no other changes occur to any of the components of injection system 309 relative to the positions illustrated in FIGS. 17A-17F and 18A-18B.

Reference is now made to FIGS. 20A, 20B, 20C, 20D, 20E, 20F, 20G, 20H, and 20I, which are, respectively, a side view planar illustration, a partially cut away side view planar illustration, an enlarged view of a portion of FIG. 20B, four sectional illustrations, a partially cut away top view planar illustration, and another sectional illustration of injection system 309*a* in a syringe rotation and needle fluid communication operational position, wherein sectional illustrations 20D and 20E are taken along respective section lines 20D-20D and 20E-20E, sectional illustration 20F is taken along section lines 20F-20F in FIG. 20C, and sectional illustrations 20G and 20I are taken along respective section lines 20G-20G and 20I-20I in FIG. 20H.

It is appreciated that FIG. 20B is a side view planar illustration and FIG. 20H is a top view planar illustration of the system 309*a*, having housing portions 310*a* cam disk 312*a* (FIGS. 1A-1B) removed therefrom, so as to clearly illustrate the interactions between the valve components 318, 320, and 322, the vial adaptor 314, the needle 316, the cam disks 312 (shown by a single cam disk), and the housing 310 in the needle fluid communication operational position of the injection system 309. It is further appreciated that the orientation of cam disk 312*a* not shown in FIGS. 20B and 20H is entirely symmetrical to the position of cam disk 312*b* shown in the FIGS. 20B and 20H, and similarly the orientation of housing portion 310a not shown in FIGS. 20B and 20H is symmetrical to the position of housing portion 310b shown therein.

As seen from comparison of FIGS. 19A and 20A, the user has rotated syringe 580 by an angle of 90 degrees in the direction indicated by arrow 588, such that the syringe 580 is now aligned with needle compartment 340 of the housing 310. The rotation is made possible by the 90 degree breadth of syringe rotation port 374 of housing 310, as seen in FIG. 20B.

As seen in FIG. 20B, following rotation of syringe 580 to be aligned with needle compartment 340, valve 550 has rotated from the position shown in FIGS. 15A-15E to the position shown in FIGS. 16A-16E under the driving force of valve driver 322. Specifically, rotation in direction 588 of syringe 580 which is connected to luer connector 494 of valve driver 322 results in corresponding rotation of the valve driver 322. Such rotation causes corresponding 90 degree rotation of the valve core 320, such that bore 472 thereof is now aligned with needle port 458 of valve housing 318. As such, as seen with particular clarity in FIG. 20E, syringe 580 is now in fluid flow communication with tip 560 of needle 316 via flow path 495 of luer connector 494 and flow path 506 of tubular portion 502 of valve driver 322, bore 472 of valve core 320, and flow path 460 of needle port 458 of valve housing 318. Consequently, no flow path exits between bore 472 of valve core 320 and vial adaptor 314, as seen in FIG. 20D.

As seen in FIG. 20B, rotation of syringe 580 and corresponding rotation of valve core 320 further drives rotation of cam disks 312, such that pins 440 of vial adaptor 314 ride along pushing surface 396a of cam slot 396 to position stopper 398a, whereby the vial adaptor is moved axially away from the center of the valve 550. As a result, the tubular protrusion 422 of vial adaptor 314 is disconnected from vial adaptor port 454 of valve housing 318, as seen clearly in FIG. 20D. Additionally, pins 440 of the vial adaptor 314 are now visible through the second, external one of vial adaptor position markers 368b indicative of the vial adaptor being at a position further from, and disconnected from, valve 550, as seen in FIG. 20A. However, it will be appreciated that in some embodiments the vial adaptor 314 is permanently fixed to vial adaptor port 454 of valve housing 318, and does not disconnect therefrom.

Rotation of cam disks 312 also results in valve guides 400 of the cam disks 312 being suitably aligned for guiding the removal of valve 550 and needle 316 attached thereto from housing 310, as seen in FIGS. 20D and 20I. As seen from the combination of FIGS. 20D, 20F, and 20I, following rotation of cam disks 312, the valve guides 400 thereof are aligned with valve guides 376 of housing portions 310, such that the system 309 ensures that when the user removes syringe 580 together with the valve 550 and needle 316 from the housing 310, they will be removed smoothly and in a straight line. As explained hereinabove with reference to FIGS. 15A-16B rotation of valve driver 322 driven by rotation of syringe 580 results in spring leaf 510 of the valve driver 322 being pushed radially outward to extend about protrusions 464 of valve housing 318, as seen with clarity in FIG. 20B and in the enlarged portion thereof shown in FIG. 20C. As seen clearly in FIGS. 20C, 20G, and 20I, until the valve 550 and needle 316 are moved longitudinally in a direction away from wall portion 346 of housing 310, distally facing surfaces 517 of protrusions 514 engage the long surfaces of fins 358 of housing 310 extending through slots 394 of cam disks 312, and prevent the protrusions 514 of spring leaf 510 from locking against protrusions 464 of valve housing 318 as shown in FIGS. 16A-16E.

Consequently, should the user wish to return system 309 to the medicine transfer position shown in FIGS. 19A and 19B, all the user has to do is rotate the syringe back 90 degrees, in a direction opposite from direction 588 shown in FIG. 20A, which would result in corresponding rotation of valve driver 322, valve core 320, and cam disks 312. Because the spring leaf 510 is not locked onto protrusions 464 of valve housing 318, such rotation of valve driver 322 would result in protrusions 514 of the spring leaf 510 travelling along fin 358 back to their initial position shown in FIGS. 19A and 19B. Corresponding rotation of cam disks 312 would also result in repositioning of vial adaptor 314 into port 454 of valve housing 318.

As seen clearly in FIG. 20D, when system 309a is in the needle fluid communication position of FIGS. 20A-20I, blocking protrusions 402 of cam disks 312 are disposed adjacent surface 420a of base 420 of vial adaptor 314, and prevent motion of vial adaptor 314 toward vial adaptor port 454 of valve 550 under force applied to the vial 562. As such, the only way for the user to return to the initial position of system 309 is by rotation of syringe 580 as explained herein. In such a case, rotation of cam disks 312 back to the position of FIGS. 17A-17F would cause pins 440 of vial adaptor 314 to travel along inwardly pushing surfaces 396a of cam slot 396, back to stopper position 398b thereof.

Reference is now made to FIGS. 21A and 21B, which are, respectively, a side view planar illustration of needle 316, valve 550, and syringe 580 following removal thereof from housing 310 of injection system 309a and ready for injection, and an enlarged view of a portion of FIG. 21A.

As seen, removal of the needle 316, valve 550, and syringe 580 from housing 310 results in disengagement of protrusions 514 of leaf spring 510 of valve driver 322 from fins 358 of cam disks 312, and consequently leaf spring 510 springs towards housing portion 450 of valve housing 318. As a result, proximal surfaces 516 of protrusions 514 lock against surfaces 464c of protrusions 464 of valve housing 318, such that the valve driver, and consequently the valve core 320 and syringe 580, cannot be rotated relative to the valve housing 318.

In the position of FIGS. 21A and 21B, the user would bring the proximal portion 590 of needle 316 close to the injection site, and would proceed to inject the contents of the syringe into the site as known in the art.

The following description relates to FIGS. 22 to 35B, and describes a system for interfacing between a syringe, a drug vial, and a needle according to another embodiment of the teachings herein. It is appreciated that many aspects of the embodiment of FIGS. 22-35B are substantially the same as the corresponding aspects of the embodiments of FIGS. 1A-21B. As such, elements in the embodiment of FIGS. 22-35B were given identical reference numerals, or similar reference numerals, to the corresponding elements in the embodiments of FIGS. 1A-21B.

Figure 23:
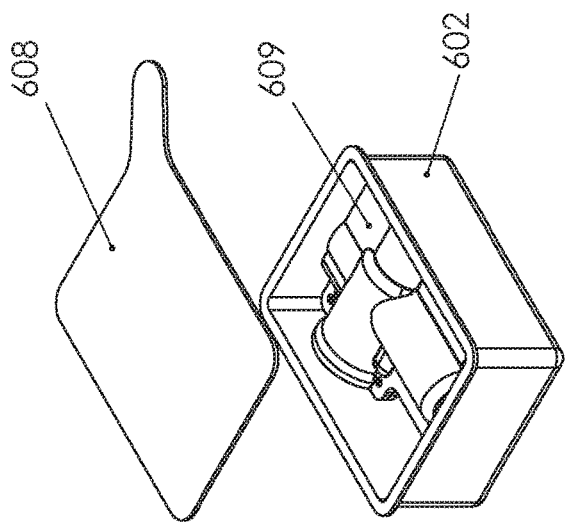
FIG. 23 is a simplified pictorial illustration of the system of FIG. 22, as assembled, according to an embodiment of the teachings herein.
Figure 22:
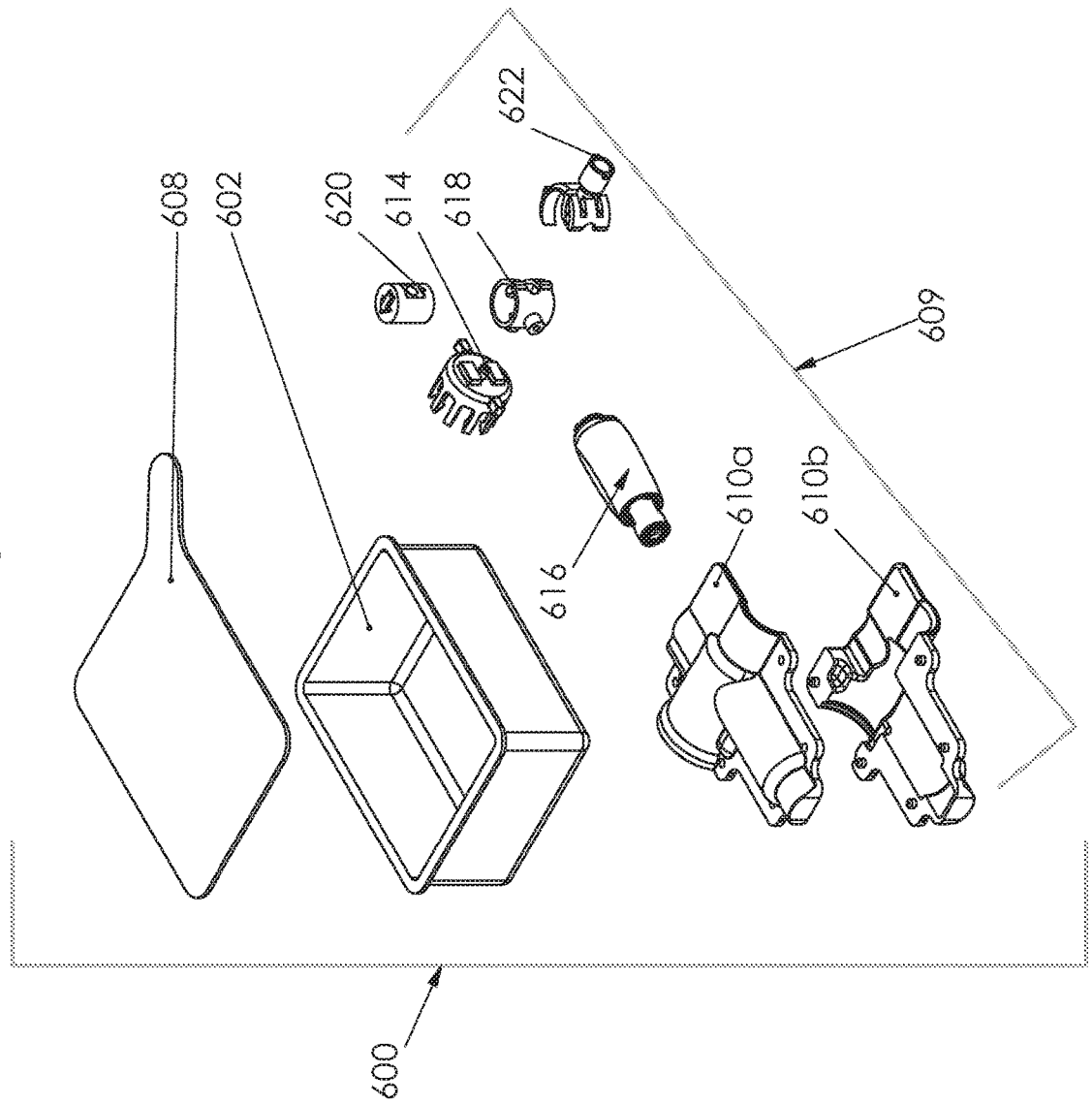
FIG. 22 is an exploded view illustration of a system for interfacing between a syringe, a drug vial, and a needle, according to another embodiment of the teachings herein.

Reference is now made to FIG. 22, which is an exploded view illustration of a system 600 for interfacing between a syringe, a drug vial, and a needle, according to another embodiment of the teachings herein, and to FIG. 23, which is a simplified pictorial illustrations of the system 600 of FIG. 22 as assembled.

As seen in FIGS. 22 and 23, the system 600 according to the teachings herein includes a casing 602 associated with a seal 608 substantially identical to those described hereinabove with reference to FIGS. 1A-2B. The casing 602 houses an injection system 609 including a housing 610 defined by a pair of housing portions 610a and 610b, a vial adaptor 614, a needle 616, a valve housing 618, a valve core 620, and a valve driver 622.

Housing portions 610a and 610b may be any suitable housing portions, for example as described hereinbelow with reference to FIGS. 24A to 24C. As explained in further detail hereinbelow, housing portions 610a and 610b are generally mirror image symmetric, such that the housing portions symmetrically engage each other while enclosing other components of the injection system 609.

The vial adaptor 614 may be any suitably configured vial adaptor, for example as described hereinbelow with reference to FIGS. 25A to 25D. The needle 616 is substantially identical to needle 316 described hereinabove, and may be any suitable needle, including a standard hypodermic needle, a safety needle, or an automatic injection needle.

The valve housing 618 may be any suitable valve housing, for example as described hereinbelow with reference to FIGS. 26A to 26E. The valve core 620 may be any suitable valve core, for example as described hereinbelow with reference to FIGS. 27A to 27D. The valve driver 622 may be any suitable valve driver, for example as described hereinbelow with reference to FIGS. 28A to 28C. As explained in further detail hereinbelow with reference to FIGS. 29A to 30E, valve housing 618, valve core 620, and valve driver 622 together form a valve which can assume two operative valve positions.

Reference is now made to FIGS. 24A, 24B, and 24C, which are pictorial illustrations of housing portions 610a and 610b forming part of the system 600, and an inner side view planar illustration of housing portion 610a.

It is appreciated that housing portions 610a and 610b are generally mirror image symmetrical, such that, other than connector elements, any elements included in one of the housing elements are included in the other of the housing elements as well, even if not clearly visible in the drawings of the other housing element.

Housing portions 610a and 610b are substantially similar to housing portions 310a and 310b described hereinabove with reference to FIGS. 3A-4C. As such, housing portions 610a and 610b include a needle compartment 640 including portions 642a and 642b and wall portions 644 and 646 (similar to corresponding needle compartment 340, portions 342a and 342b, and wall portions 344 and 346), a vial adaptor port 670 including vial adaptor guides 672 (similar to port 370 and guides 372), a syringe rotation port 674 (similar to port 374), and a frame 678 connected by connection of protrusions 680a to recesses 680b (similar to frame 378, protrusions 380a, and recesses 380b). Housing portions 610a and 610b include a valve compartment 650, configured to have seated therein a valve formed of valve housing 618, valve core 620, and valve driver 622. Valve compartment 650 is generally tubular, and is suited to the structure of the valve as described hereinbelow with reference to FIGS. 29A-30E.

Housing portions 610a and 610b differ from the corresponding housing portions 310a and 310b of FIGS. 3A-4C in that they do not include a combined cam and valve compartment (350 in FIGS. 3A-4C) and all elements included in the cam and valve compartment, such as a fin, valve position markers, and vial adaptor position markers. Additionally, housing portions 610a and 610b do not include a valve guide (376 in FIGS. 3A-4C).

Reference is now made to FIGS. 25A, 25B, 25C, and 25D which are, respectively, top and bottom view pictorial illustrations, a side view planar illustration, and a sectional illustration of a vial adaptor 614 forming part of the system 600 according to an embodiment of the teachings herein, the sectional illustration taken along section lines 25D-25D in FIG. 25C.

Vial adaptor 614 is substantially similar to vial adaptor 314 described hereinabove with reference to FIGS. 11A-11D. As such, vial adaptor 614 includes: a base 720 including surfaces 720a and 720b (similar to corresponding base 420); a connector 722 defining a flow path 723 (similar to connector 422 and path 423); a spike 728 defining a flow path 730 (similar to spike 428 and path 430); a side wall 732 (similar to wall 432); and wall segments 734 separated by gaps 736 and terminating in protrusions 738 (similar to segments 434, gaps 436, and protrusions 438).

Extending radially outwardly from side wall 732 are a pair of pins 740, similar to pins 440 (FIGS. 11A-11D) but having a generally square cross section. When injection system 609 (FIG. 22) is constructed, pins 740 are configured to engage vial adaptor guides 672 in housing 610.

Surface 720a of vial adaptor 614 has mounted thereon, on either side of connector 722, a protruding contact surface 744 configured, when injection system 609 is constructed, to engage the valve driver 622 as explained hereinbelow with reference to FIGS. 31A-31D and 34A-34D.

Reference is now made to FIGS. 26A, 26B, 26C, 26D, and 26E, which are, respectively, a side view pictorial illustration, a top view pictorial illustration, a side view planar illustration, a top view planar illustration, and a sectional illustration of valve housing 618 forming part of the system 600 according to an embodiment of the teachings herein, the sectional illustration taken along section lines 26E-26E in FIG. 26C. Valve housing 618 is substantially similar to valve housing 318 described hereinabove with reference to FIGS. 12A-12E. As such, valve housing 618 includes: a body portion 750 defining a bore 752 (similar to body portion 450 and bore 452); a vial adaptor port 754 defining a flow path 756 (similar to port 454 and path 456); a needle port 758 defining a flow path 760 (similar to port 458 and path 460); a slot 762 having ends 762a and 762b (similar to slot 462); and locking protrusions 764 defining surfaces 764a, 764b, and 764c (similar to protrusions 464).

The main differences between valve housing 618 and valve housing 318 (FIGS. 12A-12E) is in that the cross section of vial adaptor port 754 is generally oval or rectangular, whereas the cross section of the corresponding port of valve housing 318 is generally circular, and that ends 762a and 762b are generally rounded, whereas the corresponding slot ends of valve housing 318 are generally square. It is appreciated that these are simple design features and considerations, and that in all functional aspects the two valve housings are substantially identical.

Reference is now made to FIGS. 27A, 27B, 27C, and 27D, which are, respectively, two side view pictorial illustrations, a side view planar illustration, and a sectional illustration of valve core 620 forming part of system 600 according to an embodiment of the teachings herein, the sectional illustration taken along section lines 27D-27D in FIG. 27C.

Valve core 620 is substantially similar to valve core 320 described hereinabove with reference to FIGS. 13A-13D. As such, valve core 620 includes: a body portion 770 defining a bore 772 having ports 774 and 776 (similar to body portion 470, bore 472, and ports 474 and 476); and a recess 780 (similar to recess 480).

Valve housing 618 does not include protrusions at ends thereof, or an elongate slot along the bore thereof. Additionally, valve housing 618 includes a visual indicator 786, here shown as an arrow, providing to the user an indication of the direction in which the valve is aligned. It is appreciated that in all functional aspects relating to the rotation of the valve between two positions, valve core 620 and corresponding valve core 320 are substantially identical.

Reference is now made to FIGS. 28A, 28B, and 28C, which are, respectively, a pictorial illustration, a front view planar illustration, and a sectional illustration of a valve driver 622 forming part of the system 600 according to an embodiment of the teachings herein, the sectional illustration taken along section lines 28C-28C in FIG. 28B.

Certain aspects of valve driver 622 are substantially similar to valve driver 322 described hereinabove with reference to FIGS. 14A-14C. As such, valve driver 622 includes: luer connector 794 defining a flow path 795 (similar to connector 494 and path 495); and valve core connector including polygonal portion 800, and tubular portion 802 defining flow path 806 therein (similar to polygonal portion 500, tubular portion 502, and flow path 506).

Valve driver 622 does not include a guard disk between the luer connector and valve core connector, and does not include an elongate rib, since the corresponding valve core bore does not include an elongate channel for accommodating such a rib.

The flexible leaf spring 520 of valve driver 322 (FIGS. 14A-14C) is replaced by a pair of flexible leaf springs 820 and 822 defining a claw shape surrounding tubular portion 802, such that leaf spring 820 is disposed on one side of tubular portion 802 and leaf spring 822 is disposed on the opposite side thereof. Leaf spring 820 splits into two legs 824 having a slot 825 therebetween, each leg defining a cam surface 826 facing away from tubular portion 802. Leaf spring 822 splits into two legs, each terminating in a proximally facing engagement surface 828, whose functionality is similar to that of surface 516 of valve driver 322 as described hereinbelow. Additionally, at an opposite end from surfaces 828, leaf spring 822 defines two slanted engagement surfaces 830, whose functionality is similar to that of surfaces 526 of valve driver 322 as described hereinbelow.

Reference is now made to FIGS. 29A, 29B, 29C, 29D, and 29E, which are, respectively, an exploded view illustration, a pictorial illustration, a side view planar illustration, and two sectional illustrations of a valve 850 comprising valve housing 618, valve core 620, and valve driver 622 according to an embodiment of the teachings herein, in a first valve position suitable for connection to a medicine vial, the sectional illustrations taken along respective section lines 29D-29D and 29E-29E in FIG. 29C, and to FIGS. 30A, 30B, 30C, 30D, and 30E, which are, respectively, an exploded view illustration, a pictorial illustration, a side view planar illustration, and two sectional illustrations of the valve 850 in a second valve position suitable for fluid communication with needle 616, the sectional illustrations taken along respective section lines 30D-30D and 30E-30E in FIG. 30C.

As mentioned above, valve housing 618 and valve core 620 are, respectively, structurally substantially identical to valve housing 318 and valve core 320 described hereinabove with reference to FIGS. 12A-13D. As such, the structural relationships between valve housing 618 and valve core 620 in the valve positions of FIGS. 29A-29E and 30A-30E are identical to those described hereinabove with reference to FIGS. 15A-15E and 16A-16E, respectively.

Additionally, the valve core connector portion of the valve driver 622 is disposed within bore 772 of the valve core 620, substantially as described hereinabove with reference to FIGS. 15A-16E, such that tubular portion 802 is free to rotate within slot 762, and such that luer connector 794 extend out of valve housing 618. It is appreciated that, as described hereinabove, rotation of the valve driver 622 within slot 762 of the valve housing 618 results in corresponding rotation of valve core 620.

Turning specifically to FIGS. 29A-29E, it is seen that spring leaves 820 and 822 of valve driver 622 extend about part of an exterior surface of body portion 750 of valve housing 618. Specifically, leaf 820 is arranged such that vial adaptor port 754 of valve housing 618 is disposed at the open end of slot 825 of valve driver 622 and lower ends of cam surfaces 826 are adjacent vial adaptor port 754. Additionally, angled surfaces 830 of leaf spring 822 engage angled surfaces 764*a* of protrusions 764 of housing portion 750, thereby to provide mild resistance to turning of the valve driver and valve to the second position (shown in FIGS. 30A-30E).

Turning now to the second valve position shown in FIGS. 30A to 30E, this position is substantially similar to that shown hereinabove with reference to FIGS. 16A-16E, the main differences being related to the position of valve driver 622, as described herein. Specifically, as seen clearly in FIG. 30B, leaf 820 of valve driver 622 has rotated such that vial adaptor port 754 is now disposed at the closed end of slot 825, thus locking valve driver 622 from rotating, in one direction, relative to valve housing 618, and the high point of cam surfaces 826 is adjacent the vial adaptor port 754. Additionally, as seen in FIG. 30C, leaf 822 has rotated correspondingly, such that engagement surfaces 828 thereof now engage right angle surfaces 764*c* of protrusions 764 of the valve housing 618, thus locking valve driver 622 from rotating relative to valve housing 618 in an opposite direction.

Figure 31A:
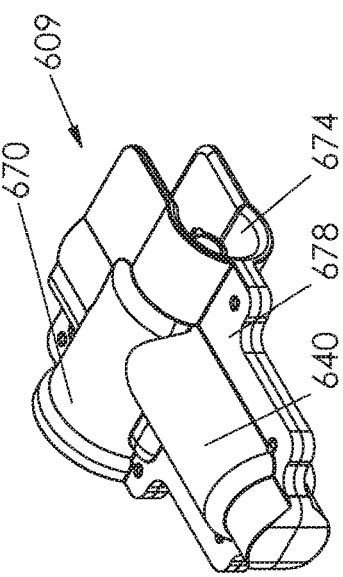
FIGS. 31A, 31B, 31C and 31D are, respectively, a pictorial illustration, a partially cutaway side view planar illustration, and two sectional illustrations of an injection system of FIGS. 22 and 23 according to an embodiment of the teachings herein, in an initial operational position.
Figure 31C:
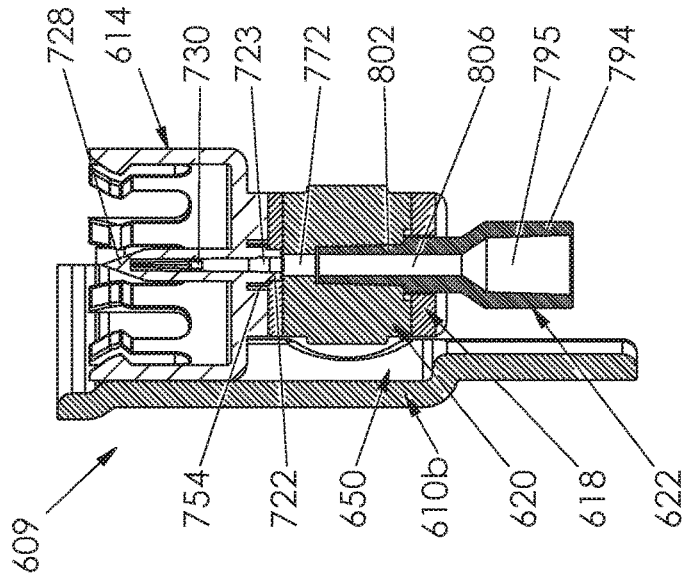
Figure 31B:
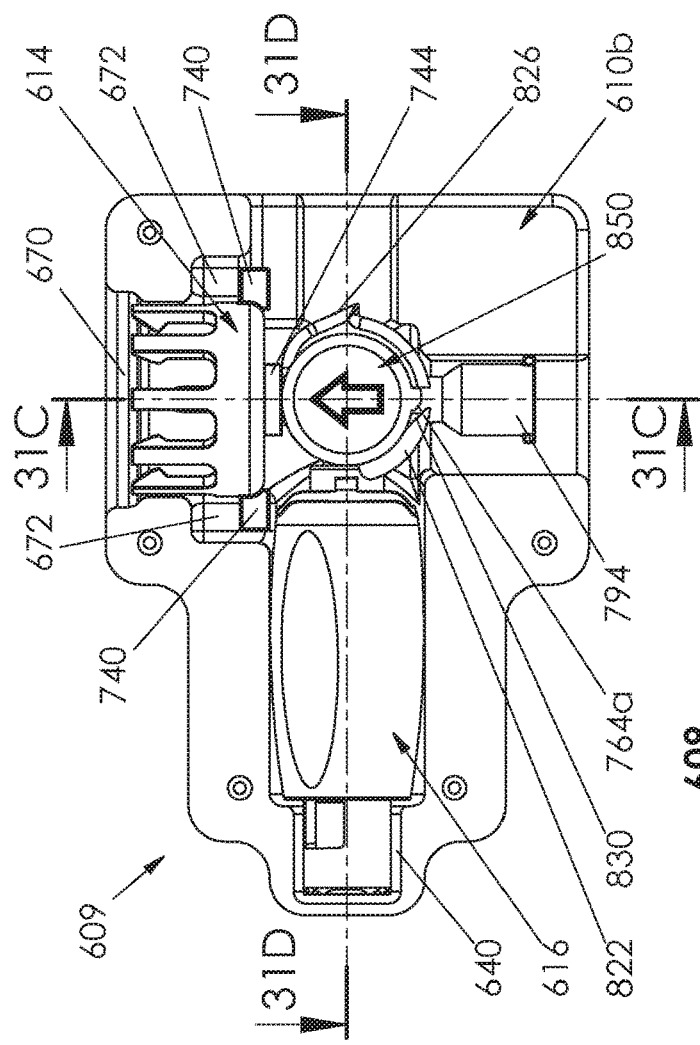

Reference is now made to FIGS. 31A, 31B, 31C and 31D, which are, respectively, a pictorial illustration, a partially cutaway side view planar illustration, and two sectional illustrations of injection system 609 according to an embodiment of the teachings herein, in an initial operational position, the sectional illustrations being taken along section lines and directions 31C-31C and 31D-31D in FIG. 31B.

It is appreciated that FIG. 31B is a planar side view figure of the system 609, having housing portion 610*a* (FIG. 22) removed therefrom, so as to clearly illustrate the interactions between the valve components 618, 620, and 622, the vial adaptor 614, the needle 616, and the housing 610 in the initial operational position of the injection system 609.

It is further appreciated that many of the structural relationships illustrated in FIGS. 31A-31D are identical to those described in corresponding FIGS. 17A-17F, and as such will be described here briefly in reference to the description of FIGS. 17A-17E.

As seen clearly in FIG. 31B, valve 850 as described hereinabove with reference to FIGS. 29A to 29E is disposed within compartment 650 of housing 610. Needle 616 is disposed within needle compartment 640 of housing 610. Vial adaptor 614 is disposed in vial adaptor port 670 of housing 610, such that connector 722 of the vial adaptor engages vial adaptor port 754 of valve housing 618. Additionally, pins 740 of vial adaptor 614 are disposed within guides 672 of housing portion 610. Additionally, lower ends of cam surfaces 826 of leaf spring 820 are disposed adjacent to protrusions 744 of vial adaptor 614, such that the protrusions 744 are seated on cam surfaces 826 at their lowest ends.

As mentioned above with respect to FIGS. 29A-29E, and as seen in FIG. 31B, in the first position of valve 850, angled surfaces 830 of the leaf spring 822 of valve driver 622 lie adjacent angled surfaces 764a of protrusions 764 of valve portion 618, thereby to provide mild resistance to turning of the valve driver and consequently the valve.

Turning specifically to FIG. 31C, it is seen that luer connector 794 of valve driver 622 is in fluid flow communication with spike 728 of vial adaptor 614 via fluid flow path 806 of tubular portion 802 of valve driver 622; bore 772 of valve core 620; and fluid flow path 723 of luer connector 722 of vial adaptor 614, which is disposed within opening 756 of vial adaptor port 754 of valve housing 618.

Figure 31D:
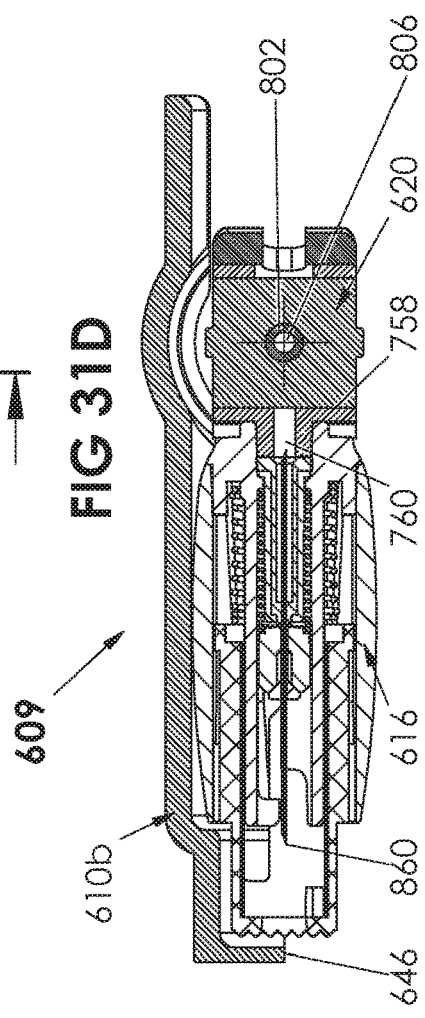

Turning to FIG. 31D, it is seen that a connector of needle 616 engages needle port 758 of valve housing 618 and forms a fluid flow path between a tip 860 of needle 616 and flow path 760 of port 758. However, as seen, no flow path exists between bore 772 of valve core 620 or flow path 806 of valve driver 622 and needle 616.

Reference is now made to FIGS. 32A and 32B, which are, respectively, a side view planar illustration and a sectional illustration of the injection system 609 in a vial connection operational position, the sectional illustration taken along section lines 32B-32B in FIG. 32A.

Similarly to that shown with reference to FIGS. 18A and 18B, a user has inserted a medicine vial 862, similar to vial 562 described hereinabove, into vial adaptor 614 by pushing the vial into the vial adaptor as known in the art. Following connection of the vial adaptor 614 to the vial 862, spike 728 of vial adaptor 614 has punctured seal 866 of the vial, such that the medicament included within body portion 870 of the vial is in fluid flow communication with luer connector 794 of valve driver 622.

Additionally, segments 734 of the circumferential wall of vial adaptor 614 are disposed about head portion 864 of vial 862, such that protrusions 738 of the segments 734 engage head portion of the vial.

Aside from connection of vial 862 to vial adaptor 614, no other changes occur to any of the components of injection system 609 relative to the position illustrated in FIGS. 31A-31D.

Reference is now made to FIGS. 33A and 33B, which are, respectively, a top view planar illustration and a sectional illustration of injection system 609 a syringe connection and medicine transfer and reconstitution operational position, the sectional illustration taken along section lines 33B-33B in FIG. 33A.

Similarly to that shown with reference to FIGS. 19A and 19B, the user connects a suitably sized syringe 880 to female luer connector 794 of valve driver 622, such that the interior of syringe 880 is in fluid flow communication with the medicament or diluent disposed in vial 862 via flow paths 795, 806, 723, and 730 and bore 772, substantially as described hereinabove with reference to FIGS. 32A and 32B. Once the syringe 880 is connected to valve driver 622, the user may pull a plunger 884 of syringe 880 distally to draw the medicament from vial 862, reconstitute the medicament, or otherwise prepare the medicament.

Aside from connection of syringe 880 to valve driver 622, no other changes occur to any of the components of injection system 609 relative to the positions illustrated in FIGS. 32A-32B.

Reference is now made to FIGS. 34A, 34B, and 34C which are, respectively, a partially cut away side view planar illustration, and two sectional illustrations of injection system 609 in a syringe rotation and needle fluid communication operational position, wherein sectional illustrations 34B and 34C are taken along respective section lines 34B-34B and 34C-34C in FIG. 34A.

It is appreciated that FIG. 34A is a planar side view figure of the system 609, having housing portion 610a (FIG. 22) removed therefrom, so as to clearly illustrate the interactions between the valve components 618, 620, and 622, the vial adaptor 614, the needle 616, and the housing 610.

As seen, the user has rotated syringe 880 by an angle of 90 degrees, such that the syringe is now aligned with needle compartment 640 of the housing 610. The rotation is made possible by the 90 degree breadth of syringe rotation port 674 of housing 610.

As seen in FIG. 34A, following rotation of syringe 880 to be aligned with needle compartment 640, valve 850 has rotated from the position shown in FIGS. 29A-29E to the position shown in FIGS. 30A-30E under the driving force of valve driver 622, such that bore 772 of valve core 620 is now aligned with needle port 758 of valve housing 618. As such, as seen with particular clarity in FIG. 34C, syringe 880 is now in fluid flow communication with tip 860 of needle 616 via flow path 795 of luer connector 794 and flow path 806 of tubular portion 802 of valve driver 622, bore 772 of valve core 620, and flow path 760 of needle port 758 of valve housing 618. Consequently, no flow path exits between bore 772 of valve core 620 and vial adaptor 614, as seen in FIG. 34B.

As seen in FIG. 34A, rotation of syringe 880 and corresponding rotation of valve driver 622 results in cam surfaces 826 of spring leaf 820 to rotate beneath protrusions 744 of vial adaptor 614, such that the vial adaptor 614 is pushed away from valve 850 along vial adaptor guides 672 in housing 610. As a result, the vial adaptor is disconnected from vial adaptor port 754 of valve housing 618. Additionally, engagement surfaces 828 of spring leaf 822 irremovably engage surfaces 764c protrusions 764 of valve housing 618, such that the valve driver 622 cannot be rotated relative to the valve housing 618 as best seen in FIG. 30D. However, it will be appreciated that in some embodiments the vial adaptor is permanently fixed to vial adaptor port 754, and does not disconnect therefrom.

Reference is now made to FIGS. 35A and 35B, which are, respectively, a side view planar illustration of needle 616, valve 850, and syringe 880 following removal thereof from housing 610 of injection system 609 and ready for injection, and an enlarged view of a portion of FIG. 35A.

As seen, proximal surfaces 828 of leaf spring 822 lock against surfaces 764c of protrusions 764 of valve housing 618, such that the valve driver, and consequently the valve core 620 and syringe 880, cannot be rotated relative to the valve housing in one direction while in the other direction it cannot be rotated as described above in reference to FIGS. 30A to 30E.

In the position of FIGS. 35A and 35B, the user would bring the proximal portion 890 of needle 616 close to the injection site, and would proceed to inject the contents of the syringe into the site as known in the art.

It is appreciated that in some embodiments, the vial adaptor (such as vial adaptor 314 of FIGS. 1A-21B or vial adaptor 614 of FIGS. 22-35B) need not fully disengage from the valve, as described hereinabove with reference to FIGS. 20A-20I and 34A-34C. In such embodiments, the vial adaptor may remain attached to the valve even following rotation of the valve to the needle fluid communication position, and may even be permanently attached to, or integrally formed with, the valve. In such embodiments, the housing (such as housing 310 and/or 610 described hereinabove) is adapted to enable extraction of the vial adaptor together with the valve and needle when preparing for injection (as described with reference to FIGS. 21A-21B and 35A-35B. Alternately, the housing may be adapted so that injection could take place without removing the valve and needle from the housing (such as by allowing the skin-engaging end of the needle to be exposed even when the needle is in the housing). As a further alternative, the housing may be omitted altogether.

Figure 36:
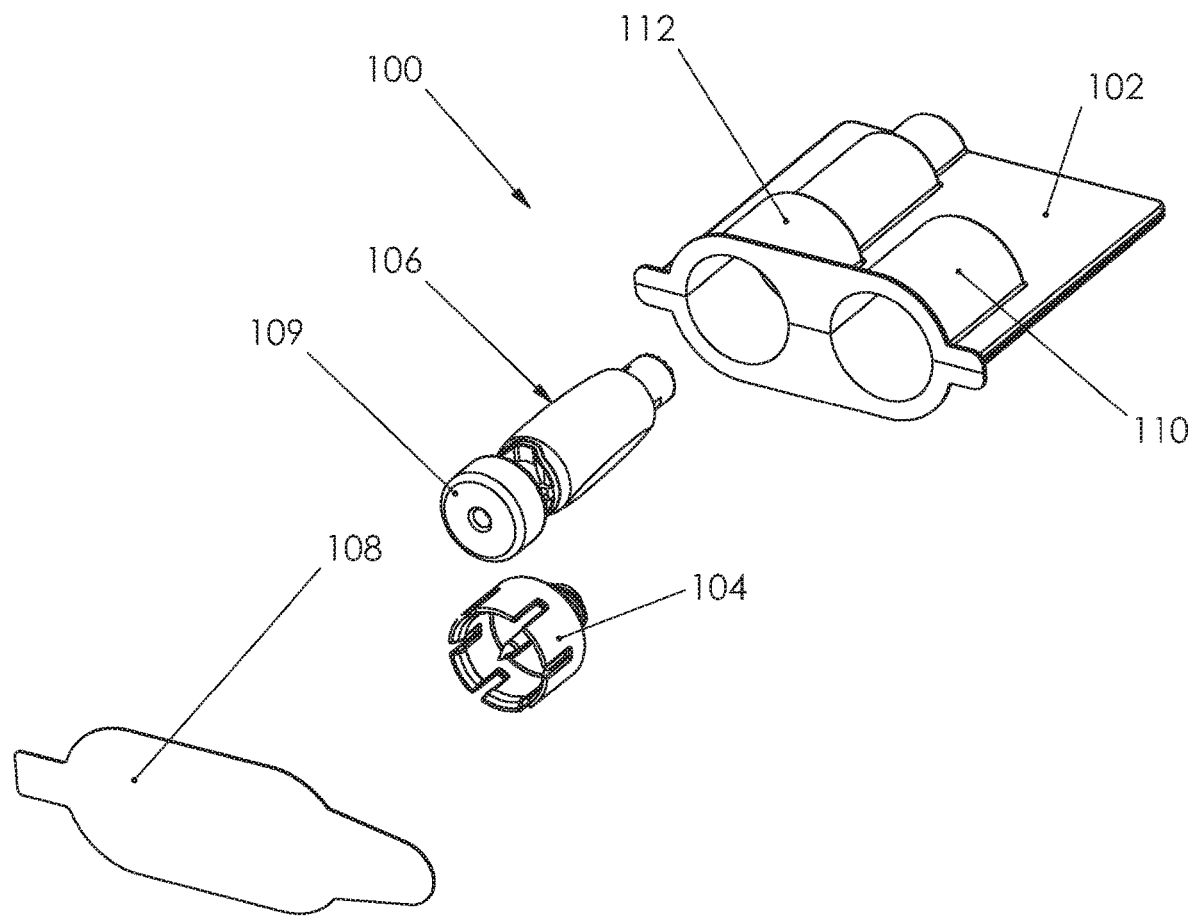
FIG. 36 is an exploded view illustration of a system for interfacing between a syringe, a drug vial, and a needle, according to an embodiment of the teachings herein.

Reference is now made to FIG. 36 which is an exploded view illustration of a system for interfacing between a syringe, a drug vial, and a needle, according to an embodiment of the teachings herein, and to FIGS. 37A, 37B, 37C, and 37D, which are simplified pictorial illustrations of the system of FIG. 36 as assembled according to four embodiments of the teachings herein.

As seen in FIG. 36, a system 100 according to the teachings herein includes a casing 102, a vial adaptor 104, a needle 106, and a seal 108.

The vial adaptor 104 may be any suitable vial adaptor, for example as described hereinbelow with reference to FIGS. 38A-38D and 39A-39C, or a commercially available vial adaptor such as a vial adapter commercially available from West Pharmaceutical Services, Inc., of 530 Herman O. West Drive, Exton, Pa. 19341, USA.

The needle 106 may be any suitable needle, including a standard hypodermic needle such as a BD Regular Bevel Needle or a safety needle such as a BD SafetyGlide Hypodermic Needle, both commercially available from Becton Dickinson and Company of 1 Becton Drive, Franklin Lakes, N.J. 07417-1880. In some embodiments, the needle 106 is an automatic injection needle, for example as disclosed in U.S. Pat. No. 7,901,382, filed on Sep. 15, 2004 and entitled "AUTOMATIC NEEDLE DEVICE" and in U.S. patent application Ser. No. 14/505,690, filed on Oct. 3, 2014 and entitled "AUTOMATIC NEEDLE APPARATUS" which are fully incorporated by reference herein. It is appreciated that the needle 106 is fitted with a needle adaptor 109 as described hereinbelow with reference to FIGS. 40A-40C and 41A-41C.

The seal 108 may be a single seal or may comprise multiple seals as explained hereinbelow, and is operative to ensure the sterility of the vial adaptor 104 and needle 106 while disposed within casing 102.

In FIGS. 37A, 37B, 37C, and 37D it is seen that casing 102 includes a vial adaptor compartment 110 accommodating the vial adaptor 104 and a needle compartment 112 accommodating the needle 106. The compartments 110 and 112 are sealed by one or more seals 108.

Figure 37A:
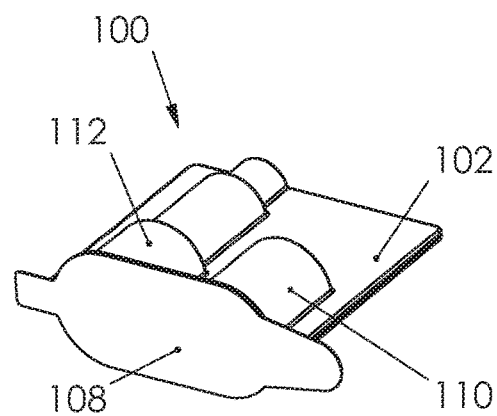
FIGS. 37A, 37B, 37C, and 37D are simplified pictorial illustrations of the system of FIG. 1 as assembled according to four embodiments of the teachings herein.
Figure 37B:
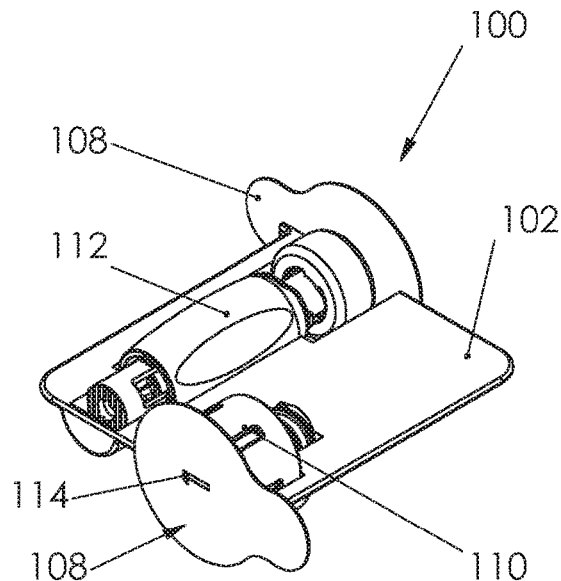

In the embodiments of FIGS. 37A and 37B, the compartments 110 and 112 lie generally alongside one another, such that the compartments 110 and 112 do not share a single longitudinal axis. Additionally, in these embodiments, the compartments 110 and 112 are typically permanently sealed on one side thereof by casing 102, and include an opening on the other side thereof, which opening is sealed by the one or more seals 108.

Turning specifically to FIG. 37A, it is seen that in some embodiments, openings of compartments 110 and 112 are aligned and point in the same direction, and a single seal 108 may be used to seal both compartments 110 and 112. In other embodiments, the openings of the vial adaptor compartment 110 and the needle compartment 112 do not point in the same direction, and may each be sealed by a separate seal 108, as shown in FIG. 37B.

Figure 37C:
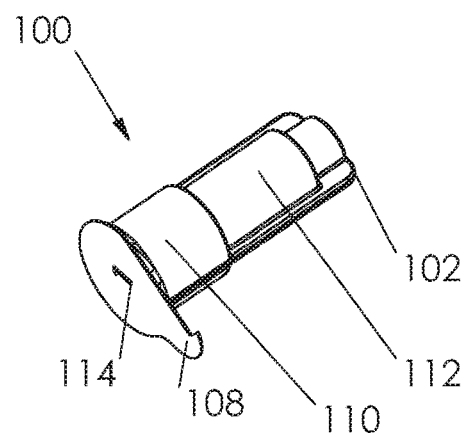
Figure 37D:
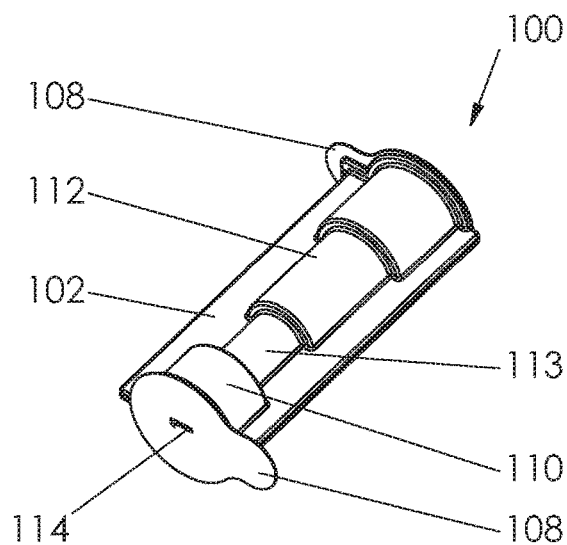

In the embodiments of FIGS. 37C and 37D, the compartments 110 and 112 are aligned with one another, along a single longitudinal axis, such that casing 102 may, in some embodiments, resemble a tube housing the vial adaptor 104 and the needle 106. Additionally, in these embodiments, the compartments 110 and 112 are typically not separated from one another by any material, and are defined by the internal circumferences of casing 102 and by shoulders defined thereby. For example, as seen in FIG. 37D, casing 102 includes a hollow section 113 having a narrower inner circumference than compartments 110 and 112, such that the shoulders defined at the edges between compartments 110 and 112 prevents vertical motion of the vial adaptor 104 and needle 106 within casing 102.

Turning specifically to FIG. 37C, it is seen that in some embodiments, compartments 110 and 112 are in-line with one another and together form an "extended" compartment, having a single opening sealed by seal 108. In use of such embodiments, the user removes seal 108 to access the vial adaptor 104, and once the vial adaptor has been removed from casing 102 the user may access needle 106, substantially as described hereinbelow. In other embodiments, compartments 110 and 112 are longitudinally aligned but have openings pointing in opposite directions, such that each of the compartments 110 and 112 may be accessed separately, by removing a dedicated seal 108 of that compartment, as shown in FIG. 37D.

It is appreciated that the seal 108, be it a single seal or multiple seals, may include a graphical indication of the component of the system included within the compartment or of the order in which the seal(s) need be opened, as seen by numbers indicated by reference numeral 114 in FIGS. 37B, 37C, and 37D. Such graphical indications or labeling may also be included on the casing 102.

Figure 39A:
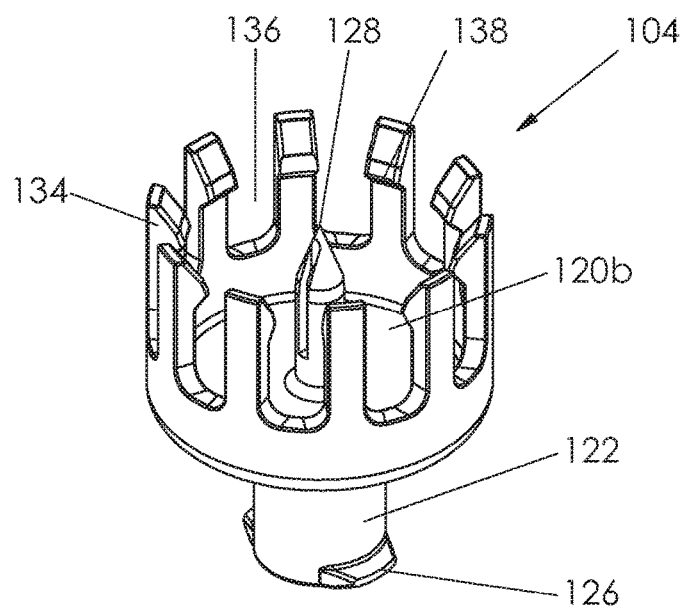
FIGS. 39A, 39B, and 39C are, respectively, a pictorial illustration, a side view planar illustration, and a sectional illustration of a vial adaptor forming part of the system of FIGS. 36-37D according to another embodiment of the teachings herein.
Figure 39B:
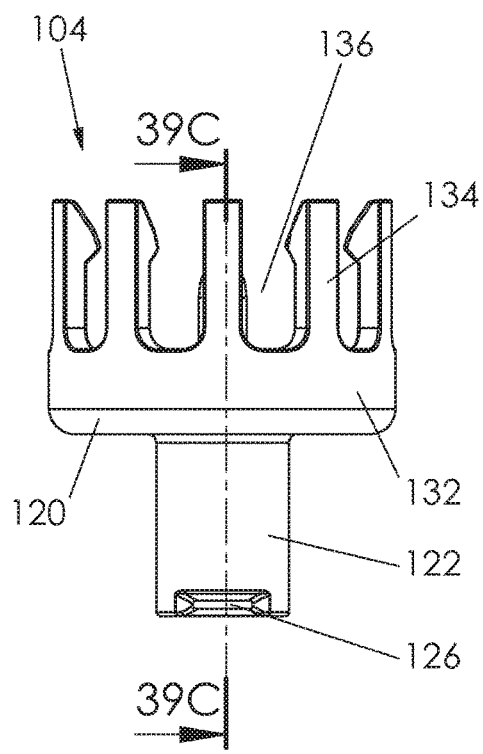
Figure 39C:
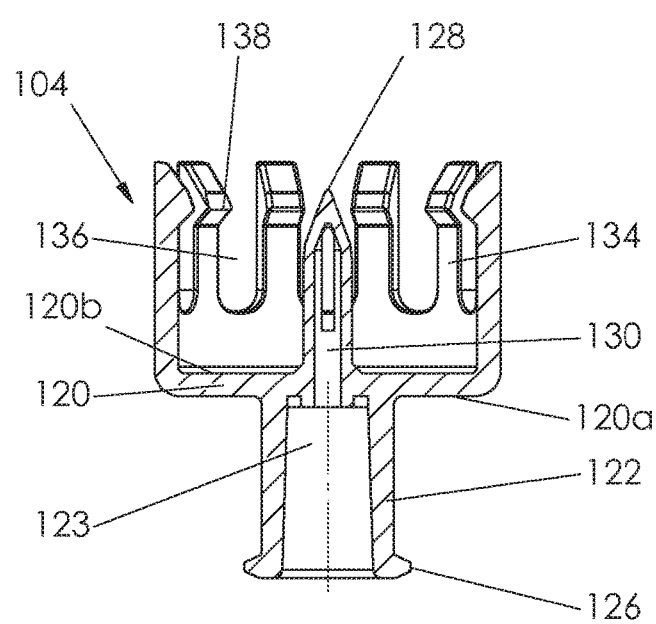

References is now made to FIGS. 38A, 38B, 38C, and 38D which are, respectively, top and bottom view pictorial illustrations, a side view planar illustration, and a sectional illustration of a vial adaptor 104 forming part of the system 100 according to an embodiment of the teachings herein, the sectional illustration taken along section lines 38D-38D in FIG. 38C, and to FIGS. 39A, 39B, and 39C, which are, respectively, a pictorial illustration, a side view planar illustration, and a sectional illustration of a vial adaptor 104 forming part of the system 100 according to another embodiment of the teachings herein, the sectional illustration taken along section lines 39C-39C in FIG. 39B.

As seen in FIGS. 38A to 39C, vial adaptor 104 includes a generally circular base 120 having first and second base surfaces 120a and 120b opposing one another. Extending longitudinally outwardly, generally from the center of first base surface 120a, is a hollow tubular protrusion 122 having a fluid flow path 123 therethrough and defining a standard female luer connector. In the embodiment of FIGS. 38A-38D, the male luer connector 122 comprises a threaded protrusion 124, whereas in the embodiment of FIGS. 39A-39C the standard female luer connector only includes flanges 126.

Extending longitudinally outwardly, generally from the center of second base surface 120b, is a hollow spike 128 defining a fluid path 130 therethrough. The fluid path 130 of spike 128 is in fluid flow communication with fluid path 123 of luer connector 122. Extending longitudinally outwardly from a circumference of base 120 is a generally circumferential side wall 132 which at a suitable height thereof is split into a plurality of side wall segments 134 separated by gaps 136. Each of wall segments 134 terminates in a radially inwardly extending protrusion 138, which is adapted, in use, to engage a neck portion of a drug vial. In some embodiments, protrusions 138 are configured for irremovable snap-fit engagement with the drug vial, and in other embodiments the protrusions 138 are configured for releasable engagement with the neck of the drug vial. Furthermore, other embodiments may not include protrusions 138 at all, and/or have side wall 132 extend to the full height of the vial adaptor, without splitting into segments 134 and without defining gaps 136.

It is appreciated that the width of, or the number of degrees of the circumference covered by, each segment 134, as well as the width of, or number of degrees of the circumference covered by, each gap 136, may vary depending on the specific embodiment, as clearly visible from comparison of the illustrated embodiment of FIGS. 38A-38D with that of FIGS. 39A-39C.

It will be appreciated by people of skill in the art, that the height of side wall 132, the width of segments 134, and the width of gaps 136, determine how difficult it would be for a user to remove a vial from the vial adaptor 104.

Figure 40A:
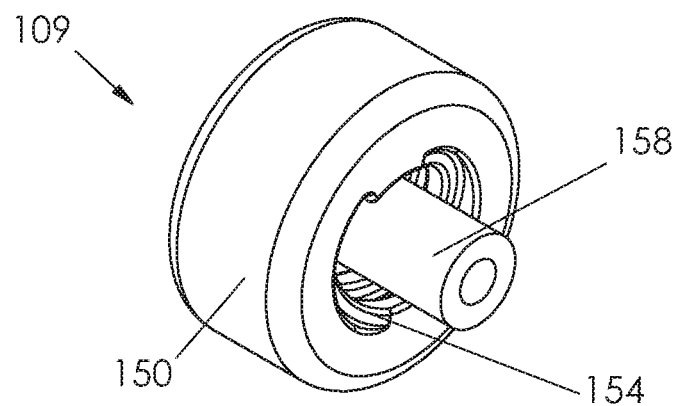
FIGS. 40A, 40B, and 40C are, respectively, a pictorial illustration, a side view planar illustration, and a sectional illustration of a needle adaptor forming part of the system of FIG. 36 according to an embodiment of the teachings herein.
Figure 40B:
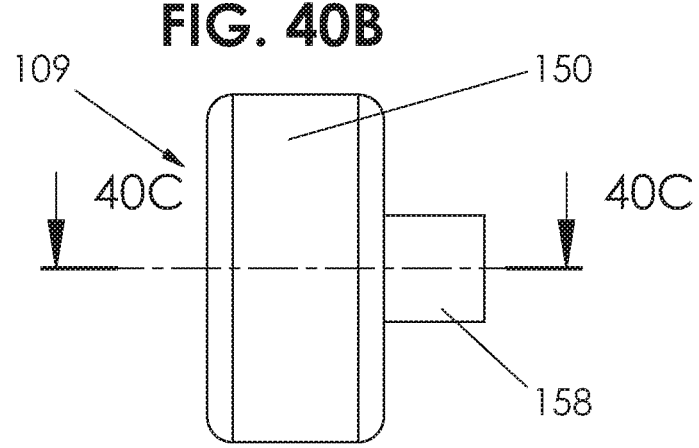
Figure 40C:
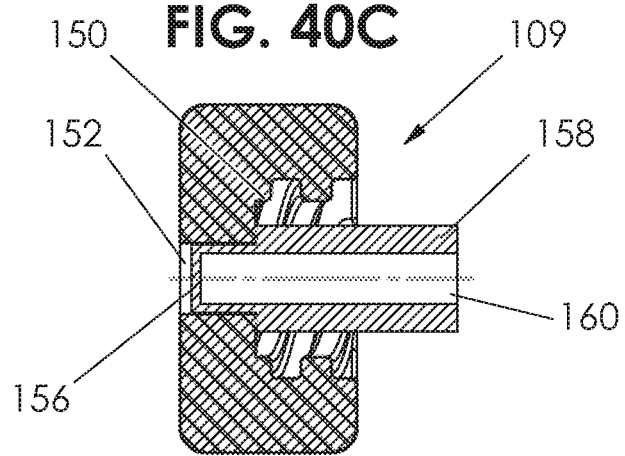

Reference is now made to FIGS. 40A, 40B, and 40C, which are, respectively, a pictorial illustration, a side view planar illustration, and a sectional illustration of a needle adaptor 109 forming part of the system 100 according to an embodiment of the teachings herein, the sectional illustration taken along section lines 40C-40C in FIG. 40B, and to FIGS. 41A, 41B, and 41C, which are, respectively, a pictorial illustration, a side view planar illustration, and a sectional illustration of a needle adaptor 109 forming part of the system 100 according to another embodiment of the teachings herein, the sectional illustration taken along section lines 41C-41C in FIG. 41B.

As seen in FIGS. 40A-41C, needle adaptor 109 includes a generally circular adaptor portion 150 having a bore 152 defined in the center thereof and defining a thread 154 therein configured for connection to a female luer connector. In some embodiments, an end of bore 152 may include an elastomeric seal 156. A tubular flexible elastomeric seal 158 is disposed centrally within adaptor base portion 150, such that a bore 160 thereof is in fluid flow communication with bore 152 of base portion 150. Seal 158 extends longitudinally in the center of the thread 154, and longitudinally outwardly therefrom. In some embodiments, the elastomeric seal 156 is integrally formed with seal 158, as seen with particular clarity in FIG. 40C.

Turning specifically to the embodiment of FIGS. 40A-40C, it is seen that tubular seal 158 includes a portion disposed within bore 152, which portion may have a lesser material thickness than the rest of seal 158. In other embodiments, such as that shown in FIGS. 41A-41C, adaptor base portion 150 has disposed therein a generally circumferential recess 170, and seal 158 includes a generally circumferential flange 172 adapted to be seated within recess 170. Additionally, in the embodiment of FIGS. 41A-41C, sealing is achieved by seal 158, without requiring a septum (such as septum 156 of FIGS. 40A-40C).

In some embodiments, seal 158 and adaptor base portion 150 are integrally formed, for example by two-component injection molding. In other embodiments, seal 158 and adaptor base portion 150 may be molded one over the other. In further embodiments, seal 158 and adaptor base portion 150 may be separately manufactured, and then assembled to form needle adaptor 109.

As explained hereinbelow, it is a particular feature of the disclosure herein that adaptor base portion 150 is adapted and sized to correspond to the circumference of a standard medicine vial, and to be connectable to a vial adaptor, such as vial adaptor 104 described hereinabove. Similarly, it is a particular feature of the disclosure herein that seal 158 is adapted and sized to correspond and to fit into a typical female luer connector, as often found in hypodermic needles, both manual and automatic, when the female luer connector is connected to thread 154 of needle adaptor 109.

Figure 42A:
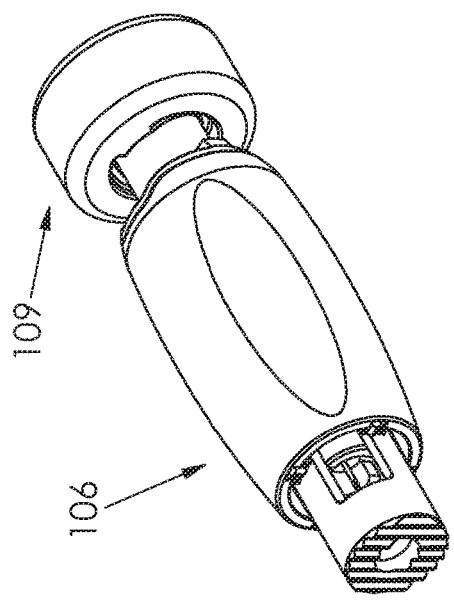
FIGS. 42A, 42B, and 42C are, respectively, a pictorial illustration, a front view planar illustration, and a sectional illustration of the needle adaptor of FIGS. 40A-40C mounted onto a needle.
Figure 42B:
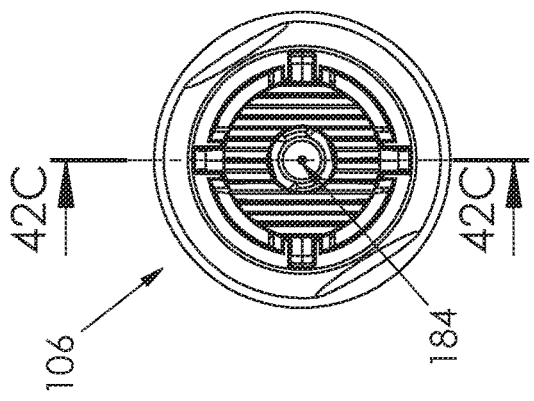
Figure 42C:
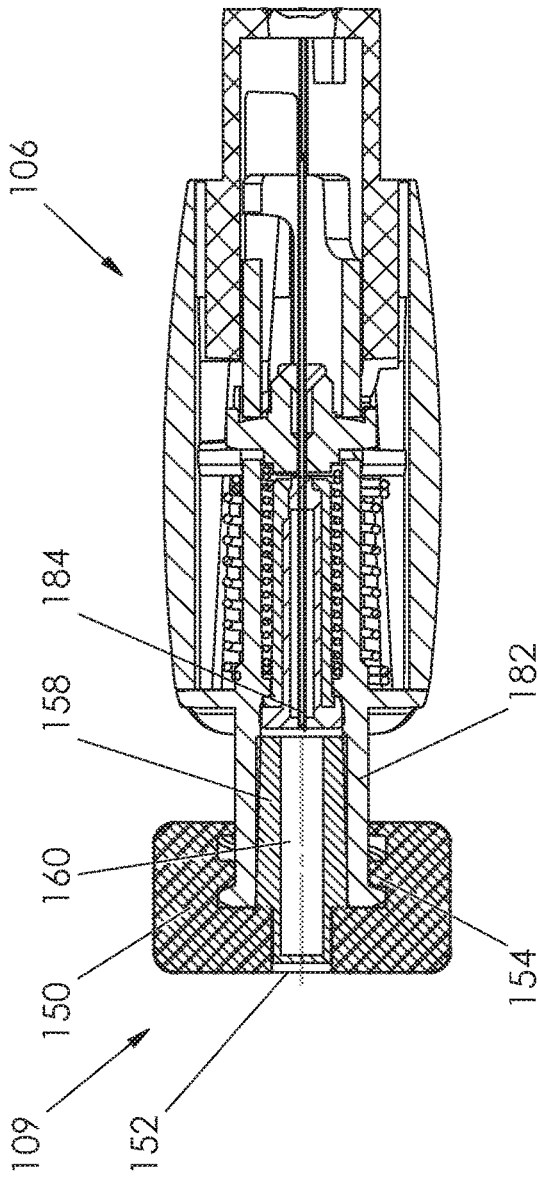

Reference is now made to FIGS. 42A, 42B, and 42C, which are, respectively, a pictorial illustration, a front view planar illustration, and a sectional illustration of the needle adaptor 109 of FIGS. 40A-40C mounted onto a needle 106, the sectional illustration taken along section lines 42C-42C in FIG. 42B.

As seen, needle adaptor 109 is mounted onto the needle 106 of FIG. 36, which, in the illustrated embodiment, is an automatic injection needle. As mentioned above, the needle 106 may be any suitable needle, including a standard hypodermic needle, a safety needle, and/or an automatic needle. In some embodiments, needle adaptor 109 is irremovable from needle 106.

As seen with particular clarity in FIG. 42C, the thread 154 of needle adaptor 109 receives a female luer connector 182 of needle 106 for engagement therebetween, such that seal 158 of needle adaptor 109 is disposed within the bore of the female luer connector 182 and engages an inner wall thereof, and bores 152 and 160 of the needle adaptor 109 are in fluid flow communication with a hypodermic needle 184 of needle 106.

Reference is now made to FIGS. 43A, 43B, and 43C, which are side view planar illustrations of three steps of connecting vial adaptor 104 to a vial using system 100 and removal of the vial adaptor 104 from casing 102, and to FIG. 43D which is a sectional illustration of the connection between the vial adaptor 104 the vial following completion of the step of FIG. 43C, taken along section lines 43D-43D in FIG. 43C.

As seen in FIG. 43A, at an initial stage of use, a medicine vial 200 is aligned with the vial adaptor compartment 110 of system 100, following opening at least a portion of the seal 108 thereof covering the vial adaptor compartment 110. The medicine vial may be any suitable, typically sized, medical vial, and includes a head portion 202 sealed by a seal 203 (best seen in FIG. 43D), a neck portion 204, and a body portion 206.

In FIG. 43B, the user pushes vial 200 into the vial adaptor compartment 110, in the direction indicated by reference numeral 210, thereby connecting the vial adaptor in compartment 110 to the vial 200, as explained hereinbelow. At the next step, shown in FIG. 43C, the user removes the vial 200 and the vial adaptor 104 connected thereto from casing 102, by pulling them in the direction indicated by reference numeral 212. As seen with particular clarity in FIG. 43D, following connection of the vial adaptor 104 to the vial 200, spike 128 of vial adaptor 104 has punctured seal 203 of vial 200, such that the bore 123 of the female luer connector 122 of the vial adaptor and bore 130 of the spike are in fluid flow communication with the medicament included within body portion 206 of the vial. Additionally, segments 134 of the circumferential wall of vial adaptor 104 are disposed about head portion 202 of vial 200, such that protrusions 138 of the segments 134 removably engage head portion 202 of the vial. At this stage, female luer connector 122 of the vial adaptor 104 extends longitudinally away from vial 200, and is free to connect to a suitable male luer connector.

Reference is now made to FIGS. 44A and 44B, which are, respectively, a side view planar illustration and a sectional illustration of a step of connecting a syringe, optional mixing/reconstitution, and drawing fluid from the drug vial 200 and adaptor 104 of FIGS. 43C-43D into a syringe, the sectional illustration taken along section lines 44B-44B in FIG. 44A.

As seen, the user connects a suitably sized syringe 220 to female luer connector 122 of vial adaptor 104 in a direction indicated by reference numeral 226, such that the interior of syringe 220 is in fluid flow communication with the medicament or diluent disposed in vial 200, via bores 130 and 123 of the vial adaptor. In some embodiments, syringe 220 includes a male luer connector 222 which is connected to the female luer connector 122 of vial adaptor 104. Once the syringe 220 is connected to vial adaptor 104, the user may pull a plunger 224 of syringe 220 distally to draw the medicament from vial 200.

It is appreciated that in some embodiments, drawing the medicament from the vial 200 may include additional steps, such as, prior to connecting the syringe 220 to vial adaptor 104 drawing water or another liquid 220 into the syringe, following connection of the syringe and the vial adaptor injecting the liquid from the syringe into the vial 200, mixing the content of the vial 200 with the injecting liquid to form a solution or suspension, and drawing the formed solution or suspension back into the syringe as a medicament, and/or any other steps required in other drug preparation protocols known in the art.

Figure 45A:
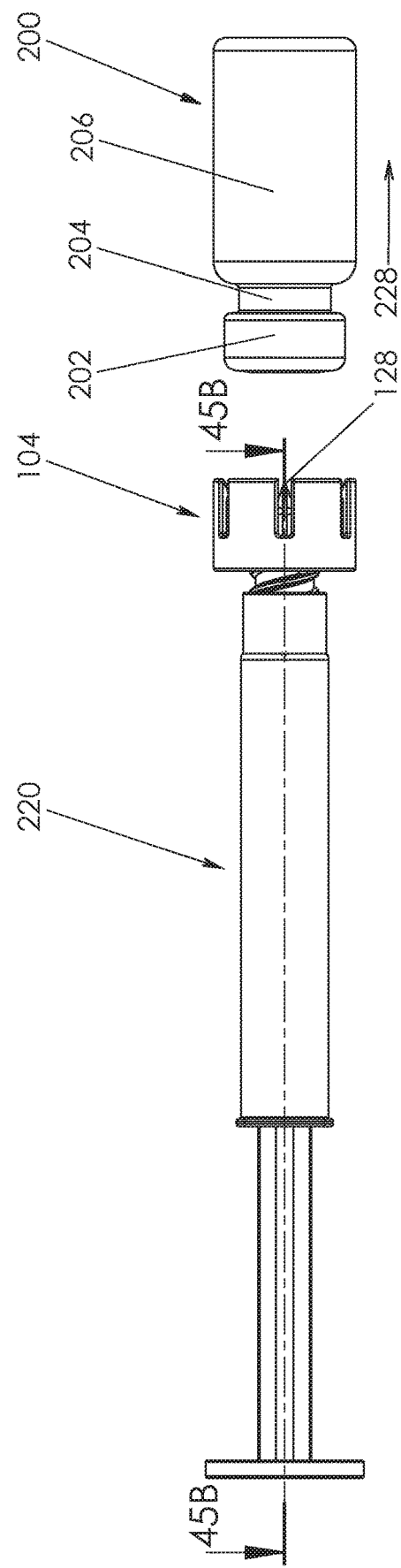
FIGS. 45A and 45B are, respectively, a side view planar illustration and a sectional illustration of the syringe and vial adaptor following removal of the drug vial therefrom.
Figure 45B:
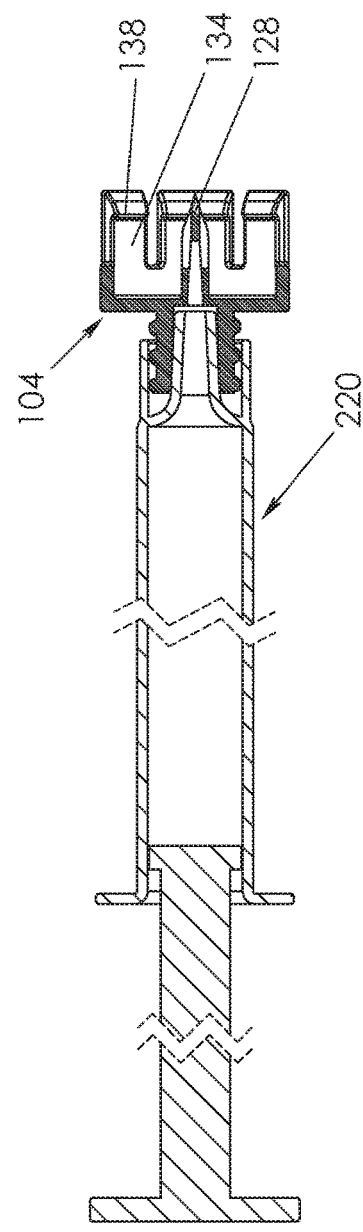

Reference is now made to FIGS. 45A and 45B, which are, respectively, a side view planar illustration and a sectional illustration of the syringe 220 and vial adaptor 104 following removal of the drug vial 200 therefrom, the sectional illustration taken along section lines 45B-45B in FIG. 45A.

As seen, following drawing of the liquid medicament from the vial 200 into the syringe 220, the user disconnects vial 200 from vial adaptor 104 by pulling the vial away from the vial adaptor in a direction indicated by reference numeral 228. In some embodiments, disconnection between the vial adaptor and the vial is achieved by slight radially outward bending of segments 134 of the vial adaptor, driven by a suitably angled surface of protrusions 138 moving along a surface of head portion 202 of the vial until the protrusions 138 no longer engage the head portion 202 and the vial can be removed from the vial adaptor 104. Separation of the vial adaptor 104 from vial 200 also causes spike 128 to be removed from the seal of the vial.

It is appreciated that following removal of vial 200 from vial adaptor 104, the user may connect one or more additional vials to the vial adaptor 104, for mixing a medicament contained therein with the liquid already in syringe 220, as commonly known in the art of pharmaceuticals. Each such connection of a vial to vial adaptor 104 is achieved by pushing the vial into the vial adaptor substantially as described hereinabove with reference to FIG. 43B, while the vial adaptor 104 is not situated in a casing, such as casing 102 (FIG. 36). Each removal of a vial from the vial adaptor 104 is achieved by pulling the vial out of the vial adaptor substantially as described herein. Reference is now made to FIGS. 46A and 46B, which are side view planar illustrations of a step of connecting the syringe 220 and vial adaptor 104 of FIGS. 45A-45B to needle adaptor 109 and needle 106 of system 100, to FIG. 46C which is a sectional illustration of the connection between the vial adaptor 104, needle adaptor 109, and needle 106 during the step of FIG. 46B, the sectional illustration taken along section lines 46C-46C in FIG. 46B, and to FIG. 46D, which is a side view planar illustration of the connected syringe 220, vial adaptor 104, needle adaptor 109, and needle 106, ready for injection.

As seen in FIG. 46A, the syringe 220, still connected to vial adaptor 104, is aligned with the needle compartment 112 of casing 102 of system 100 as shown in FIG. 37A, following opening at least a portion of the seal 108 thereof covering the needle compartment 112. The needle 106 disposed within compartment 112 is pre-connected to a needle adaptor 109, as described hereinabove with reference to FIGS. 42A-42C.

In FIG. 46B, the user pushes syringe 220 and vial adaptor 104 into the needle compartment 112, in the direction indicated by reference numeral 230, thereby connecting the vial adaptor 104 mounted onto syringe 220 to the needle adaptor 109, as explained hereinbelow. FIG. 46C shows a sectional illustration of the syringe 220 and vial adaptor 104, connected to the needle 106 and needle adaptor 109 while the latter are disposed within compartment 112 of casing 102.

As seen with particular clarity in FIG. 46C, following connection of the vial adaptor 104 to the needle adaptor 109, spike 128 of vial adaptor 104 has punctured the elastomeric seal 156 of needle adaptor 109, or otherwise sealingly entered needle adaptor 109, and extends into bore 160 of seal 158 of the needle adaptor 109, which is disposed within female luer connector 182 of needle 106. As such, there is a fluid flow communication path between syringe 220 and hypodermic needle 184 of needle 106 via respective bores 123 and 130 of female luer connector 122 and spike 128 of vial adaptor 104 and bores 152 and 160 of needle adaptor 109. Additionally, segments 134 of the circumferential wall of vial adaptor 104 are disposed about body portion 150 of needle adaptor 109, such that protrusions 138 of the segments 134 engage a bottom surface of the body portion 150. In some embodiments, segments 134 engage needle adaptor 109 by snap-fit engagement, such that the vial adaptor 104 and needle adaptor 109 cannot be readily disconnected. It is appreciated that in such embodiments, segments 134 are designed not to irremovably snap fit onto a head portion of a drug vial, such as head portion 202 of vial 200 (FIG. 43D). It is appreciated that vial adaptor 104 and or needle adaptor 109 may include additional or other attachment mechanisms, for example enabling snap fit engagement between the vial adaptor 104 and the needle adaptor 109, for example as described hereinbelow with reference to FIGS. 47A-47D.

At the final step, shown in FIG. 46D, the user removes the needle 106 and needle adaptor 109, together with vial adaptor 104 and syringe 220 connected thereto, from casing 102, by pulling them in the direction indicated by reference numeral 232. The needle and syringe are now ready for use, and the medicament may be injected into a suitable injection site.

Reference is now made to FIG. 47A, which is a pictorial illustration of a vial adaptor 254 forming part of system 100 according to an embodiment of the teachings herein, to FIG. 47B, which is a pictorial illustration of a needle adaptor 259 forming part of system 100 according to an embodiment of the teachings herein, and constructed to snap fit with the vial adaptor 254 of FIG. 47A, to FIG. 47C, which is a partially cut-away side view planar illustration of a step of connecting a syringe 220 having attached thereto the vial adaptor 254 to a needle 106 having attached thereto the needle adaptor 259, and to FIG. 47D, which is a pictorial illustration of the vial adaptor 254 when connected to the needle adaptor 259, according to an embodiment of the teachings herein. For the sake of simplicity, the syringe 220 and needle 106 are not shown in FIG. 47D.

As seen in FIG. 47A, the vial adaptor 254 is substantially the same as the vial adaptors 104 described hereinabove with reference to FIGS. 38A-39C, with like numbers representing like elements. As seen clearly in FIG. 47A, surrounding luer connector 122 extending out of base 120, are two generally semicircular slots 256 cut out of base 120. A circumferential frame 258, forming part of base 120, surrounds slots 256 along the circumference of base 120. Other aspects of vial adaptor 254, such as wall portion 132, segments 134, gaps 136, protrusions 138, and spike 128, are substantially as described hereinabove.

Turning to FIG. 47B, the needle adaptor 259 is substantially the same as the needle adaptors 109 described hereinabove with reference to FIGS. 40A-41C, with like numbers representing like elements. As seen, extending outwardly of adaptor portion 150 and away from seal 158, are a pair of protrusions 260. Protrusions 260 are typically arranged adjacent the circumference of adaptor portion 150, and are offset from one another by 180 degrees, such that they are aligned and on opposite sides of bore 152.

Each of protrusions 260 terminates in a tooth 264 protruding outward of protrusion 260 radially away from bore 152, each tooth having a bottom surface 266.

It is appreciated that for cooperation between the needle adaptor and the vial adaptor as described hereinbelow with reference to FIGS. 47C and 47D, the design of protrusions 260 and teeth 264 may vary while maintaining the functionality described herein. For example, in some embodiments, a single protrusion 260 may be used, while in other embodiments more than two protrusions 260 may be used. As another example, the teeth 264 of protrusions 260 may be directed radially away from bore 152 as illustrated, or, in some embodiments, may be directed radially towards bore 152 or sideways in a direction perpendicular to an imaginary line connecting the tooth 260 and bore 152. Referring now to FIG. 47C, it is seen that needle adaptor 259 may be connected to needle 106 within needle compartment 112 of casing 102. Similarly, vial adaptor 254 may be connected to syringe 220, substantially as described hereinabove with reference to FIGS. 44A and 44B. The syringe and vial adaptor are shown ready to connect to the needle adaptor and needle, substantially as described hereinabove with reference to FIG. 46A.

Turning finally to FIG. 47D, it is seen that when vial adaptor 254 is attached to needle adaptor 259, for example substantially as described hereinabove with reference to FIGS. 46A-46D, teeth 264 of needle adaptor 259 extend through slots 256 of vial adaptor 254, and surfaces 266 thereof engage frame 258. As such, the vial adaptor 254 and needle adaptor 259 irremovably snap fit together and cannot readily be separated.

It is appreciated that the irremovable snap fit between vial adaptor 104 and needle adaptor 109 may be accomplished in numerous ways other than that illustrated in FIG. 47D. For example, in some embodiments, the snap fitting teach 264 may extend along the circumferential side wall of body portion 150 of the needle adaptor 259, and interact with gaps 136 of vial adaptor 254. In other embodiments, the snap fitting teeth may form part of the vial adaptor 254, and may interact with suitably configured slots in needle adaptor 259. As another example, teeth 138 of vial adaptor 254 may be designed so as to reversibly engage a medicine vial, without snap fitting thereto, but permanently snap fit onto body portion 150 of needle adaptor 259. This can be accomplished, for example, but suitably designing the angles of the surfaces of body portion 150 of needle adaptor 259.

Reference is now made to FIG. 48A, which is an exploded view illustration of another system for interfacing between a syringe, a drug vial, and a needle, according to an embodiment of the teachings herein, to FIG. 48B, which is a simplified pictorial illustration of the system of FIG. 48A, as assembled, to FIG. 48C, which is a simplified pictorial illustration of the system of FIG. 48A in a needle connection operational position, and to FIG. 48D, which is a simplified pictorial illustration of the system of FIG. 48A, ready for injection.

As seen in FIG. 48A, an interfacing system 900 according to the teachings herein includes a casing 902 housing a needle 906 connected to a needle adaptor 909 and having a seal 908, as well as a syringe 910 connected to a vial adaptor 912 including a spike 913 protected by a spike shield 914.

The casing 902 is sized to house needle 906 so that the needle is substantially immobile therein. The needle 906 may be any suitable needle, including a standard hypodermic needle such as a BD Regular Bevel Needle or a safety needle such as a BD SafetyGlide Hypodermic Needle, both commercially available from Becton Dickinson and Company of 1 Becton Drive, Franklin Lakes, N.J. 07417-1880. In some embodiments, the needle 906 is an automatic injection needle, for example as disclosed in U.S. Pat. No. 7,901,382, filed on Sep. 15, 2004 and entitled "AUTOMATIC NEEDLE DEVICE" and in U.S. patent application Ser. No. 14/505,690, filed on Oct. 3, 2014 and entitled "AUTOMATIC NEEDLE APPARATUS" which are fully incorporated by reference herein.

The needle adaptor 909, is fitted to needle 906 within casing 902, is described hereinabove with reference to FIGS. 40A-40C and 41A-41C.

The seal 908 is operative to ensure the sterility of needle 906 and needle adaptor 909 while disposed within casing 902.

The syringe 910 may be any sterile syringe suitable for medical use, and may be prefilled with an injectable substance, such as a medicament. The vial adaptor 912 is in fluid flow communication with the lumen of syringe 910, and is preferably permanently and irremovably connected to the syringe 910. In some embodiments, such as the illustrated embodiment, the vial adaptor 912 may be integrally formed with syringe 910, for example formed of a single piece of plastic. In other embodiments (not illustrated), the vial adaptor may be any suitable vial adaptor, for example as described hereinabove with reference to FIGS. 38A-38D and 39A-39C, or a commercially available vial adaptor such as a vial adapter commercially available from West Pharmaceutical Services, Inc., of 530 Herman O. West Drive, Exton, Pa. 19341, USA, which has been permanently and irremovably connected to the end of syringe 910, for example by means of welding, adhesive, or any other suitable connection means.

In embodiments in which the syringe is prefilled, spike shield 914 includes a spike engagement portion 916, which is adapted to engage the spike 913 of vial adaptor 912, and in some embodiments also an inner wall portion of vial adaptor 912, thus sealing the spike and the lumen of syringe 910 and protecting the spike 913 of vial adaptor 912, as well as contents of syringe 910, from contamination. In some embodiments, the spike shield 914 further includes a protrusion 918, connected to spike engagement portion 916 and adapted to enable a user to grip the spike shield 914 for removal thereof from the vial adaptor 912, when necessary.

Turning to FIG. 48B, it is seen that in the assembled mode of system 900, prior to operation thereof, for example when provided to the user, the needle 906 and needle adaptor 909 are sealed within casing 902, and the spike shield 914 is attached to the spike 913 of vial adaptor 912, thus protecting the spike and the contents of syringe 910 connected to the vial adaptor. It will be appreciated that in some embodiments, for example when the syringe 910 is not pre-filled, the spike shield may be obviated.

In FIG. 48C it is seen that in a needle connection operational position, the user exposes needle 906 and needle adaptor 909, for example by removing seal 908 from casing 902 and/or by removing needle 906 and needle adaptor 909 from the casing. The user also exposes the spike 913 of vial adaptor 912 by removal of vial shield 914. The user then enables fluid flow between syringe 910 and needle 906 by pushing needle adaptor 909 into vial adaptor 912 such that spike 913 engages a lumen of needle adaptor 909, which is in fluid flow communication with the lumen of needle 906, substantially as described hereinabove with reference to FIGS. 46A to 46D. It will be appreciated that in some embodiments the user may push vial adaptor 912 onto needle adaptor 909 and may form fluid flow communication between the syringe and the needle while the needle adaptor 909 and needle 906 are still in casing 902, and may remove needle 906 from casing 902 only when the needle and syringe are ready for injection, as shown in FIG. 48D.

In FIG. 48D, the syringe 910 is connected to needle 906 via vial adaptor 912 and needle adaptor 909 and the system is ready for injection.

It will be appreciated that the connection between the vial adaptor and the needle adaptor may be accomplished using any suitable means, for example by snap fit engagement, by frictional engagement, and/or by a locking mechanism, for example as described hereinabove with reference to FIGS. 47A to 47D.

It will further be appreciated that the syringe 910 and vial adaptor 912 of FIG. 48B may also be removably connected to a vial, for example for mixing and/or reconstitution of medicaments, prior to connection thereof to the needle adaptor 909.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. An injection system comprising:
a housing coupled to:
a vial adaptor for connection to a vial;
a syringe connector, said connector rotatable between a first medicament filling orientation, and a second injection orientation; said connector removably coupled to said housing;
a hypodermic needle; and
a valve removably held within said housing, functionally associated with said vial adaptor, with said syringe connector, and with said hypodermic needle; said valve having a first medicament filling orientation wherein said syringe connector is in fluid flow communication with said vial adaptor; and a second injection orientation wherein said syringe connector is in fluid flow communication with said hypodermic needle,
wherein in said first medicament filling orientation of said valve, a longitudinal axis of said vial adaptor coincides with a longitudinal axis of said syringe connector;
wherein rotation of said syringe connector between said first orientation and said second orientation thereof, drives transition of said valve from said first medicament filling orientation to said second injection orientation.

2. The injection system of claim 1, wherein in said first orientation of said valve, said syringe connector is not in fluid flow communication with said needle.

3. The injection system of claim 1, wherein in said second orientation of said valve, said syringe connector is not in fluid flow communication with said vial adaptor.

4. The injection system of claim 1, wherein in said first orientation of said valve said vial adaptor is located in a first position and is connected to a port of said valve, and wherein in said second orientation of said valve, said vial adaptor is located in a second position, longitudinally displaced from said first position, and is disconnected from said valve.

5. The injection system of claim 4, wherein said disconnection between said vial adaptor and said valve is driven by rotation of said syringe connector.

6. The injection system of claim 1, wherein said vial adaptor is permanently connected to said port of said valve.

7. The injection system of claim 1, wherein in said second orientation, a longitudinal axis of said needle coincides with a longitudinal axis of said syringe connector.

8. The injection system of claim 1, wherein said needle comprises an automatic needle.

9. The injection system of claim 1, wherein, in said second orientation of said valve, said valve is locked and transition of said valve into said first orientation is prevented.

10. The injection system of claim 1, further comprising a casing enclosing said system in a sealed packing.

11. The injection system of claim 1, wherein said housing further includes at least one valve position marker, said valve position marker adapted to provide to a user an indication whether said valve is in said first orientation or in said second orientation; and wherein said valve indication comprises at least one of a visual indication, and audible indication, and a tactile indication.

12. The injection system of claim 1, wherein said housing further includes at least one vial adaptor position marker, said vial adaptor position marker adapted to provide to a user a vial adaptor indication whether said vial adaptor is connected to said valve or is disconnected from said valve, and wherein said vial adaptor indication comprises at least one of a visual indication, an audible indication, and a tactile indication.

13. The injection system of claim 1, wherein, in said first orientation of said valve, removal of said needle from said housing is prevented, and in said second orientation of said valve, said syringe connector; said valve, and said needle may be removed from said housing, as a single unit.

14. A method for preparing an injection device for injection, the method comprising:
providing the injection system of claim 1;
when said valve is in said first orientation, connecting a vial to said vial adaptor and connecting a syringe to said syringe connector;

drawing liquid from said vial into said syringe, said liquid passing through said vial adaptor, said valve, and said syringe connector;

rotating said syringe relative to said vial adaptor, thereby rotating said syringe connector and transitioning said valve from said first orientation to said second orientation and locking said valve so as to prevent transition of said valve back to said first orientation.

15. The method of claim 14, said drawing liquid including at least one of mixing and reconstituting of at least one of powder and a lyophilized drug with a liquid in said injection device.

16. The method of claim 15, said at least one of mixing and reconstituting further including removing said vial from said vial adaptor and connecting a second vial, different from said vial, to said vial adaptor.

17. The method of claim 14, wherein said needle, said valve, and said syringe connector are enclosed in said housing, the method further comprising removing said needle, said valve, said syringe connector, and said syringe, as a single unit, from said housing prior to injection of said medicament.

* * * * *